(12) United States Patent
Myers et al.

(10) Patent No.: US 7,960,559 B2
(45) Date of Patent: Jun. 14, 2011

(54) SYNTHESIS OF ENONE INTERMEDIATE

(75) Inventors: Andrew G. Myers, Boston, MA (US); Jason D. Brubaker, Cheshire, CT (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/833,628

(22) Filed: Jul. 9, 2010

(65) Prior Publication Data

US 2011/0009639 A1      Jan. 13, 2011

Related U.S. Application Data

(62) Division of application No. 11/870,772, filed on Oct. 11, 2007, now Pat. No. 7,763,735.

(60) Provisional application No. 60/850,859, filed on Oct. 11, 2006, provisional application No. 60/915,506, filed on May 2, 2007.

(51) Int. Cl.
   *C07D 261/20*       (2006.01)
(52) U.S. Cl. ..................................... 548/241
(58) Field of Classification Search ............... 548/241
   See application file for complete search history.

(56) References Cited

U.S. PATENT DOCUMENTS

| | | | |
|---|---|---|---|
| 2,482,055 A | 9/1949 | Duggar et al. | |
| 3,019,260 A | 1/1962 | McCormick et al. | |
| 3,109,007 A | 10/1963 | Blackwood et al. | |
| RE26,253 E | 8/1967 | Petisi et al. | |
| 3,338,963 A | 8/1967 | Petisi et al. | |
| 3,502,660 A | 3/1970 | Butler et al. | |
| 3,509,184 A | 4/1970 | Conover et al. | |
| 3,697,552 A | 10/1972 | Conover et al. | |
| 3,699,117 A | 10/1972 | Butler et al. | |
| 3,772,363 A | 11/1973 | Conover et al. | |
| 3,829,453 A | 8/1974 | Conover et al. | |
| 3,849,493 A | 11/1974 | Conover et al. | |
| 3,862,225 A | 1/1975 | Conover et al. | |
| 3,947,517 A | 3/1976 | Muxfeldt et al. | |
| 3,962,330 A | 6/1976 | Cotti et al. | |
| 3,983,173 A | 9/1976 | Hartung et al. | |
| 4,052,467 A | 10/1977 | Mills et al. | |
| 4,060,605 A | 11/1977 | Corti et al. | |
| 4,066,694 A | 1/1978 | Blackwood et al. | |
| 4,418,060 A | 11/1983 | Kahan nee Laszlo | |
| 4,597,904 A | 7/1986 | Page et al. | |
| 5,362,754 A | 11/1994 | Raad et al. | |
| 5,529,990 A | 6/1996 | Hlavka et al. | |
| 5,538,954 A | 7/1996 | Koch et al. | |
| 5,589,470 A | 12/1996 | Levy et al. | |
| 5,688,516 A | 11/1997 | Raad et al. | |
| 5,811,412 A | 9/1998 | Levy et al. | |
| 5,834,450 A | 11/1998 | Su et al. | |
| 6,143,161 A | 11/2000 | Heggie et al. | |
| 6,165,999 A | 12/2000 | Vu et al. | |
| 6,506,740 B1 | 1/2003 | Ashley et al. | |
| 6,509,319 B1 | 1/2003 | Raad et al. | |
| 6,617,318 B1 | 9/2003 | Nelson et al. | |
| 6,624,168 B2 | 9/2003 | Nelson et al. | |
| 6,638,532 B2 | 10/2003 | Rudnic et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 7,001,918 B2 | 2/2006 | Huss et al. | |
| 7,763,735 B2 | 7/2010 | Myers et al. | |
| 2002/0045602 A1 | 4/2002 | Nelson et al. | |
| 2002/0103171 A1 | 8/2002 | Nelson et al. | |
| 2002/0111335 A1 | 8/2002 | Nelson et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2002/0136766 A1 | 9/2002 | Rudnic et al. | |
| 2002/0193354 A1 | 12/2002 | Nelson et al. | |
| 2003/0055025 A1 | 3/2003 | Nelson et al. | |
| 2003/0096008 A1 | 5/2003 | Rudnic et al. | |
| 2003/0100017 A1 | 5/2003 | Draper et al. | |
| 2003/0153537 A1 | 8/2003 | Levy et al. | |
| 2003/0166585 A1 | 9/2003 | Draper et al. | |
| 2004/0048835 A1 | 3/2004 | Nelson et al. | |
| 2004/0063674 A1 | 4/2004 | Levy et al. | |
| 2004/0067912 A1 | 4/2004 | Hlavka et al. | |
| 2005/0282782 A1 | 12/2005 | Martin | |
| 2005/0282787 A1 | 12/2005 | Myers et al. | |
| 2007/0066253 A1 | 3/2007 | Sorrells et al. | |
| 2010/0130451 A1 | 5/2010 | Myers et al. | |

FOREIGN PATENT DOCUMENTS

EP     1 124 160 A1    9/2002

(Continued)

OTHER PUBLICATIONS

U.S. Appl. No. 60/790,413, filed Apr. 7, 2006, Myers.
U.S. Appl. No. 60/850,859, filed Oct. 11, 2006, Myers et al.
International Search Report and Written Opinion for PCT/US2007/081076 mailed Dec. 15, 2008.
International Preliminary Report on Patentability for PCT/US2007/081076 mailed Apr. 23, 2009.
Supplementary European Search Report for EP 05779988.4 mailed Jun. 9, 2009.
International Search Report and Written Opinion for PCT/US2005/017831 mailed May 4, 2006.

(Continued)

*Primary Examiner* — Jason M Nolan
(74) *Attorney, Agent, or Firm* — Wolf, Greenfield & Sacks, P.C.; C. Hunter Baker

(57) ABSTRACT

The tetracycline class of antibiotics has played a major role in the treatment of infectious diseases for the past 50 years. However, the increased use of the tetracyclines in human and veterinary medicine has led to resistance among many organisms previously susceptible to tetracycline antibiotics. The recent development of a modular synthesis of tetracycline analogs through a chiral enone intermediate has allowed for the efficient synthesis of novel tetracycline analogs never prepared before. The present invention provides a more efficient route for preparing the enone intermediate.

11 Claims, 2 Drawing Sheets

FOREIGN PATENT DOCUMENTS

| | | |
|---|---|---|
| FR | 2 279 720 A1 | 2/1976 |
| GB | 973022 A | 10/1964 |
| GB | 1013576 A | 12/1965 |
| GB | 1013906 A | 12/1965 |
| GB | 1019562 A | 2/1966 |
| GB | 1019563 A | 2/1966 |
| WO | WO 95/22529 A1 | 8/1995 |
| WO | WO 01/98236 A2 | 12/2001 |
| WO | WO 01/98259 A1 | 12/2001 |
| WO | WO 01/98260 A1 | 12/2001 |
| WO | WO 02/04404 A1 | 1/2002 |
| WO | WO 02/04406 A2 | 1/2002 |
| WO | WO 02/04407 A2 | 1/2002 |
| WO | WO 02/12170 A1 | 2/2002 |
| WO | WO 02/072532 A1 | 9/2002 |
| WO | WO 02/085303 A2 | 10/2002 |
| WO | WO 03/005971 A2 | 1/2003 |
| WO | WO 03/057169 A2 | 7/2003 |
| WO | WO 03/076424 A1 | 9/2003 |
| WO | WO 2005/112945 A2 | 12/2005 |
| WO | WO 2005/112985 A2 | 12/2005 |
| WO | WO 2007/117639 A2 | 10/2007 |
| WO | WO 2007/118237 A2 | 10/2007 |
| WO | WO 2008/127361 A2 | 10/2008 |

OTHER PUBLICATIONS

International Preliminary Report on Patentability for PCT/US2005/017831 mailed Nov. 30, 2006.
International Search Report and Written Opinion for PCT/US2007/008647 mailed Mar. 14, 2008.
International Preliminary Report on Patentability for PCT/US2007/008647 mailed Oct. 16, 2008.
Notice of Allowance mailed Apr. 7, 2010 U.S. Appl. No. 11/870,772.
Office Communication mailed Oct. 27, 2009 for U.S. Appl. No. 11/133,789.
Notice of Allowance mailed Feb. 22, 2010 for U.S. Appl. No. 11/133,789.
Akgun et al., Metalation of 0-Halostyrenes Oxides. Preparation of Benzocyclobutenols. J. Org. Chem. 1981;46:2730-2734.
Allen et al., A Powerful o-Quinone Dimethide Strategy for Intermolecular Diels—Alder Cycloadditions. J. Am. Chem. Soc. 2000;122:571-575.
Allen et al., The Total Synthesis of (±)-Rishirilide B. Am. Chem. Soc. 2001;123:351-352.
Amaro et al., Synthesis of Tetracyclic Hydroxyquinones by Cycloaddition Reactions With Dienols. Tetrahedron Lett. 1979:3983-3986.
Ballard et al., A Biotech Route to Polyphenylene. J. Chem. Soc. Chem. Commun 1983:954-955.
Barr et al., Zirconocene(iso-butyl) Chloride: In Situ Generation of a Zirconocene(methyl) Chloride Equivalent for Use in Organic Synthesis. Tetrahedron Lett. 1991;32:5465-5468.
Beard et al., Inhibition of Mammalian Protein Synthesis by Antibiotics. Pharmacol. Revs. 1969;21: 213-245.
Becker et al., Oxidative Formation and Photochemical Isomerization of Spiro-Epoxy-2,4-Cyclohexadienones. Tetrahedron Lett. 1972;13:4205-4208.
Beereboom et al., Further 6-Deoxytetracycline Studies: Effect of Aromatic Substituents on Biological Activity. J. Am. Chem. Soc. 1960;82:1003-1004.
Berge et al., Pharmaceutical Salts. J. Pharmaceutical Sciences 1977;66:1-19.
Berk et al., Preparations and Reactions of Functionalized Benzylic Organometallics of Zinc and Copper. Organometallics. 1990;9:3053-3064.
Boothe et al., Identification of an Antibiotic Polyacetylene From Clitocybe Diatreta As a Suberamic Acid Ene-Diyne. J. Am. Chem. Soc.1953;75:4621.
Boudier et al., New Applications of Polyfunctional Organometallic Compounds in Organic Synthesis Frequently used abbreviations are defined at the end of the article. Angew Chem Int Ed Engl. Dec. 15, 2000;39(24):4414-4435.

Brodersen et al.,The Structural Basis for the Action of the Antibiotics Tetracycline, Pactamycin, and Hygromycin B on the 30S Ribosomal Subunit. Cell. 2000;103:1143-1154.
Brown et al., Activities of the Glycylcyclines N,N-Dimethylglycylamido-Minocycline and N,N-Dimethylglycylamido-6-Deoxytetracycline Against Nocardia spp. And Tetracycline-Resistant Isolates of Rapidly Growing Mycobacteria. Antimicrob. Agents Chemother. 1996;40:874-878.
Brubaker et al., A practical, enantioselective synthetic route to a key precursor to the tetracycline antibiotics. Org Lett. Aug. 30, 2007;9(18):3523-5. Epub Aug. 11, 2007.
Burdett, Purification and Characterization of Tet(M), a Protein That Renders Ribosomes Resistant to Tetracycline. J. Biol. Chem. 1991;266:2872-2877.
Burke, Flexible tetracycline synthesis yields promising antibiotics. Nat Chem Biol. Feb. 2009;5(2):77-9.
Bush et al., Taking Inventory: Antibacterial Agents Currently At or Beyond Phase 1. Curr. Opin. Microbiol. 2004;7:466-476.
Cane et al., Harnessing the Biosynthetic Code: Combinations, Permutations, and Mutations. Science 1998;282:63-68.
Carless, the Use of Cyclohexa-3,5-Diene-1,2-Diols in Enantiospecific Synthesis. Tetrahedron Asymmetry. 1992;3:795-826.
Charest et al., A convergent enantioselective route to structurally diverse 6-deoxytetracycline antibiotics. Science. 2005;308:395-398.
Charest et al., Synthesis of (-)-Tetracycline. J. Am. Chem. Soc. 2005;127: 8292-93.
Charette et al., Spectroscopic studies of the electrophilic activation of amides with triflic anhydride and pyridine. CA J Chem. 2001;79:1694-1703.
Col. et al., Estimating Worlwide Current Antibiotic Usage: Report of Task Force 1. Reviews of Infectious Diseases. 1987;3: S232-43.
Conover et al., Terramycin. XI. Tetracycline. J. Am. Chem. Soc. 1953;75:4622-23.
Conover et al., The Total Synthesis of 6-Demethyl-6-Deoxytetracycline. J. Am. Chem. Soc. 1962;84:3222-24.
Corey et al., Dimethyloxosulfonium Methylide ((CH3)2SOCH2) and Dimethylsulfonium Methylide ((CH3)2SOCH2). Formation and Applicaton to Organic Synthesis. J. Am. Chem. Soc. 1965;87:1353-1364.
Corey et al., Highly Enantioselective Borane Reduction of Ketones Catalyzed by Chiral Oxaborolidines. Mechanism and Synthetic Implications. J. Am. Chem. Soc. 1987;109:5551-5553.
Corey et al., Practical Enantioselective Diels-Alder and Aldol Reactions Using a New Chiral Controller System. J. Am. Chem. Soc. 1989;111:5493-5495.
Corey et al., Reduction of Carbonyl Compounds With Chiral Oxaborolidine Catalysts: A New Paradigm for Enantioselective Catalysis and a Powerful New Synthetic Method. Angew. Chem. Int. Ed Engl.1988;37:1986-2012.
Corey et al., Studies With Trialkylsityltrifiates: New Synthesis and Applications. Tetrahedron Lett. 1981;22:3455-3458.
Dale et al., Nuclear Magnetic Resonance Enantiomer Reagents. Confiigurational Correlations via Nuclear Magnetic Resonance Chemical Shifts of Diastereomeric Mandelate, O-Methylmandelate and α-Methoxy-α-trifluoromethylphenylacetate (MTPA) Esters. J Am Chem Soc. 1973;95:512-19.
Dale et al., α-Methoxy- αTrifluoromethylphenylacetic Acid, A Versatile Reagent for the Determination of Enantiometric Composition of Alcohols and Amines. J. Org. Chem. 1969;34:2543-2549.
Danishefsky et al., Functionalized Alanes for the Conversion of Epoxides to Trans-Fused γ-Lactones. J Org Chem. 1976;41:1669-71.
Davis et al., Chemistry of Oxaziridines. 18. Synthesis and Enantioselective Oxidations of the [(88- Dihalocamphoryl) Sulfonyl] Oxaziridines. J. Org. Chem. 1992;57:7274-7285.
De Silva et al., Directed Lithiation of N,N-Diethylbenzamides. Tetrahedron Lett. 1978;51:5099-5102.
De Silva et al., General Route to Anthraquinone Natural Products via Directed Metalation of N,N-Diethylbenzamides. J. Org. Chem. 1979;44:4802-4808.
Detty, Electrophilic Conversion of Oxiranes to Allylic Alcohols with tert-Butyldimethylsilyl Iodide. J. Org. Chem. 1980;45:924-926.

Devasthale et al., Dactylocyclines Novel Tetracycline Derivatives Produced by a Dactylosporangium. Antibiotics. 1992;45:1907-1913.
Ditrich et al., Synthesis of a Protected C-11/C-17 Segment of Mycinolide-V. Liebigs Ann. Chem. 1990:15-21.
Dodd et al., Synthesis of the Carbon Framework of Olivin. Tetrahedron Lett. 1979;20:3593-3596.
Duggar, Aureomycin: A Product of the Continuing Search for New Antibiotics. Ann. N.Y. Acad. Sci. 1948;51:177-181.
Duhamel et al., A Method for Simple Titration of Organolithium Reagents in Ethers or HydrocarbonsUsing Metalation of N-Benzylidenebenzylamine As Colored Reaction. J. Org. chem. 1979;44:3404-3405.
Eckert et al., Topology of the Transposon Tn10-Encoded Tetracycline Resistance Protein Within the Inner Membrane of *Escheria coli*. J. Biol. Chem. 1989;264:11663-11670.
Epe et al., Competition Between Tetracycline and tRNA At Both P And A Sites of the Ribosome of *Escheria coil*. FEBS Lett. 1987;213:443-47.
Epe et al., The Binding of 6Demethylchlorotetracyline to 70S, 50S, and 30S Ribosomal Particles-A Quantitative Study by Fluorescence Anisotropy. EMBO J. 1984;3:121-26.
Ettner et al., Proximity Mapping of the Tet Repressor-Tetracycline-Fe2+ Complex by Hydrogen Peroxide Mediated Protein Cleavage. Biochemistry. 1995;34:22-31.
Finlay et al., Terramycin, A New Antibiotic. Science 1950;111:85.
Franklin et al., Resistance of *Escherichia coli* to Tetracyclines. Biochem J. 1965;94:54-60.
Franklin, The Inhibition of Incorporation of Leucine Into Protein of Cell-Free Systems From Rat Liver and *Escherichia coll* by Chlortetracycline. Biochem. J. 1963;87:449-453.
Frigerio et al., A Mild Oxidizing Reagent for Alcohols and, 1,2-Diols: o-Iodoxybenzoic Acid (IBX) in DMSO. Tetrahedron Lett. 1994;35:8019-8022.
Gibson et al., Oxidative Degradation of Aromatic Hydrocarbons by Microorganisms. II. Metabolism of Halogenated Aromatic Hydrocarbons. Biochemistry 1968;7:3795-3802.
Goldman et al., Photoincorporation of Tetracycline Into *Escherichia coil* Ribosomes. Identification of the Major Proteins Photolabeled by Native Tetracycline and Tetracycline Photoproducts and Implications for the Inhibitory Action of Tetracycline on Protein Synthesis. Biochemistry. 1983;22:359-368.
Goldstein et al., N,N-Dimethylglycyl-Amido Derivative of Minocycline and 6-Demethyl-6-Desoxytetracycline, Two New Glycylcyclines Highly Effective Against Tetracycline-Resistant Gram-Positive Cocci. Antimicrob. Agents Chemother. 1994;38:2218-2220.
Gurevich et al., Synthesis of 12a-Deoxy-5a,6-Anhydrotetracycline. The First Total Synthesis of the Naturally Occurring Tetracycline. Tetrahedron Lett. 1967;8:131-134.
Hauser et al., ortho-Toluate Carbanion Chemistry: Sulfenylation and Selenation. Synthesis. 1980: 72-74.
Hauser et al., New Synthetic Methods for the Regioselective Annelation of Aromatic Rings: 1-Hydroxy-2,3-disubstituted Naphthalenes and 1,4-Dihydrocy-2,3-disubstituted Naphthalenes. J Org Chem. 1978;43:178-180.
He et al., Pyrrocidines A and B, New Antibiotics Produced by a Filamentous Fungus. Tetrahedron Letters. 2002;43:1633-36.
Hiilen et al., Control of the Expression of the Tn10-Encoded Tetracycline Resistance Genes. Equilibrium and Kinetic Investigation of the Regulatory Reactions. J. Mol. Biol. 1983;169:707-721.
Hinrichs et al., Structure of the Tet Repressor-Tetracycline Complex and Regulation of Antibiotic Resistance. Science. 1994;264:418-420.
Hochstein et al., Terramycin. VII. The Structure of Terramycin. J. Am. Chem. Soc.1952;74:3708-3709.
Hochstein et al., The Structure of Terramycin. J. Am. Chem Soc. 1953;75:5455-75.
Hollinshed et al., Two Practical Syntheses of Sterically Congested Benzophenones. J. Org. Chem. 1994;59:6703-6709.
Holmuland et al., Chemical Hydroxylation of 12a-Dexytetracycline. J. Am. Chem. Soc. 1959;81: 4748-4749.

Hong et al., Lewis acid-promoted alpha-hydroxy beta-dicarbonyl to alpha-ketol ester rearrangement. Tetrahedron Lett. Nov. 20, 2006;47(47):8387-8390.
Hudlicky et al., A Short Synthesis of (+)-Lycoricidne. J. Am. Chem. Soc. 1992;114: 9694-9696.
Hudlicky et al., Enantioselective Synthesis Through Microbial Oxidation of Arenes. Efficient Preparation of Terpene and Prostanoid Synthons. J. Am. Chem. Soc. 1988;110:4735-4741.
Hudlicky et al., Enzymatic Dihydroxylation of Aromatics in Enantioselective Synthesis: Expanding Asymmetric Methodology. Aldrichimica Acta. 1999;32:35-62.
Hudlicky et al., Microbial Oxidation of Aromatics in Enantiocontrolled Synthesis. Rational DesignsOf Aza Sugars (endo-Nitrogenous). Total Synthesis of (+)-Kifunensine, Mannorjirimycin, and Other Glycosidase Inhibitors. J. Am. Chem. Soc. 1994;116:5099-5107.
Hudlicky et al., Toluene Dioxygenase-Mediated cis-Dihydroxylation of Aromatics in Enantioselective Synthesis. Asymmetric Total Synthesis of Pancratistatin and 7-Deoxpancratistatin, Promising Antitumor Agents. J. Am. Chem. Soc. 1996;118:10752-10765.
Hyatt et al., Thermal Decomposition of 2,2,6-Trimethyl-4H-1,3-Dioxin-4-One and 1-Ethoxybutyn-3-One. Acetylketene. J. Org. Chem. 1984;49:5105-5108.
Jacouinet et al., Synthesis of Heparin Fragments. A Chemical Synthesis of the Trisaccharide 0-(2-Deoxy-2-Sulfamido-3.6-DI-O-Sulfo-a-D-Glucopyranosyl)-(1→ 4)-0-(2-0- Sulfo-a-L-Idopyranosyl-Uronic Acid)-(1→4)-2-Deoxy-2-Sulfamido-6-0-Sulfo-D-Gluco- Pyranose Heptasodium Salt. Carbohydr. Res. 1984;130:221-241.
Jenkins et al., Synthetic application of biotransformations: absolute stereochemistry and Diels-Alder reactions of the (1S,2R)-1,2-dihydroxycyclohexa-3,5-diene-1-carboxylic acid from *Pseudomonas putida*. J Chem Soc Perkin Trans. 1995;1:2647-55.
Jensen et al, Unsaturated Four-Membered Ring Compounds. II. 1,2-Diphenylbenzocyclobutene, A Compound Having Unusual Reactivity. J. Am. Chem. Soc.1958; 80:6149.
Johns et al., Synthesis and Biological Evaluation of Aza-C-Disaccharides: (1→6), (1-44), and (1→22 1) Linked Sugar Mimics. J. Am. Chem. Soc. 1997;119:4856-4865.
Johnson et al., Triply Convergent Synthesis of (-)-Prostaglandin E2 Methyl Ester. J Am Chem Soc. 1988;110:4726-4735.
Johnson, Biotransformations in the Synthesis of Enantiopure Bioactive Molecules. Acc Chem Res. 1998;31:333-341.
Katz, Manipulation of Modular Polyketide Synthases. Chem. Rev. 1997;97:2557-2575.
Kenny et al., Susceptibilities of Mycoplasma Hominis, Mycoplasma Pneumoniae, and Ureaplasma Urealyticum to New Glycylcyclines in Comparison With Those to Older Tetracyclines. Antimicrob. Agents Chemother. 1994;38:2628-2632.
Khosla et al., Chemistry. A new route to designer antibiotics. Science. Apr. 15, 2005;308(5720):367-8.
Kofron et al., A Convenient Method for Estimation of Alkyllithium Concentrations. J Org Chem. 1976;41:1879-80.
Konno et al., A Practical Preparation of Versatile Cyclohexenoid Chiral Building Blocks. Synthesis. 1999:1135-40.
Korst et al., The Total Synthesis of d/-6-Demethyl-6-Deoxytetracycline. J. Am. Chem. Soc. 1968;90: 439-457.
Koza et al., Synthesis and Biological Evaluation of 9-Substituted Tetracycline Derivatives. Bioorgan. & Med. Chem. Letters. 2002;12: 2163-2165.
Koza et al., Synthesis of 7-Substituted Tetracycline Derivatives. Organic Letters. 2000;2:815-817.
Koza, The Synthesis of 8-Substituted Tetracycline Derivatives, The First 8-Position Carbon-Carbon Bond. Tetrahedron Lett. 2000;41:5017-5020.
Landais et al., Studies on the Mercury-desilylation of Chiral Cyclopropylmethylsilanes. A Stereocontrolled Access to Carba-sugars. Eur. J. Org. Chem. 2000;2:401-18.
Laskin et al, Inhibition by Tetracyclines of Polyuridylic Acid Directed Phenylalanine Incorporation in *Escherichia coli* Cell- Free Systems. Biochem Biophys. Res. Commun 1964;14:137-142.

Lederer et al., Thermodynamic Analysis of Tetracycline-Mediated Induction of Tet Repressor by a Quantitative Methylation Protection Assay. Anal. Biochem. 1995;232:190-196.
Leeb, A Shot in the Arm. Nature. 2004;431:892-893.
Leeper et al., Biomimetric Synthesis of Heptaketide Metabolites: Alternariol and A Derivative of Rubrofusarin. J.C.S. Chem. Comm 1978:406-407.
Levy, Tetracycline Resistance Determinants Are Widespread. Amer. Soc. Microbial News. 1988;54: 418-421.
Ley et al., Microbial Oxidation in Synthesis: A Six Step Preparation of (+)-Pinitol From Benzene. Tetrahedron Lett. 1987;28:225-226.
Mao et al., Mode of Action of β-Chelocardin. Biochim. Biophys. Acta. 1971;238: 157-160.
Marchand et al., Facile Stereoselective Reductions of Enediones and Cage Diketones Using NaBH4-CeC13. J Org Chem. 1986;51:1622-25.
Marger et al., A Major Superfamily of Transmembrane Facilitators That Catalyse Uniport, Symport and Antiport. Trends Biochem Sci. 1993;18:13-20.
Martell et al., The 6-Deoxytetracyclines. IX. Imidomethylation. J. Med. Chem. 1967;10:359-363.
Martell et al., The 6-Deoxytetracyclines. VII. Alkylated Aminotetracyclines Possessing Unique Antibacterial Activity. J. Med. Chem. 1967;10: 44-46.
McComsey et al., Improved Synthesis of Pseudo-13-D-Fructopyranose, A Carbocyclic Monosaccharide, From (-)-Quinic Acid. J. Org. Chem. 1994;59:2652-2654.
McCormick et al., The 6-Deoxytetracyclines. Further Studies on the Relationship Between Structure and Antibacterial Activity in the Tetracycline Series. J. Am. Chem. Soc. 1960;82: 3381-3386.
Meister et al., Synthese von 3(2H)-Furanonen and 3-Methoxyfuranen. Synthesis; 1981:737-39.
Mendez et al., Heterogeneity of Tetracycline Resistance Determinants. Plasmid. 1980;3:99-108.
Mercier et al., In Vitro Activities of an Investigational Quinolone, Glycylcycline, Glycopeptide, Streptogramin, and Oxazolidinone Tested Alone and in Combinations Against Vancomycin-Resistant Enterococcus Faecium. Antimicrob Agents Chemother. 1997;41: 2573-2575.
Movassaghi et al., Direct synthesis of pyridine derivatives. J Am Chem Soc. 2007 Aug 22;129(33):10096-7. Epub 2007 Jul. 31.
Movassaghi et al., Single-step synthesis of pyrimidine derivatives. J Am Chem Soc. 2006 Nov 8;128(44):14254-5.
Movassaghi et al., Synthesis of substituted pyridine derivatives via the ruthenium-catalyzed cycloisomerization of 3-azadienynes. J Am Chem Soc. Apr. 12, 2006;128(14):4592-3.
Muxfeldt et al., Tetracyclines. 9. Total Synthesis of dl-Terramycin. J. Am. Chem. Soc. 1979;101:689-701.
Muxfeldt et al., Tetracyclines. V. A Total Synthesis of (±)-6-Deoxy-6-Demethyltetracycline. J. Am. Chem. Soc. 1965;87:933-934.
Muxfeldt et al., Total Synthesis of Anhydroaureomycin. Angew Chem. Intl. Ed. EngL 1973;12: 497-499.
Myers et al., An Efficient Method for the Reductive Transposition of Allylic Alcohols. Tetrahedron Lett. 1996;37:4841-4844.
Myers et al., A Convergent Synthetic Route to (+)-Dynemicin A and Analogs of Wide Structural Variability. J. Am. Chem. Soc. 1997;119:6072-6094.
Myers et al., Synthesis of a Broad Array of Highly Functionalized, Enantiomerically Pure Cyclohexanecarboxylic Acid Derivative by Microbal Dihydroxylation of Benzoic Acid and Subsequent Oxidative and Rearrangement Reactions. Organic Letters. 2001;3(18):2923-26.
Nakashima et al., A Stereocontrolled Route to (−)-Epibatidine Using a Chiral cis-Cyclohexadiene-1,4-diol Equivalent. Synlett. 1999:1405-6.
Nelson et al., Versatile and Facile Synthesis of Diverse Semisynthetic Tetracycline Derivatives Via Pd-Catalyzed Reactions. J. Org. Chem. 2003;68: 5838-5851.
Nicolaou et al., Recent advances in the chemistry and biology of naturally occurring antibiotics. Angew Chem Int Ed Engl. 2009;48(4):660-719.
Oda et al., 2-Cyclohexene-1,4-Dione. Org Syntheses. 1996;73:253.

Oikawa et al., Biosynthesis of Structurally Unique Fungal Metabolite GKK1032A2: Indication of Novel Carbocyclic Formation Mechanism in Polyketide Biosynthesis. J. Org. Chem. 2003;68: 3552-3557.
Oikawa et al., Kinetic Acetalization for 1, 2- And 1, 3-Diol Protection by the Reaction of p-Methoxyphenylmethyl Methyl Ether With DDQ. Tetrahedron Lett. 1983;24:4037-4040.
Okamoto et al., Mechanism of Chloramphenicol and Tetracycline Resistance in *Escherichia coli*. J Gen. Microb. 1964;35:125-133.
Oliva et al., Evidence That Tetracycline Analogs Whose Primary Target Is Not the Bacterial Ribosome Cause Lysis of *Escherichia cox* Antimicrob. Agents Chemother. 1992;36:913-919.
Osman et al., Synthesis and Biological Activity of Certain Nicotinic Acid Derivatives. Revue Roumaine de Chime. 1986;31:615-624.
Pangborn et al., Safe and Convenient Procedure for Solvent Purification. Organometallics. 1996;15:1518-1520.
Paradies et al., A New Method for the Preparation of Organomagnesium Compounds of Pyridine. Angew. Chem. Int. Ed. Engl. 1969;8:279.
Parham et al., Selective Halogen-Lithium Exchange in Bromophenylalkyl Halides. J. Org. Chem. 1976; 41: 1184-1186.
Patel et al., A New Tetracycline Antibiotic From A Dactylosporangium Species. Antibiotics. 1987;40:1414-1418.
Peláez, The historical delivery of antibiotics from microbial natural products—can history repeat? Biochem Pharmacol. Mar. 30, 2006;71(7):981-90. Epub Nov. 14, 2005.
Pelter et al., Phenolic Oxidation With (Diacetoxyiodo) Benzene. Tetrahedron Lett. 1988;29: 677-680.
Pevarello et al., An Improved Synthesis of Muscimol. Synth. Commun. 1992;22:1939-1948.
Pickens et al., Decoding and engineering tetracycline biosynthesis. Metab Eng. Mar. 2009;11(2):69-75. Epub Oct. 22, 2008.
Pierce et al., Practical Asymmetric Synthesis of Efavirenz (DMP 266), an HIV-1 Reverse Transcriptase Inhibitor. J Org Chem. 1998;63:8536-43.
Pine, The Base-Promoted Rearrangements of Quaternary Ammonium Salts. Organic Reactions. 1970;18:403-433.
Pioletti et al., Crystal Structures of Complexes of The Small Robosomal Subunit With Tetracycline, Edeine, And 1F3. EMBO J. 2001;20:1829-1839.
Prilezhaeva, Rearrangements of Sulfoxides and Sulfones in the Total Synthesis of Natural Compounds. Russ. Chem. Rev. 2001;70: 897-920.
Rassmussen et al., Molecular Basis of Tetracycline Action: Identification of Analogs Whose Primary Target Is Not The Bacterial Ribosome. Antimicrob. Agents Chemother. 1991;35:2306-11.
Rassmussen et al., Inhibition of Protein Synthesis Occurring on Tetracycline-Resistant, TetM-Protected Ribosomes By A Novel Class of Tetracyclines, the Glycylcyclines. Antimicrob. Agents Chemother. 1994;38:1658-1660.
Reineke et al., cis-Dihydrodiols Microbially Produced From Halo- And Methylbenzoic Acids. Tetrahedron. 1978;34:1707-1714.
Reiner et al., Metabolism of Benzoic Acid by Bacteria, Accumulation of (-)-3,5-Cyclohexadiene-1,2—Dio1-1-Carboxylic Acid by A Mutant Strain of Alcaligenes Eutrophus. Biochemistry. 1971;10:2530-2536.
Rendi et al., Effect of Chloramphenicol on Protein Synthesis in Cell-free Preparations of *Escherichia coli*. J. Biol. Chem. 1962;237:3711-3713.
Riess et al., Evaluation of Protecting Groups for 3-Hydroxyisoxazoles—Short Access to 3-Alkoxyisoxazole-5-Carbaldehydes And 3-Hydroxyisoxazole-5-Carbaldehyde, the Putative Toxic Metabolite of Muscimol. Eur. J. Org. Chem. 1998:473-479.
Rogalski, Chapter 5. Chemical Modification of Tetracyclines. Handbook of Experimental Pharmacology. 1985:179-316.
Rossiter et al., Aromatic Biotransformations 2: Production of Novel Chiral Fluorinated 3,5-Cycloheadiene-CIS-1,2-Dio1-1-Carboxylates. Tetrahedron Lett. 1987;28:5173-5174.
Saenger et al., The Tetracycline Repressor—A Paradigm for a Biological Switch. Angew. Chem. Int. Ed. 2000;39:2042-2052.
Sanchez-Pescador et al., Homology of the TetM With Translational Elongation Factors: Implications for Potential Modes of tetM Conferred Tetracycline Resistance. Nucl. Acids. Res. 1988;16:1218.

Sato et al., Synthesis of 1,3-Dioxin-4-One Deirvatives. Chem. Pharm. Bull. 1983;31:1896-1901.

Schnappinger et al., Tetracyclines: Antibiotic Action, Uptake, and Resistance Mechanisms. Arch. Microbiol. 1996;165:359-369.

Scott et al., Simulation of the Biosynthesis of Tetracyclines. A Partial Syntheis of Tetracycline From Anhydroaureomycin. J Am. Chem. Soc. 1962;84:2271-2272.

Singer et al., Catalytic, Enantioselective Dienolate Additions to Aldehydes: Preparation of Optically Active Acetoacetate Aldol Adducts. J. Am. Chem. Soc. 1995;117:12360-12361.

Stephens et al., 6-Deoxytetracyclines. IV. Preparation, c-6 Stereochemistry, and Reactions. J. Am. Chem. Soc. 1963;85:2643-2652.

Stephens et al., Terramycin. VIII. Structure of Aureomycin and Terramycin. J. Am. Chem. Soc. 1952;74: 4976-77.

Stephens et al., The Structure of Aureomycin. J. Am. Chem. Soc. 1954;76:3568-75.

Stevens et al., Degradation of Quaternary Ammonium Salts. Part I. J. Chem. Soc. 1928: 3193-3197.

Stevens, Degradation of Quaternary Ammonium Salts. Part II. J Chem. Soc. 1930:2107-2125.

Still et al., Rapid Chromatographic Technique for Preparative Separations With Moderate Resolution. J. Org. Chem. 1978;43:2923-2925.

Stork et al., 3-Benzyloxyisoxazole System in Construction of Tetracyclines. J Am Chem Soc. 1978;100(11):3609-11.

Stork et al., Stereocontrolled Synthesis of (±)-12a-Deoxytetracycline. J. Am. Chem. Soc. 1996;118:5304-5305.

Strohl, Biochemical Engineering of Natural Product Biosynthesis Pathways. Metabolic Engineering. 2001;3:4-14.

Sum et al., Glycylcylines. 1. A New Generation of Potent Antibacterial Agents Through Modification of (-Aminotetracyclines. J. Med. Chem. 1994;37:184-188.

Sum et al., Recent developments in tetracycline antibiotics. Curr Pharm Des. 1998 Apr;4(2):119-32.

Sum et al., Synthesis and Structure—Activity Relationship of Novel Glycylcycline Derivatives Leading to the Discovery of Gar-936. Bioorg. Med. Chem. Lett. 1999;9:1459-1462.

Sum et al., Synthesis of Novel Tetracycline Derivatives With Substitution At the C-8 Position. Tetrahedron Lett. 1994;35:1835-1836.

Sum et al., The Design, Synthesis and Structure-Activity Relationships of Novel Glycylcycline Derivatives: A New Generation of Tetracycline Antibacterial Agents. 24th National Medicinal Chemistry Symposium Utah. 1994; 83:119. (Abstract Only).

Sun et al., A robust platform for the synthesis of new tetracycline antibiotics. J Am Chem Soc. Dec. 31, 2008;130(52):17913-27.

Suzuki et al., Palladium(0) Catalyzed Reaction of 1,3-Diene Epoxides. A Useful Method for the Site Specific Oxygenation of 1,3-Dienes. J. Am. Chem. Soc. 1979;101:1623-1625.

Takano et al., Enantiodivergent Preparation of Chiral 2,5-Cyclohexadienone Synthons. Synthesis. 1993;(7): 948-50.

Tatsuta et al., The First Total Synthesis of Natural (−)-Tetracycline. Chem. Lett. 2000:646-47.

Tatsuta, Total synthesis and development of bioactive natural products. Proc Jpn Acad Ser B Phys Biol Sci. 2008;84(4):87-106.

Tatsuta et al., Total syntheses of bioactive natural products from carbohydrates. Sci Tech Adv Mater. 2006;7:397-410.

Tatsuta et al., Total syntheses of polyketide-derived bioactive natural products. Chem Rec. 2006;6(4):217-33.

Tatsuta et al., Total synthesis of selected bioactive natural products: illustration of strategy and design. Chem Rev. Dec. 2005;105(12):4707-29.

Taylor, Reactions of Epoxides With Ester, Ketone and Amide Enolates. Tetrahedron. 2000;56:1149-1163.

Testa et al., In Vitro and In Vivo Antibacterial Activities of the Glycylcyclines, A New Class of Semisynthetic Tetracyclines. Antimicrob. Agents Chemother. 1993;37:2270-2277.

Tolchin et al., Synthesizing New Antibiotics. Drug Discov & Develop: Reed Life Science News. Apr. 14, 2005.

Tovar et al., Identification and Nucleotide Sequence of the Class E tet Regulatory Elements and Operator and Inducer Binding of the Encoded Purified Tet Repressor. Mol. Gen. Genet. 1988;215:76-80.

Travis, Receiving the Antibiotic Miracle? Science. 1994;264:360-362.

Tymiak et al., Dactylocyclines, Novel Tetracycline Derivatives Produced by A Dactylosporangium sp. J. Antibiotics. 1992;45:1899-1906.

Tymiak et al., Dactylocyclines: Novel Tetracyclines Glycosides Active Against Tetracycline-Resistant Bacteria. J. Org. Chem. 1993;58:536-537.

Verma et al., Antibiotic and non-antibiotic tetracycline patents: 2002-2007. Expert Opin Thera Pat. 2008;18(1):69-82.

Vishwakarma et al., (±)-trans-2-(Phenylsulfonyl)-3-Phenyloxaziridine. Org Syntheses. 1988;66:203.

Vu et al., New Functionalized Alkenylmagnesium Reagents Bearing an Oxygen Function in the I3-Position. Preparation and Reaction of 5-Magnesiated-1,3-Dioxin-4-One Derivatives. Tetrehedron Lett. 2001;42:6847-6850.

Vyas et al., A Short, Efficient Total Synthesis of (±) Acivicin and (±) Bromo-Acivicin. Tetrahedron Lett. 1984;25:487-490.

Wasserman et al., On The Total Synthesis of tetracycline. J. Am. Chem. Soc. 1986;108:4237-4238.

Wang et al., Identification of OxyE as an ancillary oxygenase during tetracycline biosynthesis. Chembiochem. Jun. 15, 2009;10(9):1544-50.

Weiss et al., Susceptibility of Enterococci, Methicillin—Resistant *Staphylococcus aureus* and *Steptococcus pneumoniae* to the Glycylcyclines. J Antimicrob. Agents Chemother. 1995;36:225-230.

Wells et al., Dactylocyclines, novel Tetracycline Derivatives Produced by a Dactylosporangium sp. Antibiotics. 1992;45:1892-1898.

White et al., Stereochemical Transcription Via the Intramolecular Diels-Alder Reaction. Enantioselective Synthesis of (+)-Pillaromycinone. J. Org. Chem. 1986;51:1150-1152.

Wilson et al., Selective Reduction of 2-Ene-1,4-diones and 2-En-1-ones with Di-ibutylaluminium Hydride. J Chem Soc Chem Commun. 1970;(4):213-14.

Wissmann et at., Tetracylin-Resistenzdeterminanten: Machanismen der Resistenz und Regulation ihrer Epression. Forum Mikrobiol. 1998:292-299.

Woodward, The Total Synthesis of a Tetracycline. Pure Appl Chem. 1963;6:561-573.

Wu et al., [A new era for organic synthesis- Highlights of the recent progress.] Progress in Chemistry. 2007;19(1):6-34. Chinese. Translated copy from Front Chem China, 2007, 2(3):277-64.

Yarnell et al., Synthetic Route to Tetracyclines: Modular, flexible synthesis yields structurally diverse antibiotics. Chem & Eng News. 2005;83(16):9.

Yersin et al., Polarized Emission of [Ru(bpy)3] (PF5)2Single Crystals. J. Am. Chem. Soc. 1983;48: 4155-4156.

Zakeri et al., Chemical biology of tetracycline antibiotics. Biochem Cell Biol. Apr. 2008;86(2):124-36.

Zhang et al., Engineered biosynthesis of a novel amidated polyketide, using the malonamyl-specific initiation module from the oxytetracycline polyketide synthase. Appl Environ Microbiol. Apr. 2006;72(4):2573-80.

Zhao et al., Nucleotide Sequence Analysis of the Class G Tetracycline Resistance Determinant From Vibrio Anguillarm. Microbiol Immunol. 1992;36:1051-1060.

SYNTHESIS OF ENONE INTERMEDIATE

RELATED APPLICATIONS

The present application is a divisional of and claims priority under 35 U.S.C. §120 to U.S. patent application, U.S. Ser. No. 11/870,772, filed Oct. 11, 2007, which claims priority under 35 U.S.C. §119(e) to U.S. provisional patent applications, U.S. Ser. No. 60/850,859, filed Oct. 11, 2006, and U.S. Ser. No. 60/915,506, filed May 2, 2007, each of which is incorporated herein by reference.

GOVERNMENT SUPPORT

This invention was made with U.S. government support under grant R01 AI48825 and predoctoral fellowship 2004016101 awarded by the National Institutes of Health and the National Science Foundation, respectively. The U.S. government has certain rights in the invention.

BACKGROUND OF THE INVENTION

The tetracyclines are broad spectrum anti-microbial agents that are widely used in human and veterinary medicine (Schappinger et al., "Tetracyclines: Antibiotic Action, Uptake, and Resistance Mechanisms" *Arch. Microbiol.* 165: 359-69, 1996; Mitscher, *Medicinal Research Series*, Vol. 9, The Chemistry of the Tetracycline Antibiotics, Marcel Dekker Inc. New York, 1978). The total production of tetracyclines by fermentation or semi-synthesis is measured in the thousands of metric tons per year. The first tetracycline, chlorotetracycline (1) (Aureomycin™) was isolated from the soil bacterium *Streptomyces aureofaciens* by Lederle Laboratories (Wyeth-Ayerst Research) in the 1945 (Duggar, *Ann. N.Y. Acad. Sci.* 51:177-181, 1948; Duggar, Aureomycin and Preparation of Some, U.S. Pat. No. 2,482,055, 1949; incorporated herein by reference). Oxytetracycline (2) was isolated soon after from *S. rimosus* by scientists at Pfizer Laboratories (Finlay et al. *Science* 111:85, 1950). The structures of chlorotetracycline and oxytetracycline were elucidated by scientists at Pfizer in collaboration with R. B. Woodward and co-workers at Harvard University (Hochstein et al. *J. Am. Chem. Soc.* 74:3708-3709, 1952; Hochstein et al. *J. Am. Chem. Soc.* 75:5455-75, 1953; Stephens et al. *J. Am. Chem. Soc.* 74:4976-77, 1952; Stephens et al. *J. Am. Chem. Soc.* 76:3568-75, 1954). Tetracycline (3) was later prepared by the hydrogenolysis of chlorotetracycline and was found to retain the anti-microbial activity of chlorotetracycline and oxytetracycline and had increased stability (Boothe et al. *J. Am. Chem. Soc.* 75:4621, 1953; Conover et al. *J. Am. Chem. Soc.* 75:4622-23, 1953). Tetracycline was later found to be a natural product of *S. aureofaciens, S. viridofaciens*, and *S. rimosus*.

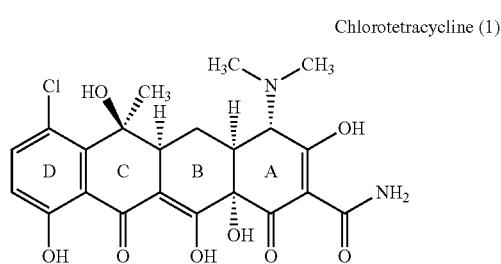

Chlorotetracycline (1)

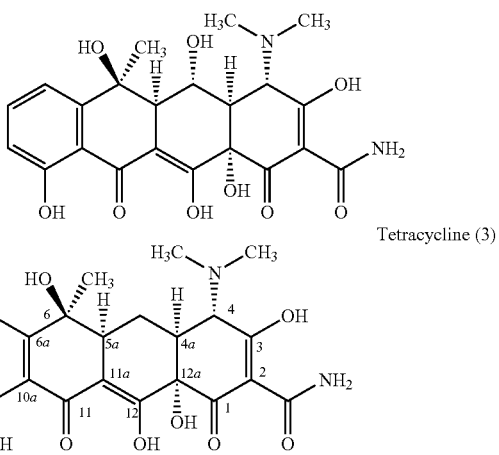

Oxytetracycline (2)

Tetracycline (3)

The primary tetracyclines of clinical importance today include tetracycline (3) (Boothe et al. *J. Am. Chem. Soc.* 75:4621, 1953), oxytetracycline (2, Terramycin™) (Finlay et al. *Science* 111:85, 1950), (−)-doxycycline (Stephens et al. *J. Am. Chem. Soc.* 85:2643, 1963), (−)-minocycline (Martell et al. *J. Med. Chem.* 10:44, 1967; Martell et al. *J. Med. Chem.* 10:359, 1967), and tigecycline. The tetracyclines exert their anti-microbial activity by inhibition of bacterial protein synthesis (Bentley and O'Hanlon, Eds., *Anti-Infectives: Recent Advances in Chemistry and Structure-Activity Relationships* The Royal Society of Chemistry: Cambridge, UK, 1997). Most tetracyclines are bacteriostatic rather than bactericidal (Rasmussen et al. *Antimicrob. Agents Chemother.* 35:2306-11, 1991; Primrose and Wardlaw, Ed. "The Bacteriostatic and Bacteriocidal Action of Antibiotics" *Sourcebook of Experiments for the Teaching of Microbiology* Society for General Microbiology, Academic Press Ltd., London, 1982). It has been proposed that after tetracycline passes through the cytoplasmic membrane of a bacterium it chelates $Mg^{+2}$, and this tetracycline-$Mg^{+2}$ complex binds the 30S subunit of the bacterial ribosome (Goldman et al. *Biochemistry* 22:359-368, 1983). Binding of the complex to the ribosome inhibits the binding of aminoacyl-tRNAs, resulting in inhibition of protein synthesis (Wissmann et al. *Forum Mikrobiol.* 292-99, 1998; Epe et al. *EMBO J.* 3:121-26, 1984). Tetracyclines have also been found to bind to the 40S subunit of eukaryotic ribosome; however, they do not achieve sufficient concentrations in eukaryotic cells to affect protein synthesis because they are not actively transported in eukaryotic cells (Epe et al. *FEBS Lett.* 213:443-47, 1987).

Structure-activity relationships for the tetracycline antibiotics have been determined empirically from 50 years of semi-synthetic modification of the parent structure (Sum et al. *Curr. Pharm. Design* 4:119-32, 1998). Permutations of the upper left-hand portion of the natural product, also known as the hydrophobic domain, have provided new therapeutically active agents, while modifications of the polar hydrophobic domain result in a loss of activity. However, semi-synthesis by its very nature has limited the number of tetracycline analogs that can be prepared and studied.

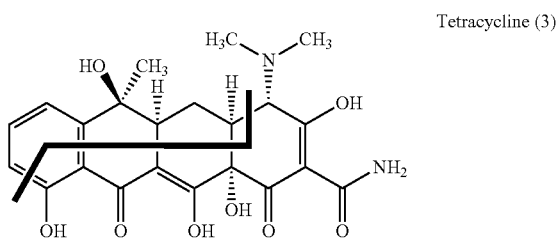

Tetracycline (3)

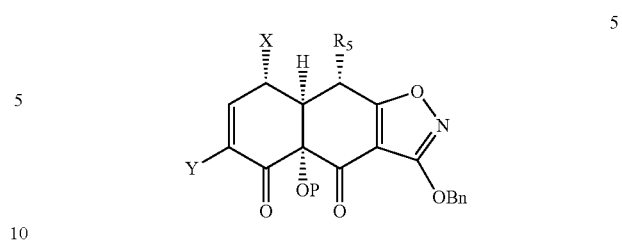

5

The tetracyclines are composed of four linearly fused six-membered rings with a high density of polar functionality and stereochemical complexity. Previous approaches to the synthesis of tetracyclines typically proceeded via a stepwise assembly of the tetracyclic ring system. In 1962, Woodward and co-workers reported the first total synthesis of racemic 6-desmethyl-6-deoxytetracycline (sancycline, 4), the simplest biologically active tetracycline (Conover et al. *J. Am. Chem. Soc.* 84:3222-24, 1962). The synthetic route was a remarkable achievement for the time and proceeded by the stepwise construction of the rings in a linear sequence of 22 steps (overall yield ~0.003%). The first enantioselective synthesis of (−)-tetracycline (3) from the A-ring precursor D-glucosamine (34 steps, 0.002% overall yield) was reported by Tatsuda and co-workers in 2000 (Tatsuta et al. *Chem. Lett.* 646-47, 2000). Other approaches to the synthesis of tetracycline antibiotics, which have also proceeded by the stepwise assembly of the ABCD ring system beginning with D or CD precursors, include the Shemyakin synthesis of (±)-12a-deoxy-5a,6-anhydrotetracycline (Gurevich et al. *Tetrahedron Lett.* 8:131, 1967; incorporated herein by reference) and the Muxfeldt synthesis of (±)-5-oxytetracycline (terramycin, 22 steps, 0.06% yield) (Muxfeldt et al. *J. Am. Chem. Soc.* 101:689, 1979; incorporated herein by reference). Due to the length and poor efficiency of the few existing routes to tetracyclines, which were never designed for synthetic variability, synthesis of tetracycline analogs is still limited.

Several approaches were developed to react the enone 5 with a toluate (6), benzylic halide, or benzocyclobutenol (8) to form the tetracycline core ring system. The first approach involves the reaction of the enone with an anion formed by the deprotonation of a toluate (6) or metallation of a benzylic halide as shown below.

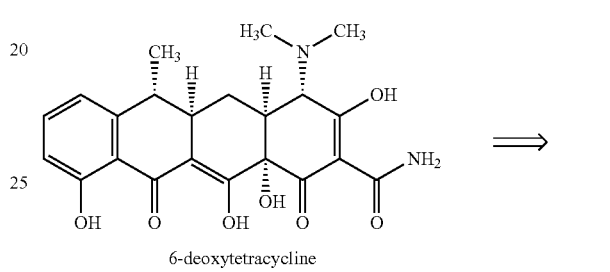

6-deoxytetracycline

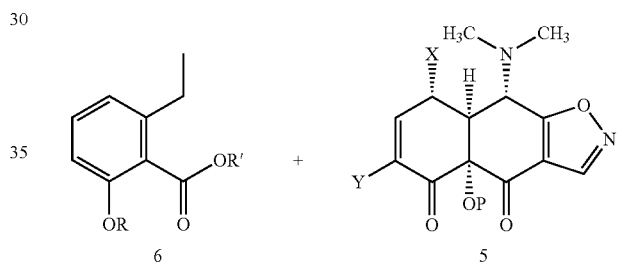

6-deoxytetracycline (4)

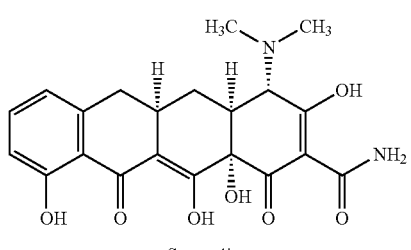

Sancycline

More recently, a novel convergent synthetic route to tetracyclines and various analogs, including pentacycline and heterocycle-containing tetracyclines, has been developed by Myers and co-workers. See US 2005/0282787, published Dec. 22, 2005; incorporated herein by reference; and Charest et al., *Science*, 308:395-398, 15 Apr. 2005; Charest et al., *J. Am. Chem. Soc.* 127:8292-93, 2005. This new route proceeds through the highly functionalized chiral enone intermediate (5) which is prepared starting from benzoic acid in ten steps (11% yield, >95% ee) (Charest et al., *Science* 308:395-398, Apr. 15, 2005; Charest et al., *J. Am. Chem. Soc.* 127:8292-8293, 2005; Myers et al., *Org. Lett.* 3(18):2923-26, 2001).

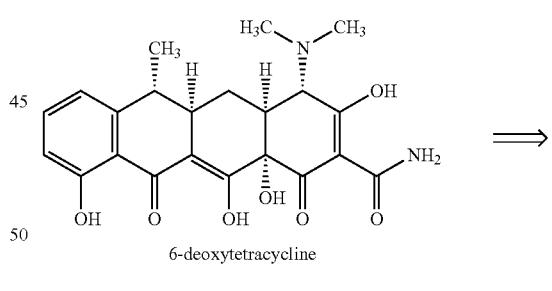

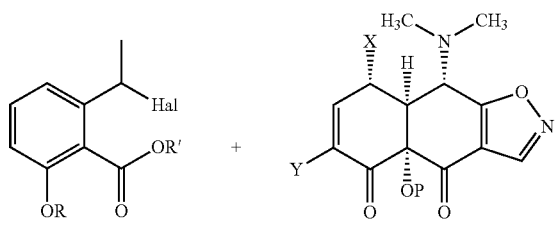

A second approach involves reacting the enone in a Diels-Alder-type reaction with a diene (7) or a benzocyclobutenol (8).

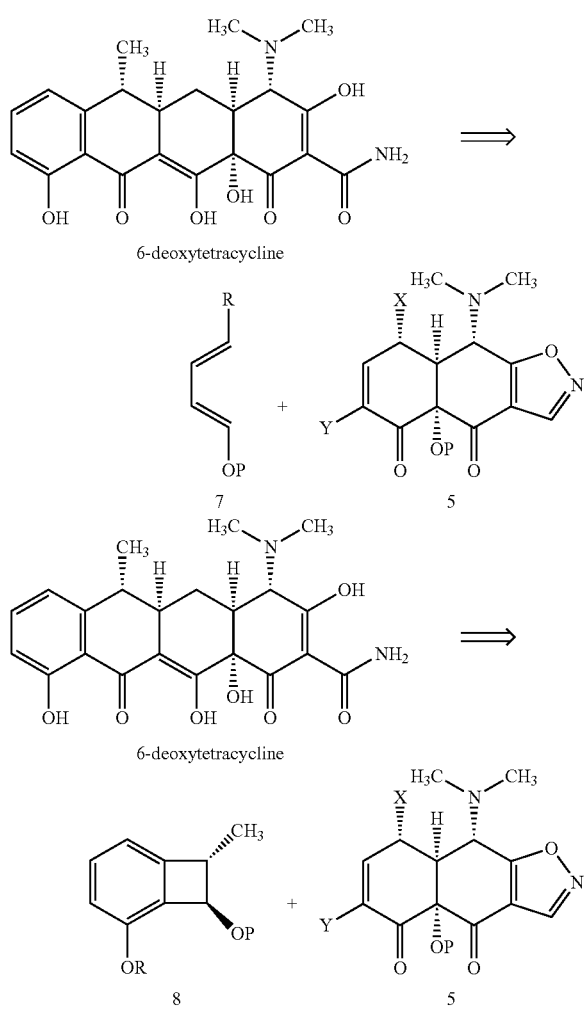

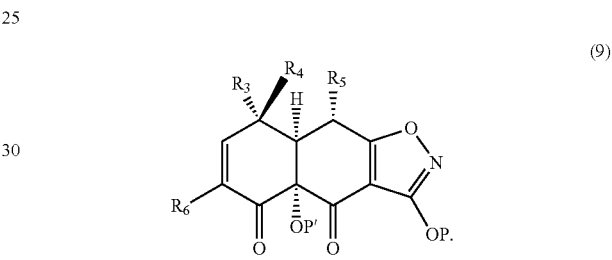

In these approaches, the chiral enone provides the functionalized A and B rings of the tetracycline core, and the D-ring is derived from the toluate (6), benzylic halide, or benzocyclobutenol (8). In bringing the two portions of the tetracycline core together the C-ring is formed, preferably in a stereoselective manner. These new synthetic approaches to tetracycline analogs not only allow for the stereoselective and efficient synthesis of a wide variety of tetracycline analogs never before prepared, but they also allow for preparation of tetracycline analogs in which the D-ring is replaced with a heterocycle, 5-membered ring, or other ring systems. The new methodologies also allow for the preparation of various pentacyclines or higher cyclines containing aromatic and non-aromatic carbocycles and heterocycles. See U.S. patent application, US2005/0282782, published Dec. 1, 2005; PCT Application WO 05/112985, published Dec. 1, 2005; and U.S. Provisional Patent Application, U.S. Ser. No. 60/790,413, filed Apr. 7, 2006; each of which is incorporated herein by reference.

Although the above approaches to tetracycline analogs are much more efficient than earlier approaches and allow for synthetic variability, there remains a need for improving the efficiency of this new route to tetracycline analogs. Specifically, any improvements in the multi-step synthesis of the chiral enone would significantly improve the overall efficiency of the synthesis of tetracycline analogs.

SUMMARY OF THE INVENTION

The present invention provides a novel synthetic approach to the functionalized chiral enone (9) useful in the synthesis of tetracycline analogs.

$$(9)$$

One exemplary synthesis of an enone of formula 9 is shown below. The synthesis begins with aldehyde 10 and in eight steps yields enone 18. Aldehyde 10 is coupled with a vinyl reagent to yield a mixture of enantiomers of the corresponding alcohol. Chiral resolution using amano lipase followed by substitution yields compound 13, which is subsequently metalated and reacted with 3-methoxyfurfural. In certain embodiments, rather than a chiral resolution of the racemate, the allylic alcohol is prepared by enantioselective addition of the vinyl group to the aldehyde 10. Intramolecular cyclization of 14 yields the bridged tricycle 15. The unprotected secondary hydroxyl group is then oxidized to the corresponding tricyclic ketone (16). Demethylation of 16 followed by rearrangement yields the enone 17, the free hydroxyl of which may be optionally protected to yield enone 18.

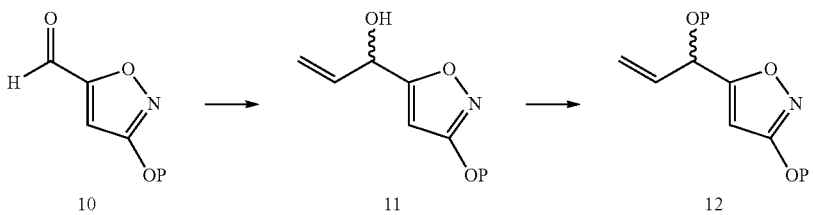

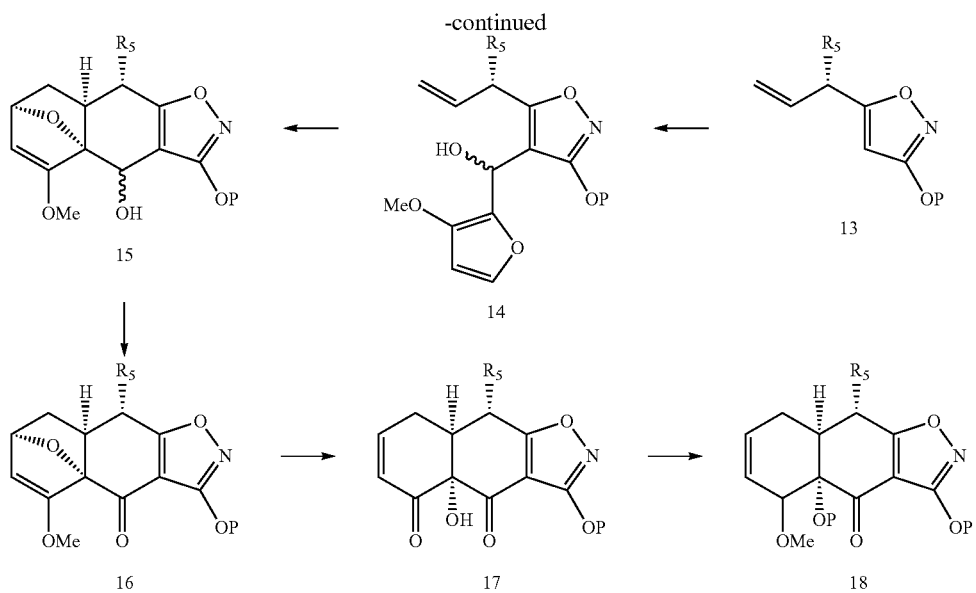

As would be appreciated by one of skill in the art, various substitutions, derivatives, and modifications of the starting materials, intermediates, reagents, and synthetic methodology may be used to prepare enone 17 or derivatives thereof, enone 18 or derivatives thereof, or any other enone of formula 9 without departing from the present invention.

For example, in certain embodiments, the coupling of the isoxazole to 3-methyoxyfurfural to prepare compound 14 may be achieved by a metal-halogen exchange reaction, rather than low-temperature metalation, using a derivative of 13 of the formula:

wherein X is a halogen (e.g., iodine or bromine). Bromination of the isoxazole ring to give the brominated aldehyde followed by enantioselective addition of a vinyl moiety using divinyl zinc is shown in the scheme below:

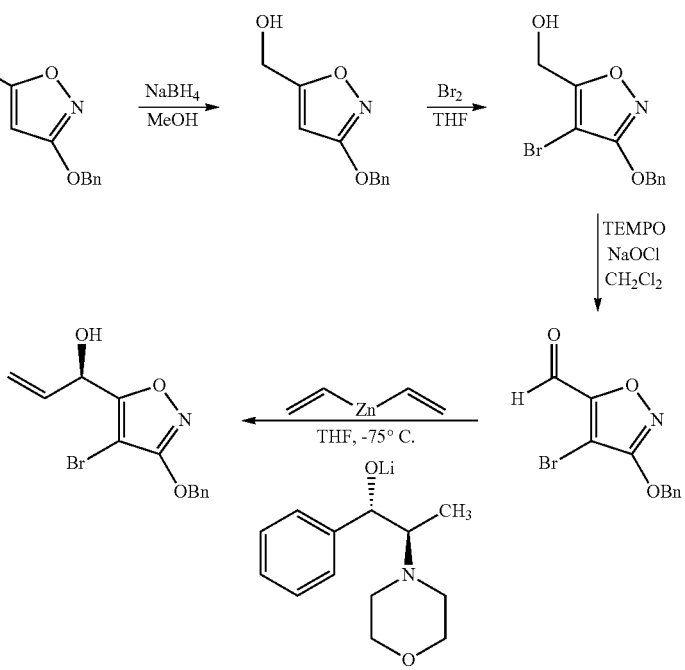

The present invention includes individual steps (e.g., reduction, protection, de-protection, chiral resolution, metalation, rearrangement, de-methylation, etc.) in the synthesis of an enone of formula 9 as well as any combination of steps in the synthetic scheme. The inventive synthesis allows for the production of multi-gram quantities of the final product. In certain embodiments, the synthesis may provide at least 50 g of the desired enone.

In another aspect, the invention provides various useful intermediates in the synthetic scheme leading to enones of the formula 18. Particularly useful intermediates include compounds of the formula:

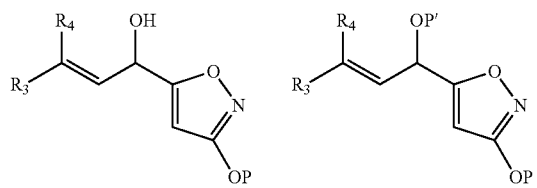

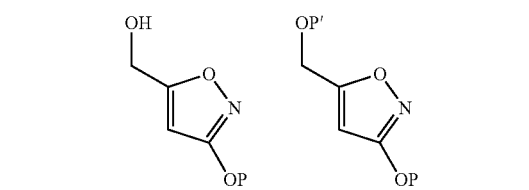

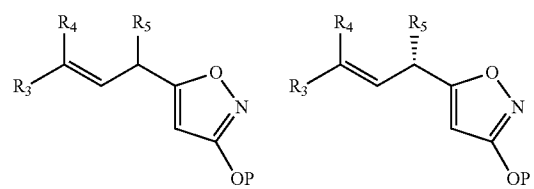

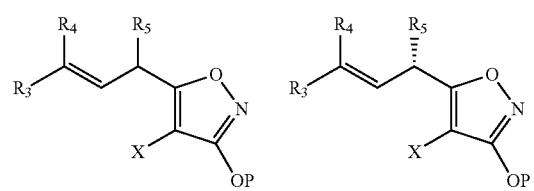

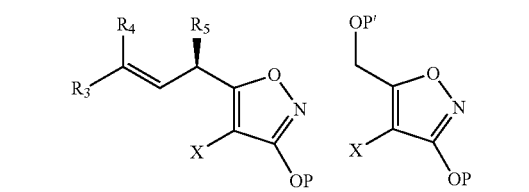

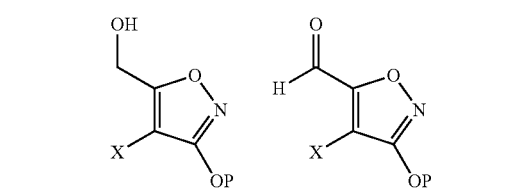

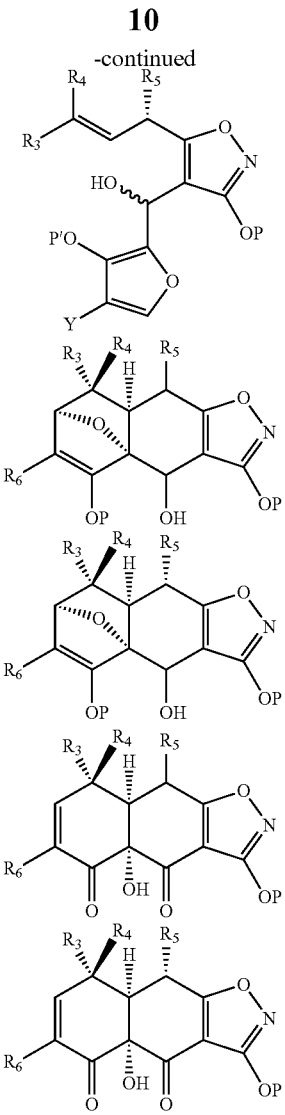

or salts, stereoisomers, enantiomers, diastereomers, tautomers, or protected or unprotected forms of the intermediates. The various intermediates with chiral centers are provided in enantiomeric or diastereomeric pure form or are provided as a mixture of stereoisomers.

The present invention also provides the synthesis of tetracycline analogs using the synthetic methodology for preparing the enone (9), described herein. In certain embodiments, a chiral enone (9) prepared by the methodology described herein is used in combination with the methodologies described in US 2005/0292787, which is incorporated herein by reference, to prepare a tetracycline analog. In certain embodiments, the inventive synthesis of the enone intermediate is used to synthesize any compound described in U.S. patent application, US2005/0282787, published Dec. 22, 2005; international PCT application, WO 05/112945, published Dec. 1, 2005; U.S. provisional patent application, U.S. Ser. No. 60/790,413, filed Apr. 7, 2006; or international PCT application, US07/66253, filed Apr. 6, 2007; each of which is incorporated herein by reference. The inventive methods and intermediates may also be used to prepare tetracyclines or tetracycline analogs known in the art (e.g., doxycycline, sancycline, minocycline, tigecycline, tetracycline, etc.). The new synthetic approach to the enone intermediate is particularly useful in preparing 6-deoxytetracyclines. The new synthetic methodology and intermediates are also useful in preparing 6-hydroxytetracyclines, pentacyclines, hexacyclines, C5-substituted tetracyclines, C5-unsubstituted tetracyclines, tetracyclines with heterocyclic D-rings, and other tetracycline analogs. As would be appreciated by one of skill in this art, the new synthesis of enone (9) is also useful in preparing other organic compounds which may or may not be related to tetracyclines.

In certain embodiments, the invention provides several basic approaches to the synthesis of tetracycline analogs using the synthesis described herein for preparing the enone intermediate. The first approach to preparing tetracycline analogs involves reaction of the enone with an anion formed by the deprotonation of a toluate or metalation of a benzylic halide. The deprotonation of a toluate is particularly useful in preparing 6-deoxytetracyclines with or without a C5-substituent. The metalation (e.g., metal-halogen exchange (e.g., lithium-halogen exchange), metal-metalloid exchange (e.g., lithium-metalloid exchange)) is particularly useful in preparing 6-deoxytetracyclines with or without a C5-substituent as well as pentacyclines. The second approach to preparing tetracycline analogs involves reacting the enone intermediate, as prepared by the inventive methodology, in a Diels-Alder-type reaction with a diene or a benzocyclobutenol. In both of these approaches, the chiral enone provides the functionalized A and B rings of the tetracycline core, and the D-ring is derived from the toluate, benzylic halide, or benzocyclobutenol. In bringing these two portions of the molecule together the C-ring is formed. In certain embodiments, the C-ring is formed in a stereoselective manner. These approaches not only allow for the stereoselective and efficient synthesis of a wide variety of tetracycline analogs, but they also allow for the efficient preparation of tetracycline analogs in which the D-ring is replaced with a heterocycle, 5-membered ring, or other ring system. They also allow the preparation of various pentacyclines or higher cyclines containing aromatic and non-aromatic carbocycles and heterocycles. These approaches also allow for the preparation of various tricyclines.

In certain embodiments, the inventive intermediates (e.g., enone, derivatives of enone, dicyclines) have biological activity. For example, an intermediate may possess anti-microbial or anti-proliferative activity. In another aspect, the present invention provides methods of treatment and pharmaceutical compositions including the novel compounds of the present invention. The pharmaceutical compositions may optionally include a pharmaceutically acceptable excipient. The methods and pharmaceutical compositions may be used to treat any infection including cholera, influenza, bronchitis, acne, malaria, urinary tract infections, sexually transmitted diseases including syphilis and gonorrhea, Legionnaires' disease, Lyme disease, Rocky Mountain spotted fever, Q fever, typhus, bubonic plague, gas gangrene, hospital acquired infections, leptospirosis, whooping cough, and anthrax. In certain embodiments, the infections are caused by tetracycline-resistant organisms. In certain instances, the compounds of the invention exhibit anti-neoplastic or anti-proliferative activity, in which case the compounds may be useful in the treatment of diseases such as cancer, autoimmune diseases, inflammatory diseases, and diabetic retinopathy. The methods and compositions may be used to treat disease in humans and other animals including domesticated animals. Any mode of administration including oral and parenteral administration of a pharmaceutical composition comprising an inventive compound may be used.

Given the versatility and efficiency of the synthesis of tetracycline analogs using the enone (9) as an intermediate, the present invention represents an improvement in the overall synthetic approach to tetracycline analogs. The present invention allows for the preparation of tetracycline analogs in higher yields than previously attainable. The new synthetic approach to the enone intermediate also makes the synthesis of tetracycline analogs more amenable to large-scale production given its improved overall yield.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof, as falling within the scope of the invention. Additional asymmetric carbon atoms may be present in a substituent such as an aliphatic (e.g., alkyl) or heteroaliphatic group. All such isomers, as well as mixtures thereof, are considered to be within this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl) diphenylmethyl, 4,4',4''-tris(4,5-dichlorophthalimidophenyl) methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidene ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo) fluorenylmethyl carbamate, 9-(2,7-dibromo)fluoroenylmethyl carbamate, 2,7-di-t-butyl-[9-(10,10-dioxo-10,10,10, 10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N- dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), f3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. In certain embodiments, only one hydrogen radical in a given structure is replaced with the radical of a specified substituent. In other embodiments, one, two, or three hydrogen radicals in a given structure are replaced with the same or different radicals of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 aliphatic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like. The term "dialkylamino" refers to a group having the structure —NRR', wherein R and R' are each an aliphatic group, as defined herein. R and R' may be the same or different in an dialkylamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments, hydrogen atoms in the compound are replaced with deuterium atoms (2H) to slow the degradation of compound in vivo. Due to isotope effects, enzymatic degradation of the deuterated tetracyclines may be slowed thereby increasing the half-life of the compound in vivo. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (see Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Tautomers": As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Any animal may be administered a tetracycline analog for the treatment of disease. Preferably, the non-human animal is a mammal (e.g., a rodent, a mouse, a rat, a rabbit, a monkey, a dog, a cat, a primate, or a pig). A non-human animal may be a transgenic animal. In certain embodiments, the animal is human.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Effective amount": In general, the "effective amount" of an active agent or the microparticles refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a tetracycline analog antibiotic is the amount that results in a sufficient concentration at the site of the infection to kill the microorganism causing the infection (bacteriocidal) or to inhibit the reproduction of such microorganisms (bacteriostatic). In another example, the effective amount of tetracycline analog antibiotic is the amount sufficient to reverse clinical signs and symptoms of the infection, including fever, redness, warmth, pain, chills, cultures, and pus production.

"Tetracycline analog": The term, "tetracycline analog," as referred to herein refers to any compound prepared using the inventive methodology. Tetracycline analogs are typically compounds that can be prepared using the enone (9) as an intermediate in the synthesis. Tetracycline analogs include dicylines, tricyclines, tetracyclines, pentacyclines, hexacyclines, or higher. In certain embodiments, the ring system may contain heterocycles. In certain embodiments, the ring system may contain three-membered rings, four-membered rings, five-membered rings, six-membered rings, seven-membered rings, or higher. In certain embodiments, the tetracycline analogs is a 6-deoxytetracycline. In other embodiments, the tetracycline analog is a 6-hydroxytetracycline. In other embodiments, the tetracycline analog is a pentacycline. In other embodiments, the tetracycline analog is a C5-substituted tetracycline. In yet other embodiments, the tetracycline analog is a C5-unsubstituted tetracycline. In certain embodiments, the tetracycline analogs have biological activity such as anti-microbial activity or anti-proliferative activity.

DETAILED DESCRIPTION OF CERTAIN EMBODIMENTS OF THE INVENTION

Figure 1:
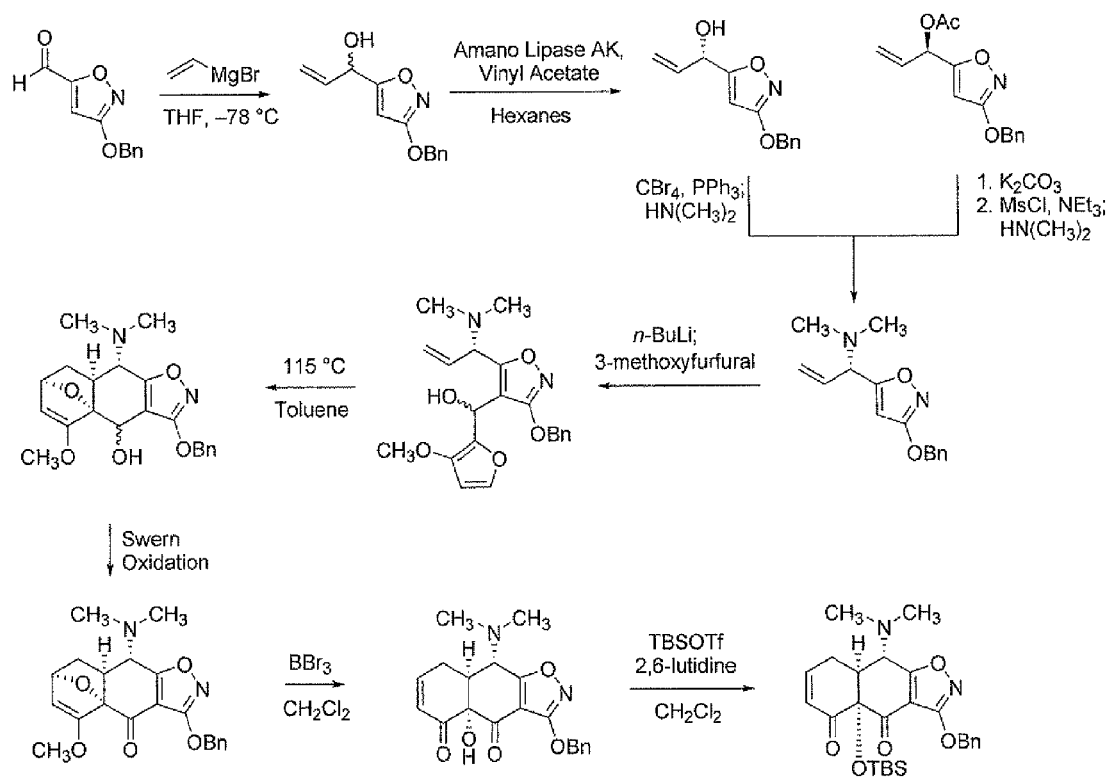
FIG. 1 shows an exemplary synthesis of a particular chiral enone useful in the synthesis of tetracycline analogs.
Figure 2:
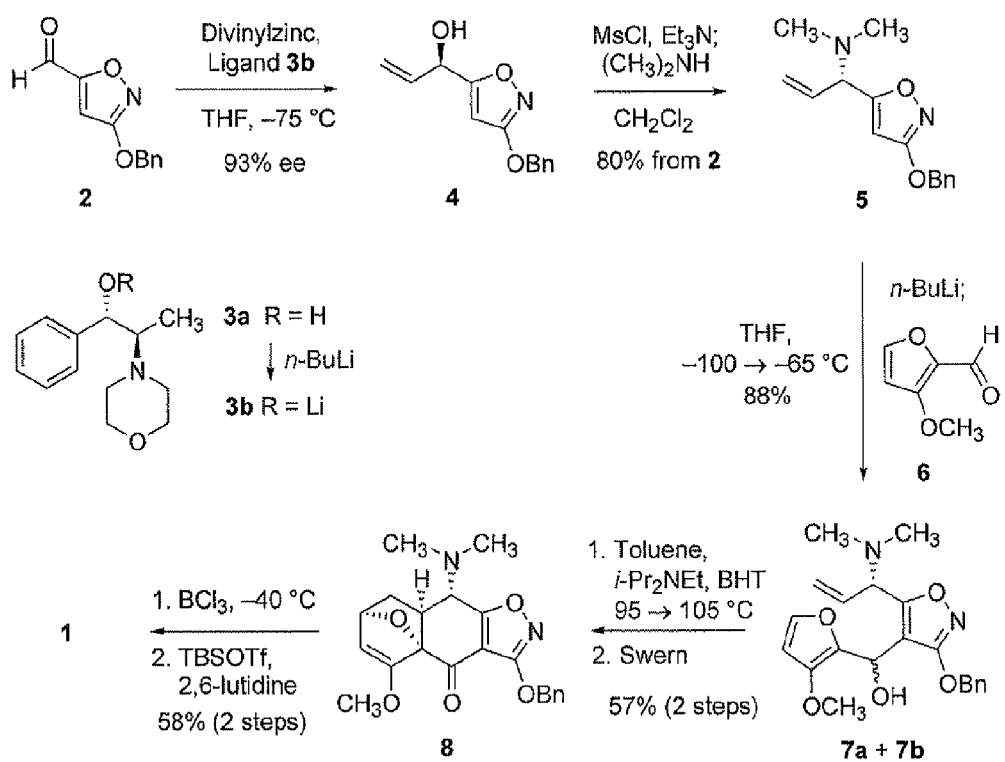
FIG. 2 shows another exemplary synthesis of a chiral enone useful in the synthesis of tetracycline analogs. The synthesis includes the enantioselective addition of a vinyl moiety to produce the chiral allylic alcohol 4 rather than resolution of a racemate. The synthesis is also noteworthy for the use of boron trichloride at −40° C. in the ring-opening step resulting in enone 1

The present invention provides a synthetic strategy for the synthesis of an intermediate useful in the synthesis of tetracycline analogs. The highly functionalized chiral enone 9 is as shown below:

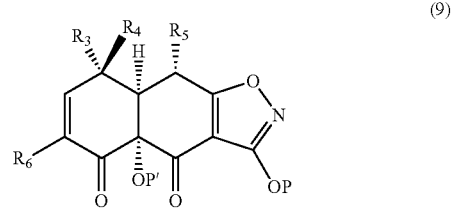

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O (taken with $R_4$); —C(=O)$R_C$; —CO$_2R_C$; —CN; —SCN; —$SR_C$; —$SOR_C$; —$SO_2R_C$; —$NO_2$; —N($R_C$)$_2$; —NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —C(=O)$R_D$; —CO$_2R_D$; —CN; —SCN; —$SR_D$; —$SOR_D$; —$SO_2R_D$; —$NO_2$; —N($R_D$)$_2$; —NHC(O)$R_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R₅ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_E$; —C(=O)R$_E$; —CO$_2$R$_E$; —CN; —SCN; —SR$_E$; —SOR$_E$; —SO$_2$R$_E$; —NO$_2$; —N(R$_E$)$_2$; —NHC(O)R$_E$; or —C(R$_E$)$_3$; wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is selected from the group consisting of hydrogen, halogen, substituted or unsubstituted aliphatic, substituted or unsubstituted heteroaliphatic, substituted or unsubstituted alkoxy, —OR$_F$, —CN, —SCN, —SR$_F$, alkylthio, arylthio, —NO$_2$, amino, —N(R$_F$)$_2$, and —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is independently selected from the group consisting of hydrogen or a protecting group;

P' is independently selected from the group consisting of hydrogen or a protecting group; and salts, stereoisomers, tautomers, enantiomers, diastereomers, and derivatives thereof. The new route to this enone is more efficient than previously reported routes. Therefore, this new strategy is an improvement to the convergent synthesis of tetracycline analogs using this intermediate. The chiral enone 9 can be reacted with anions of phthalides, anions of toluates, benzocyclobutenole, or dienes to yield tetracycline analogs including heterocyclic tetracyclines, dicyclines, tricyclines, pentacyclines, heterocyclic pentacyclines, hexacyclines, heterocyclic hexacyclines, polycyclines, and heterocyclic polycyclines.

Synthetic Methodology

The present invention provides all steps, methodologies, intermediates, and reagents useful in preparing the enone (9) along the synthetic route. The present invention provides for use of this methodology in the modular synthesis of tetracycline analogs by joining the highly functionalized chiral enone, which will become the A- and B-rings of the tetracycline core, with a molecule which will become the D-ring of the tetracycline core. The joining of these two intermediates results in the formation of the C-ring, preferably in an enantioselective manner. This methodology also allows for the synthesis of pentacyclines, hexacyclines, or higher ring systems as well as the incorporation of heterocycles into the ring system. In particular, the joining of these two fragments includes various nucleophilic addition reactions and cycloaddition reactions with enone (9) as described above and in U.S. patent application US2005/0282787, published Dec. 22, 2005.

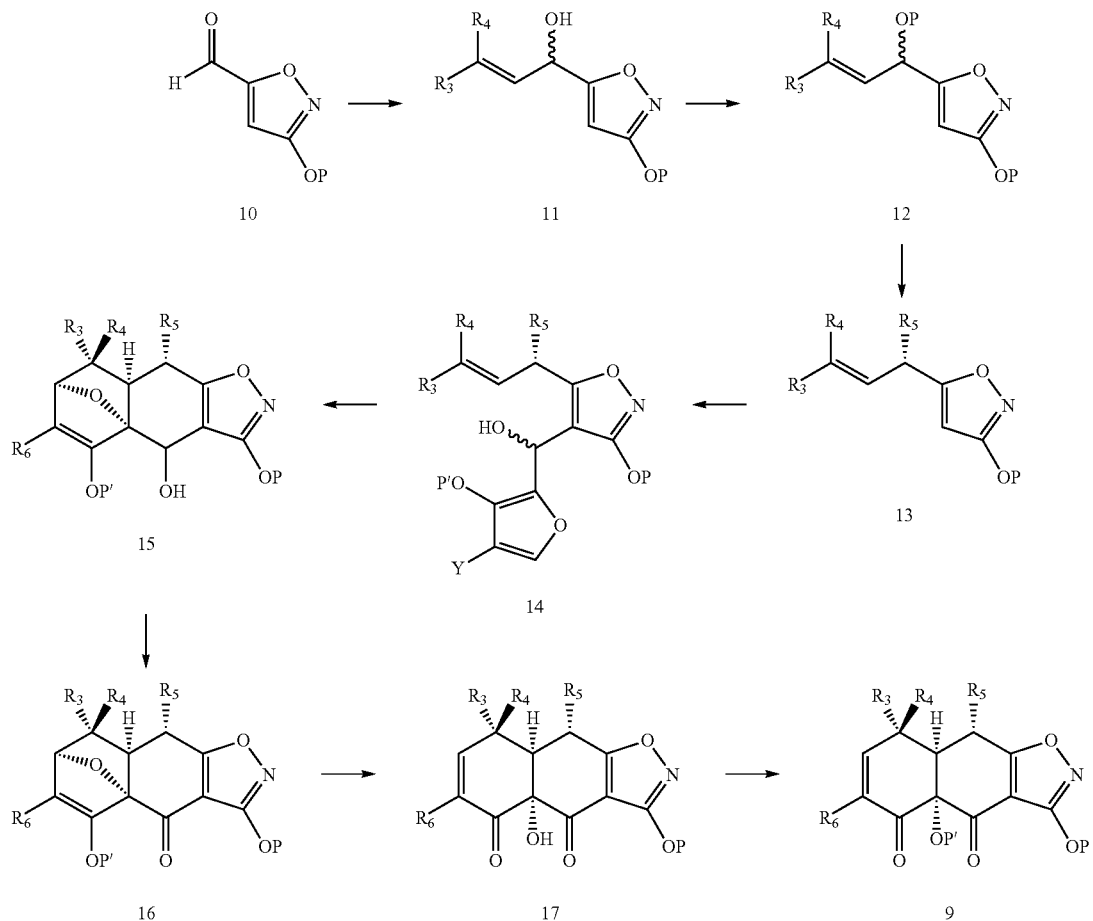

The synthesis of enone (9) begins with the aldehyde (10). The aldehyde moiety is reduced by the addition of a vinyl moiety or substituted vinyl moiety. The addition of the vinyl moiety is accomplished with any vinyl reagent. In certain embodiments, a metal vinyl reagent is used in the reaction. In certain embodiments, the metal vinyl reagent is of the formula:

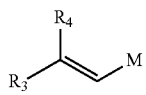

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and M is a metal-containing moiety (e.g., Zn, Cu, MgCl, MgBr, Li, Sn, etc.). In certain embodiments, M is MgBr. In other embodiments, M is MgCl. In other embodiments, M is Li. In certain embodiments, M is Zn. In certain embodiments, M is Zn with a chiral ligand. In certain embodiments, $R_3$ is hydrogen. In certain embodiments, $R_3$ is fluorine. In certain embodiments, $R_3$ is $C_1$-$C_6$ alkoxy. In certain embodiments, $R_3$ is protected hydroxy. In other embodiments, $R_3$ is $C_1$-$C_6$ alkyl. In certain embodiments, $R_4$ is hydrogen. In certain embodiments, $R_4$ is fluorine. In certain embodiments, $R_4$ is $C_1$-$C_6$ alkoxy. In certain embodiments, $R_4$ is protected hydroxy. In other embodiments, $R_4$ is $C_1$-$C_6$ alkyl. In certain embodiments, one of $R_3$ and $R_4$ is hydrogen. In other embodiments, both $R_3$ and $R_4$ are hydrogen. In certain particular embodiments, both $R_3$ and $R_4$ are hydrogen, and M is MgBr. In certain embodiments, the metal vinyl reagent is divinyl zinc. In certain particular embodiments, the metal vinyl reagent is divinyl zinc with a chiral ligand.

In certain embodiments, the reduction step is stereoselective yielding only one or substantially one enantiomer. In certain embodiments, the enantioselective reaction results in an an enantiomeric excess (ee) of at least 80%, at least 90%, at least 95%, at least 98%, or at least 99%. In certain embodiments, the addition of the vinyl moiety is acid catalyzed, for example, Lewis acid catalyzed. In certain particular embodiments, a Grignard reagent is used in the reaction. In other embodiments, a vinyl lithium reagent is used in the reaction. In certain embodiments, a vinyl zinc reagent is used in the reaction. In certain embodiments, the reduction step is enantioselective by addition of divinyl zinc with a chiral ligand. In certain embodiments, the chiral ligand used is an amino-alcohol ligand of formula:

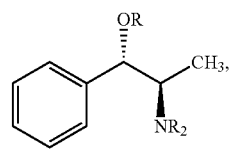

wherein each occurrence of R is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; or substituted or unsubstituted, branched or unbranched heteroaryl; and the two occurrences of R may optionally form a heterocyclic moiety. In certain embodiments, each occurrence of R is hydrogen or $C_1$-$C_6$ alkyl. In certain embodiments, each occurrence of R is $C_1$-$C_6$ alkyl. In certain embodiments, the two occurrences of R for a heterocyclic moiety. In certain embodiments, both R are methyl. In certain embodiments, $NR_2$ forms a pyrrolidine moiety. In certain embodiments, the two occurrences of R for a heteroaryl moiety. In certain embodiments, the chiral ligand used is an amino-alcohol ligand of formula:

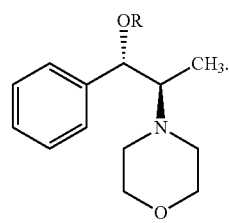

In certain embodiments, the aldehyde 10 is reduced by a metal reagent with a moiety that is subsequently converted into a alkenyl group as show in compound 11. The alkenyl moiety may result from an elimination reaction, reduction of an alkyne, deoxygenation of an epoxide, Wittig-type reaction, metathesis reaction, etc.

In the case of a non-stereospecific addition of the vinyl moiety, the two enantiomers produced may be separated. Any technique known in the art may be used to separate the enantiomers (e.g., crystallization, chiral chromatography, conversion to a diastereomer followed by conventional purification techniques, chiral resolution using an enzyme, chiral resolution via diastereomeric salt crystallization, etc.). In certain embodiments, a chiral resolution is used. In certain embodiments, a lipase-catalyzed chiral resolution is used. The lipase selectively acetylates one enantiomer versus the other. In certain embodiments, Amano Lipase AK in the presence of vinyl acetate is used to acetylate preferentially the (R)-enantiomer. The resulting products (i.e., free alcohol versus acetylated alcohol) are then separated using any purification method known in the art. In other embodiments, chiral chromatography is used to separate the enantiomers of 11. In yet other embodiments, a particular enantiomer is crystallized, optionally with a chiral salt as a diastereomeric salt.

The resulting (S)-isomer is reacted with a nucleophile to preserve the stereochemistry at the chiral center and yield compound 13. In certain embodiments, two substitution reactions based on an $S_N2$ mechanism are used in sequence to preserve the overall stereochemistry at the chiral center. For example, the allylic alcohol is converted to the corresponding bromide with $CBr_4$ and $PPh_3$ via an $S_N2$ mechanism, thereby inverting the stereochemistry at the chiral center. In other embodiments, the reaction is accomplished using N-chlorosuccinimide (NCS) or N-bromosuccinimide (NBS) and methyl sulfide. Other reactions for the formation of alkyl halides from allylic alcohols may also be used. See, e.g., March's Advanced Organic Chemistry $5^{th}$ Ed., pp. 518-19; incorporated herein by reference. Preferably ones that result in an inversion of stereochemistry at the chiral center are used. The resulting allylic bromide or other halide or leaving group is then reacted with a nucleophile (e.g., amine, a dialkylamine, a monoalkylamine, alcohol, alkoxide, thiol, etc.) to yield 13. In certain embodiments, the reaction conditions of the second substitution reaction also favor an $S_N2$ reaction so that the stereochemistry at the chiral center is inverted again, thus preserving the overall stereochemistry. As would be appreciated by one of skill in this art, the nucleophile, leaving group, reagents, solvent, concentration of reagents, temperature, time of reaction, etc. in the above reactions may be adjusted to favor the desired stereochemical outcome, to improve the yield, and/or to adjust other aspects of the reaction.

In contrast, the (R)-isomer is simply reacted with a nucleophile under reaction conditions that favor an $S_N2$ mechanism in order to invert the stereochemistry at the chiral center. In certain embodiments, the alcohol is first converted into a better leaving group (e.g., by forming the corresponding tosylate, mesylate) before reaction with the nucleophile. As would be appreciated by one of skill in this art, the nucleophile, leaving group, reagents, solvent, concentration of reagents, temperature, time of reaction, etc. in the above reaction may be adjusted to favor the desired stereochemical outcome and/or to improve the yield.

In certain embodiments, the stereochemistry is preferably as shown in isoxazole 13 of formula:

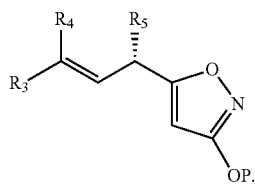

In certain embodiments, $R_5$ is $-N(R_E)_2$. In certain embodiments, $R_5$ is $-N(R_E)_2$, wherein $R_E$ is $C_1$-$C_6$alkyl. In certain particular embodiments, $R_5$ is $-N(CH_3)_2$. In other embodiments, $R_5$ is $-OR_E$. In certain particular embodiments, $R_5$ is $-OCH_3$. In yet other embodiments, $R_5$ is $-SR_E$. In certain particular embodiments, $R_5$ is $-SCH_3$. In certain embodiments, $R_5$ is acyl. In other embodiments, $R_5$ is substituted or unsubstituted aliphatic or heteroaliphatic. In certain embodiments, $R_5$ is $-CN$, $-NO_2$, or halogen.

In other embodiments, the opposite stereochemistry of 13, that is,

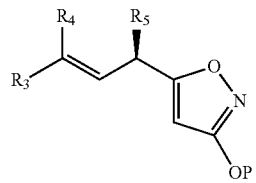

may be desired and produced by modifying the above methodology.

In certain embodiments, isoxazole 13, whether of the (R)- or (S)-configuration, is an enantiomerically pure compound. In other embodiments, isoxazole 13 is at least 80%, 90%, 95%, 98%, or 99% enantiomerically pure. Rather than purifying or resolving the enantiomers of the alcohol in the previous step, it will be appreciated that the purification of the enantiomers may take place after the preparation of isoxazole 13. Again, this separation of two enantiomers may be accomplished by any technique known in the art including, but not limited to, crystallization, chiral chromatography, conversion to a diastereomer followed by conventional purification techniques, chiral resolution using an enzyme, and chiral resolution via diastereomeric salt crystallization.

In still other embodiments, the preparation of isoxazole 13 is not stereoselective. In certain embodiments, the desired stereoisomer is separated from the undesired stereoisomer. The undesired stereoisomer may be discarded or converted into the desired stereoisomer or another intermediate useful in the synthesis. In certain embodiments, the undesired stereoisomer is converted into the desired stereoisomer.

In the next step of the synthesis of the enone, isoxazole 13 is metalated and reacted with 3-methoxyfurfural or another substituted furfural moiety. Preferably, the furfural moiety has a protected hydroxyl group at C-3. In certain embodiments, an at least 90% enantiomerically pure mixture of isoxazole 13 is used in this reaction. In other embodiments, isoxazole 13 is at least 95%, 98%, or 99% enantiomerically pure. In certain embodiments, isoxazole 13 is reacted with n-butyl lithium, another organolithium reagent, or another metal reagent. In certain embodiments, a 3-substituted 3-alkoxyfurfural or a 4-substituted 3-alkoxyfurfural is used in the reaction. In certain embodiments, the furfural is a 2- or 4-substituted 3-methoxyfurfural. In certain embodiments, the furfural moiety is of the formula:

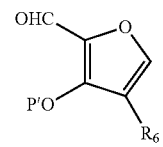

wherein $R_6$ is selected from the group consisting of hydrogen, halogen, substituted or unsubstituted aliphatic, substituted or unsubstituted heteroaliphatic, substituted or unsubstituted alkoxy, $-OR_F$, $-CN$, $-SCN$, $-SR_F$, alkylthio, arylthio, $-NO_2$, amino, $-N(R_F)_2$, and $-C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy;

alkylthio; arylthio; amino, alkylamino, dialkylamino, heteroaryloxy; or heteroarylthio moiety; and P is independently selected from the group consisting of hydrogen or a protecting group. In certain embodiments, P' is $C_1$-$C_6$ alkyl. In certain particular embodiments, P' is methyl. In certain embodiments, P' is a silicon-containing protecting group (e.g., TBDMS, TMS, TES, etc.). In certain embodiments, P' is hydrogen. In certain embodiments, P' is acyl. In certain particular embodiments, P' is acetyl. In certain embodiments, $R_6$ is hydrogen. In other embodiments, $R_6$ is $C_1$-$C_6$ alkyl. In certain embodiments, $R_6$ is —$OR_F$. In yet other embodiments, $R_6$ is —$N(R_F)_2$.

Alternatively, the coupling of the isoxazole to the furfural moiety may be achieved using a metal-halogen exchange reaction. In such embodiments, an isoxazole of formula:

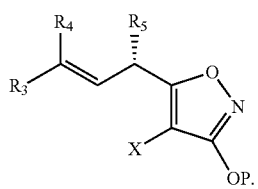

(13a)

wherein $R_3$, $R_4$, $R_5$, and P are as defined herein; and X is a halogen, is used. In certain embodiments, X is bromine. In other embodiments, X is iodine. In certain embodiments, a magnesium-halogen exchange is used. For example, isoxazole 13a is reacted with i-PrMgCl and then allowed to react with the furfural moiety as described above. In certain embodiments, the reaction is performed at approximately 0° C.--20° C. in THF or another suitable solvent. Such a magnesium-halogen exchange reaction eliminates the need for using highly reactive lithium reagents. As would be appreciated by one of skill in the art, other metal-halogen exchange reactions may be used to produce 14 such as a lithium-halogen exchange reaction.

The isoxazole of formula 13a may be prepared by direct electrophilic halogenation (e.g., iodination, bromination) of the alcohol of formula:

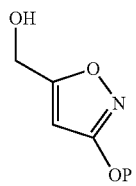

wherein P is hydrogen or an oxygen protecting group, to yield a halogenated isoxazole of formula:

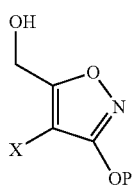

wherein P is defined above, and X is a halogen (e.g., Br, I). Subsequent oxidation of the primary alcohol (for example, using TEMPO, NaOCl, $CH_2Cl_2$) followed by addition of a vinyl moiety yields the bromo allylic alcohol of formula:

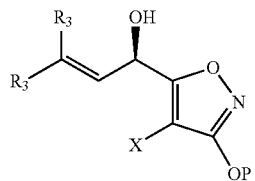

wherein $R_3$, $R_4$, P, and X are defined herein. In certain embodiments, the addition of the vinyl moiety is enantioselective. In certain embodiments, the enantioselective addition of the vinyl group is accomplished using divinyl zinc and a chiral aminoalcohol ligand. Other suitable chiral aminoalcohols are described herein. In certain embodiments, the chiral ligand used is an amino-alcohol ligand of formula:

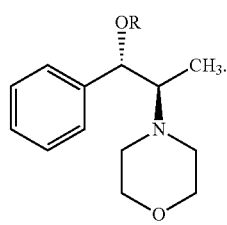

The bromo allylic alcohol, or corresponding mesylate or other suitable leaving group, is then displaced to provide:

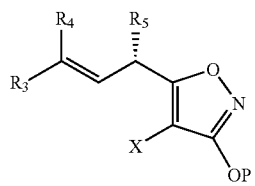

wherein $R_3$, $R_4$, $R_5$, P, and X are defined herein. Various conditions and reagents useful in such a substitution reaction, particularly $S_N2$ reactions, are described herein.

Intramolecular Diels-Alder of 14 yields the bridged tricyclic product 15. In certain embodiments, the Diels-Alder reaction is stereoselective and regioselective yielding only the stereoisomer and regioisomer shown. In other embodiments, the desired stereoisomer is at least 80%, 90%, 90%, 98%, or 99% of the product. The desired product is optionally separated from an undesired product or starting material at this stage. The Diels-Alder reaction is catalyzed or uncatalyzed. In certain embodiments, the reaction is uncatalyzed. In certain embodiments, the reaction is catalyzed with a Lewis acid catalyst. In certain embodiments, the reaction is caused by heating the starting material 14. In certain embodiments, the compound is heated to a temperature above 60° C., 70° C., 80° C., 90°, 100° C., 110° C., or 120° C. In certain particular embodiments, compound 13 is heated to approximately 115° C. in an organic solvent such as toluene. Much is known in the art regarding the Diels-Alder reaction. See *March's Advanced Organic Chemistry*, 5th Ed., pp. 1062-75. As would be appreciated by one of skill in the art, the reaction conditions may be optimized for different substitutions on the starting material 14.

After formation of the bridged tricycle 15, the free alcohol is oxidized to the corresponding ketone. Any method known in the art for oxidizing a secondary alcohol may be used. Secondary alcohols may be oxidized to the corresponding ketone using oxidizing agents, dehydrogenation, or hypervalent iodine reagents (e.g., Dess-Martin periodinane). In general, milder oxidizing reagents are used. In certain embodiments, a Swern oxidation is used. In certain embodiments, tetrapropylammonium perruthenate (TPAP)/N-methylmorpholine-N-oxide (NMO) is used as the oxidizing agent. In certain other embodiments, the free alcohol is protected with an oxygen protecting group rather than oxidizing it to the corresponding ketone. Any oxygen protecting group may be used including silicon-containing protecting groups.

The next step involves the removal of the oxygen protecting group P' and rearrangement of the resulting enolate to form the enone 17. The reaction conditions used to remove the protecting group will depend on the particular protecting group being used to mask the enolate. In certain embodiments, P' is methyl or another alkyl group. Removal of the methyl group with a Lewis acid results in rearrangement of the resulting enolate. In certain embodiments, the demethylation reaction is performed using $BBr_3$. The reaction with $BBr_3$ is typically performed at approximately −78° C. In certain other embodiments, the demethylation reaction is performed using $BCl_3$. The reaction with $BCl_3$ is typically performed at approximately −40° C. One advantage of using $BCl_3$ is that it can be used at a higher temperature than $BBr_3$. As would be appreciated by one of skill in the art, other protecting groups can be removed under conditions suitable to selectively remove P' and not affect other functional groups of the enone.

The resulting free hydroxyl group of enone 17 is then optionally protected to yield enone 9. The protecting group can be any oxygen protecting group. In certain embodiments, the oxygen protecting group is a silicon-containing protecting group. In certain particular embodiments, the oxygen protecting group is TBS.

As would be appreciated by one of skill in the art, each of the steps in the synthesis of the enone may be optionally followed by the appropriate work-up and purification of the desired product. Certain steps, however, may not require purification before being used as starting material in the next reaction. The inventive synthesis of the enone may be used to prepare multi-gram quantities. In certain embodiments, at least 25 grams of the enone is prepared. In other embodiments, at least 50 grams of the enone is prepared using the inventive synthesis. In certain other embodiments, at least 100 grams of the enone is prepared.

The enone (9) is then optionally reacted with an anion of a phthalide, an anion of a toluate, a benzocyclobutenole, or a diene to yield a tetracycline analog. Details of these reactions and possible phthalides, toluates, benzocyclobutenoles, and dienes are described in U.S. patent application US 2005/0282787, published Dec. 22, 2005; WO 05/112945, published on Dec. 1, 2005; and U.S. provisional patent application, U.S. Ser. No. 60/790,413, filed Apr. 7, 2006.

In one embodiment, enone (9) is reacted with an anion resulting from the deprotonation of toluate (6). The toluate of formula:

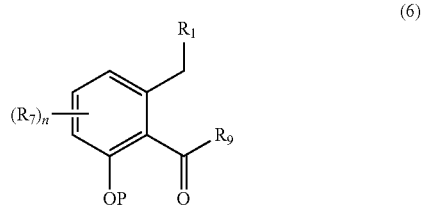

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —N($R_G$)$_2$; —NHC(O)$R_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and n is an integer in the range of 0 to 3, inclusive;

$R_9$ is —$OR_I$; —CN; —SCN; —$SR_I$; or —N($R_I$)$_2$; wherein each occurrence of $R_I$ is independently a hydrogen, a protecting group; a cyclic or acyclic, substituted or unsubstituted aliphatic moiety; a cyclic or acyclic, substituted or unsubstituted aliphatic heteroaliphatic moiety; a substituted or unsubstituted aryl moiety; or a substituted or unsubstituted heteroaryl moiety; and P is selected from the group consisting of hydrogren, lower ($C_1$-$C_6$) alkyl group, an acyl group, and a protecting group; is deprotonated under basic conditions (e.g., LDA, HMDS), and the resulting anion is reacted with an enone of formula:

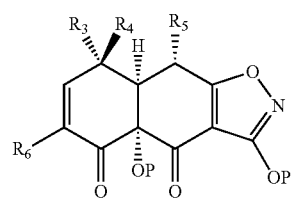

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O; —C(=O)$R_C$; —$CO_2R_C$; —CN; —SCN; —$SR_C$; —$SOR_C$; —$SO_2R_C$; —$NO_2$; —$N(R_C)_2$; —NHC(O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —$OR_F$, —CN, —SCN, —$SR_F$, alkylthio, arylthio, —$NO_2$, amino, —$N(R_F)_2$, and —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P is independently selected from the group consisting of hydrogen or a protecting group; to form the product:

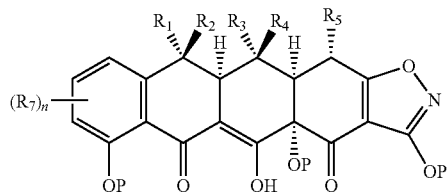

wherein
$R_1$, $R_3$, $R_4$, $R_5$, $R_7$, P, and n are as defined above;
$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; =O (taken with $R_1$); —C(=O)$R_B$; —$CO_2R_B$; —CN; —SCN; —$SR_B$; —$SOR_B$; —$SO_2R_B$; —$NO_2$; —$N(R_B)_2$; —NHC(O)$R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciated by one of skill in this art, the toluate may be further substituted in certain embodiments. In addition, the phenyl ring of the toluate may be substituted for an aromatic heterocyclic ring such as a pyridine ring. Other examples of carbocyclic and heterocyclic analogs of toluate (6) include:

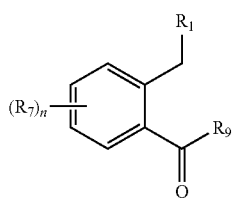 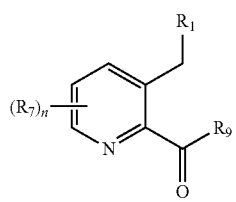

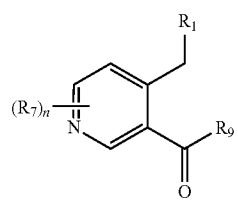 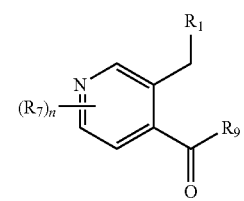

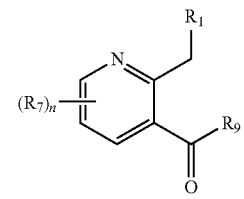 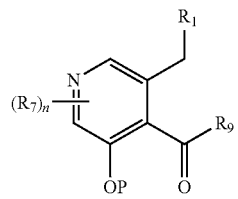

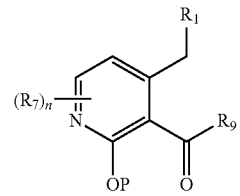 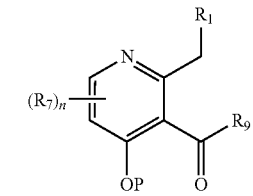

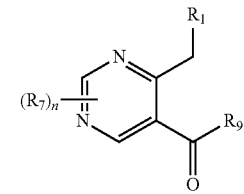 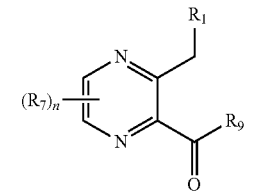

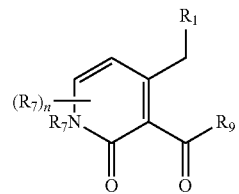 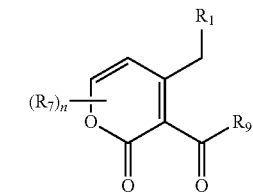

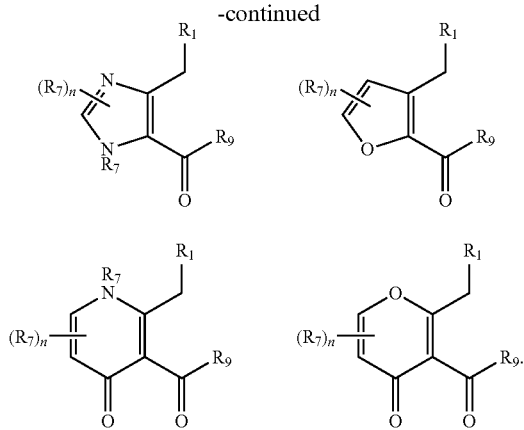

In certain embodiments, polycyclic toluates are used in the Michael-Dieckmann reaction sequence to form pentacyclines, hexacyclines, or higher cyclines. Toluates useful in preparing pentacyclines are exemplified by the formula:

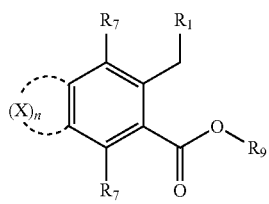

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each $R_7$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —N($R_G$)$_2$; —NHC(O)$R_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

represents a substituted or unsubstituted aryl, heteroaryl, carbocyclic, or heterocyclic moiety, in which each occurrence of X is selected from the group consisting of —O—, —S—, —$NR_8$—, —C($R_8$)$_2$—;

$R_8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_H$; =O; —C(=O)$R_H$; —$CO_2R_H$; —CN; —SCN; —$SR_H$; —$SOR_H$; —$SO_2R_H$; —$NO_2$; —N($R_H$)$_2$; —NHC(O)$R_H$; or —C($R_H$)$_3$; wherein each occurrence of $R_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 1 to 5, inclusive; and the bonds between adjacent X moieties are either single or double bonds; and $R_9$ is selected from the group consisting of substituted or unsubstituted aryl or heteroaryl groups.

In another embodiment, enone (18) is reacted with an anion, which is generated through metalation (e.g., metal-halogen exchange, metal-metalloid exchange, lithium-halogen exchange, lithium-tin exchange, etc. by reacting the toluate with the appropriate metal reagent) of a toluate of the following formula:

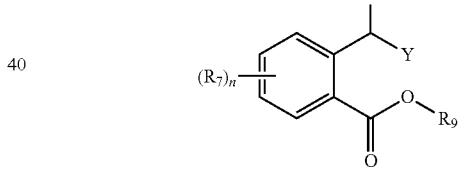

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; =O; —C(=O)$R_G$;

—CO$_2$R$_G$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 0 to 3, inclusive;

R$_9$ is selected from the group consisting of substituted or unsubstituted aryl or heteroaryl groups; and Y is a halogen or Sn(R$_Y$)$_3$, wherein R$_Y$ is alkyl. The anion generated is reacted with the enone (18) to generate a product of formula:

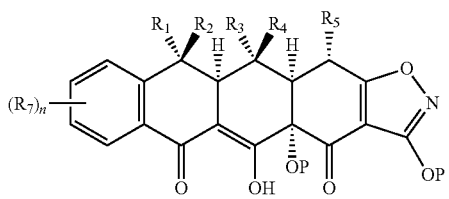

wherein

R$_1$, R$_3$, R$_4$, R$_5$, R$_7$, P, and n are as defined above; and

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

Any metal may be used in the metalation reaction to generate the metal anionic reagent to be reacted with the enone. In certain embodiments, the metal is a Group I element on the periodic chart. In other embodiments, the metal is a Group II element on the periodic chart. In other embodiments, the metal is a transition metal. Exemplary metals useful in the metalation reaction include sodium, lithium, calcium, aluminium, cadmium, copper, beryllium, arsenic, antimony, tin, magnesium, titanium, zinc, manganese, iron, cobalt, nickel, zinc, platinum, palladium, mercury, and ruthenium. In certain preferred embodiments, the metal is chosen from lithium, magnesium, titanium, zinc, and copper. In yet other embodiments, the metal is magnesium, lithium, sodium, beryllium, zinc, mercury, arsenic, antimony, or tin. In certain particular embodiments, a lithium-halogen exchange is used. The lithium-halogen exchange may be performed in situ in the presence of the enone. The lithium-halogen exchange may be preformed using any lithium reagent including, for example, alkyllithium reagents, n-butyllithium, t-butyllithium, phenyl lithium, mesityl lithium, and methyllithium. In certain embodiments, other organometallics reagents are generated and reacted with the enone. Examples include Grignard reagents, zero-valent metal complexes, ate complexes, etc. In certain embodiments, the metal reagent is a magnesium reagent including, but not limited to, magnesium metal, magnesium anthracene, activated magnesium turnings, etc. In certain embodiments, the reagent is zinc-based. The reagent may be generated in situ in the presence of the enone, or the reagent may be generated separately and later contacted with the enone. In certain embodiments, milder conditions for the cyclization are used (e.g., a zinc reagent).

As will be appreciated by one of skill in this art, the toluate may be further substituted in certain embodiments. In addition, the phenyl ring of the toluate may be substituted for an aromatic heterocyclic ring or ring system such as a pyridine ring. Examples of carbocyclic and heterocyclic analogs of toluate include:

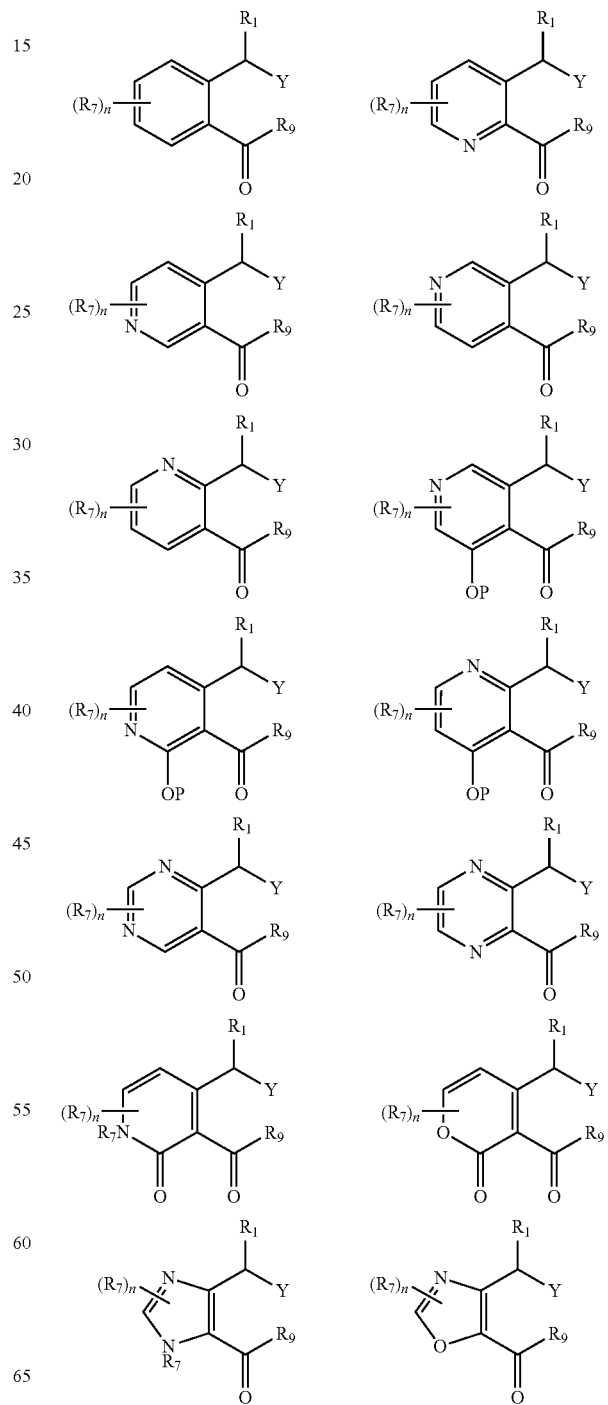

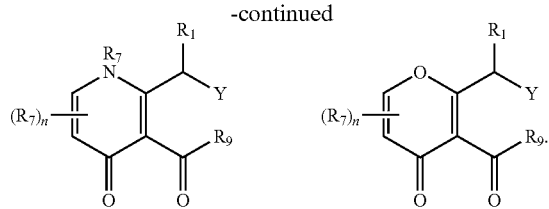

In certain embodiments, the halogen Y is bromine. In other embodiments, Y is iodine. In yet other embodiments, Y is chloride. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metalation reaction, Y is a metal such as lithium, magnesium, zinc, copper, antimony, sodium, etc. In certain embodiments, R$_1$ is hydrogen or lower alkyl (C$_1$-C$_6$). In certain particular embodiments, R$_1$ is hydrogen.

In other embodiments, polycyclic toluates may be used to prepare pentacyclines, hexacyclines, or higher cyclines. Toluates useful in the preparation of such cyclines are of the formula:

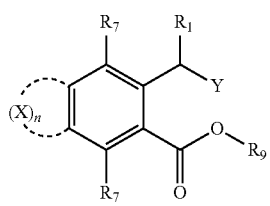

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each R$_7$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; =O; —C(=O)R$_G$; —CO$_2$R$_G$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

represents a substituted or unsubstituted aryl, heteroaryl, carbocyclic, or heterocyclic moiety, in which each occurrence of X is selected from the group consisting of —O—, —S—, —NR$_8$—, —C(R$_8$)$_2$—;

R$_8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_H$; =O; —C(=O)R$_H$; —CO$_2$R$_H$; —CN; —SCN; —SR$_H$; —SOR$_H$; —SO$_2$R$_H$; —NO$_2$; —N(R$_H$)$_2$; —NHC(O)R$_H$; or —C(R$_H$)$_3$; wherein each occurrence of R$_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 1 to 5, inclusive; and the bonds between adjacent X moieties are either single or double bonds;

R$_9$ is selected from the group consisting of substituted or unsubstituted aryl or heteroaryl groups; and Y is a halogen or Sn(R$_Y$)$_3$, wherein R$_Y$ is alkyl. In certain embodiments, the halogen Y is bromine. In certain embodiments, the halogen Y is bromine. In other embodiments, Y is iodine. In yet other embodiments, Y is chloride. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metalation reaction, Y is a metal such as lithium, magnesium, zinc, copper, sodium, mercury, antimony, etc. In certain embodiments, R$_1$ is hydrogen or lower alkyl(C$_1$-C$_6$). In certain particular embodiments, R$_1$ is hydrogen. In certain embodiments, R$_9$ is phenyl or substituted phenyl. In certain embodiments, ortho-R$_7$ is alkoxy such as methoxy. In other embodiments, R$_7$ is hydrogen. Exemplary polycyclic toluates include:

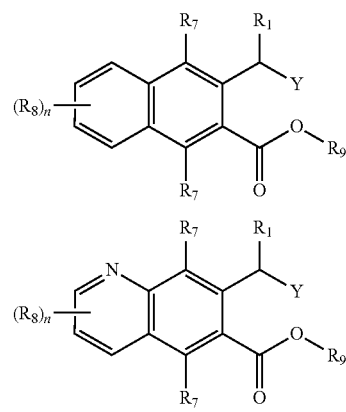

-continued

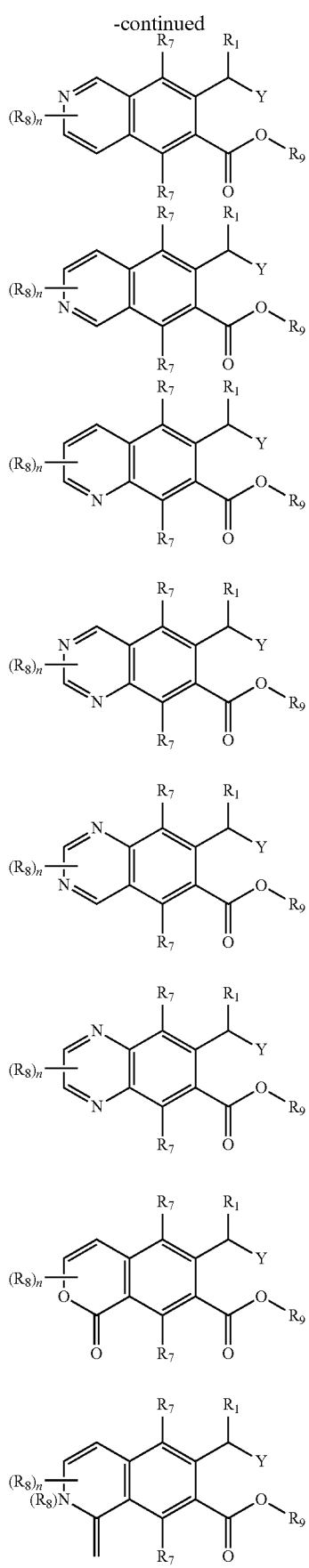

-continued

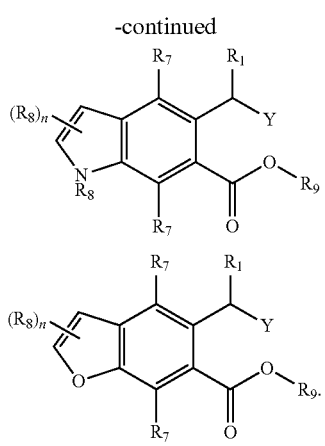

Compounds of the formula below with a heterocyclic C-ring:

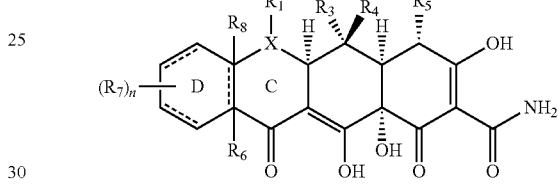

may be prepared by Michael-Dieckmann closure of a D-ring precursor derived from the corresponding anilide, phenol, or thiophenol. A representative example using anthranilic acid (i.e., anilide as the nucleophile in the Michael addition reaction) is shown below:

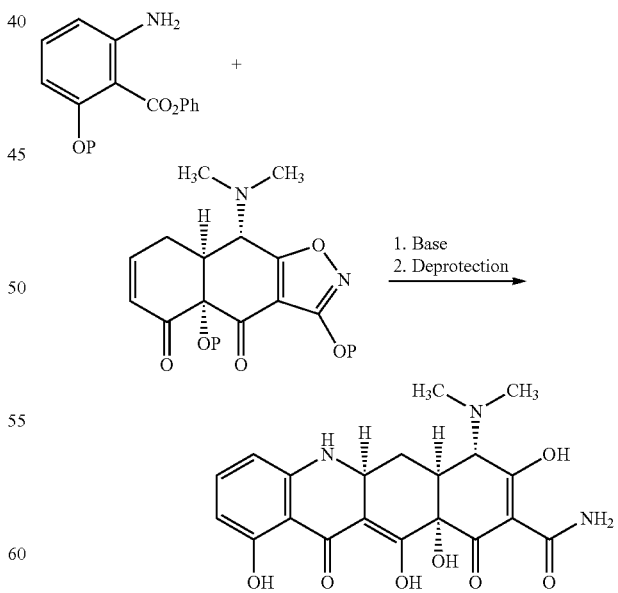

In another embodiment, the enone (18) is reacted with a benzocyclobutenol in an o-quinone dimethide Diels-Alder reaction. The enone (18) is reacted under suitable conditions (e.g., heat) with a benzocyclobutenol of formula:

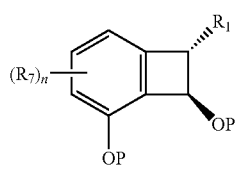

wherein

R₁ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; =O; —C(=O)R$_G$; —CO$_2$R$_G$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P are each selected independently from the group consisting of hydrogen or a protecting group; and n is an integer in the range of 0 to 3, inclusive;
to form the product of formula:

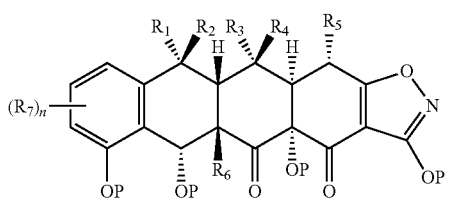

wherein R$_1$, R$_3$, R$_4$, R$_5$, R$_6$, R$_7$, and P are defined as above; and R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciate by one of skill in this art, the reactants may be substituted further and still fall within the claimed invention. For example, the phenyl ring of the benzocyclobutenol ring may be further substituted.

In another embodiment, the enone is reacted with a diene in a Diels-Alder reaction to yield a tricycline. The enone (18) is reacted under suitable conditions (e.g., heat) with a diene of formula:

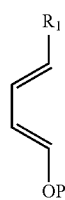

wherein

R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P are each selected independently from the group consisting of hydrogen and protecting groups;
to yield a protected tricycline of formula:

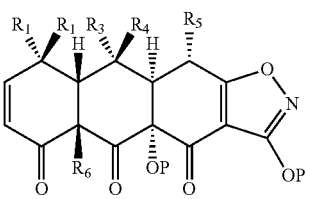

wherein

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciated by one of skill in this art, the enone and diene may be further substituted and still be encompassed within the present invention.

In yet another embodiment, the enone is reacted with an anion of a phthalide or cyano-phthalide. The enone (18) is reacted under basic conditions (e.g., LDA, Ph₃CLi) with the anion of the phthalide of formula:

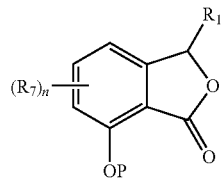

wherein

R₁ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; =O; —C(=O)R$_A$; —CO₂R$_A$; —CN; —SCN; —SR$_A$; —SOR$_A$; —SO₂R$_A$; —NO₂; —N(R$_A$)₂; —NHC(O)R$_A$; or —C(R$_A$)₃; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R₇ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; =O; —C(=O)R$_G$; —CO₂R$_G$; —CN; —SCN; —SR$_G$; —SOR$_G$; —SO₂R$_G$; —NO₂; —N(R$_G$)₂; —NHC(O)R$_G$; or —C(R$_G$)₃; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is hydrogen, C₁-C₆ alkyl group, acyl group, or an oxygen-protecting group; and n is an integer in the range of 0 to 3, inclusive;

to yield a product of formula:

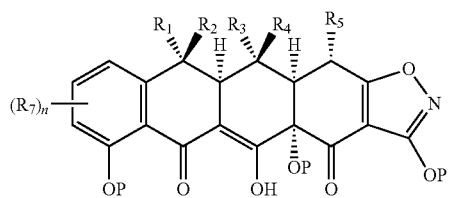

wherein R₂ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; =O; —C(=O)R$_B$; —CO₂R$_B$; —CN; —SCN; —SR$_B$; —SOR$_B$; —SO₂R$_B$; —NO₂; —N(R$_B$)₂; —NHC(O)R$_B$; or —C(R$_B$)₃; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

The products of the above reactions are optionally further functionalized, reduced, oxidized, rearranged, protected, and deprotected to yield the final desired product. Each of the above steps may be followed with an appropriate work-up and purification of the desired product. As will be appreciated by one of skill in the art, various isolation and purification techniques including flash chromatography, crystallization, distillation, HPLC, thin layer chromatography, extraction, filtration, etc. may be used in the course of synthesizing compounds of the invention. These techniques may be used in the preparation or purification of intermediates, reagents, products, starting materials, or solvents.

Intermediates

Along with synthetic methodology, the invention also provides useful intermediates useful in the preparation of the enone (9) and tetracycline analogs.

In certain embodiments, the invention provides a compound of formula (VIII):

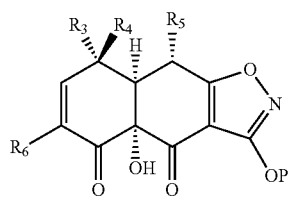

(VIII)

wherein

R₃ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; =O (taken with R₄); —C(=O)R$_C$; —CO₂R$_C$; —CN; —SCN; —SR$_C$; —SOR$_C$; —SO₂R$_C$; —NO₂; —N(R$_C$)₂; —NHC(O)R$_C$; or —C(R$_C$)₃; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R₄ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; =O (taken with R₃); —C(=O)R$_D$; —CO₂R$_D$; —CN; —SCN; —SR$_D$; —SOR$_D$; —SO₂R$_D$; —NO₂; —N(R$_D$)₂; —NHC(O)R$_D$; or —C(R$_D$)₃; wherein each occurrence of R$_D$ is independently a hydrogen, a protecting group, an aliphatic moiety, a heteroaliphatic moiety, an acyl moiety; an aryl moiety; a heteroaryl moiety;

alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —$OR_F$, —CN, —SCN, —$SR_F$, alkylthio, arylthio, —$NO_2$, amino, —$N(R_F)_2$, and —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of P is independently selected from the group consisting of hydrogen and an oxygen-protecting group; and salts, tautomers, stereoisomers, enantiomers, diastereomers, and derivates thereof. In certain embodiments, $R_3$ is hydrogen. In certain embodiments, $R_3$ is fluorine. In other embodiments, $R_3$ is substituted or unsubstituted aliphatic. In yet other embodiments, $R_3$ is substituted or unsubstituted heteroaliphatic. In certain particular embodiments, $R_3$ is $C_1$-$C_6$alkyl. In certain embodiments, $R_3$ is hydroxyl or protected hydroxyl. In certain embodiments, $R_3$ is thiol or protected thiol. In certain embodiments, $R_4$ is hydrogen. In certain embodiments, $R_4$ is fluorine. In other embodiments, $R_4$ is substituted or unsubstituted aliphatic. In yet other embodiments, $R_4$ is substituted or unsubstituted heteroaliphatic. In certain particular embodiments, $R_4$ is $C_1$-$C_6$alkyl. In certain embodiments, $R_4$ is hydroxyl or protected hydroxyl. In certain embodiments, $R_4$ is thiol or protected thiol. In certain embodiments, both $R_3$ and $R_4$ are hydrogen. In certain embodiments, $R_5$ is —$N(R_E)_2$. In certain embodiments, $R_5$ is —$N(R_E)_2$, wherein $R_E$ is hydrogen or $C_1$-$C_6$ alkyl. In certain embodiments, $R_5$ is —$N(R_E)_2$, wherein $R_E$ is methyl. In certain embodiments, $R_5$ is —$OR_E$ or —$SR_E$. In certain embodiments, $R_5$ is substituted or unsubstituted aliphatic. In other embodiments, $R_5$ is substituted or unsubstituted heteroaliphatic. In certain embodiments, $R_5$ is $C_1$-$C_6$alkyl. In certain particular embodiments, $R_5$ is hydrogen. In certain embodiments, the chiral center to which $R_5$ is attached is inverted from that shown in formula (VIII). In certain embodiments, $R_6$ is hydrogen. In other embodiments, $R_6$ is substituted or unsubstituted aliphatic. In yet other embodiments, $R_6$ is substituted or unsubstituted heteroaliphatic. In certain particular embodiments, $R_6$ is $C_1$-$C_6$alkyl. In certain embodiments, $R_3$, $R_4$, and $R_6$ are all hydrogen. In certain embodiments, P is benzyl. In other embodiments, P is hydrogen. In yet other embodiments, P is acyl. In yet other embodiments, P is a silicon-containing protecting group. An exemplary compound of the formula VIII includes:

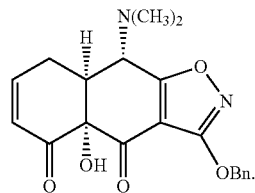

In other embodiments, the invention provides a compound of formula (VII):

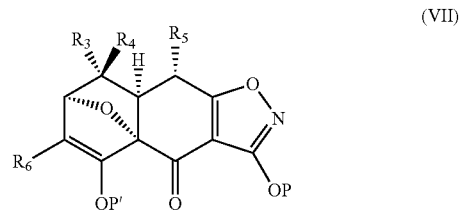

(VII)

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O (taken with $R_4$); —C(=O)$R_C$; —$CO_2R_C$; —CN; —SCN; —$SR_C$; —$SOR_C$; —$SO_2R_C$; —$NO_2$; —$N(R_C)_2$; —NHC(O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —$OR_F$, —CN, —SCN, —$SR_F$, alkylthio, arylthio, —$NO_2$, amino, —$N(R_F)_2$, and —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is hydrogen or an oxygen-protecting group; and

P' is hydrogen, $C_1$-$C_6$ alkyl group, acyl group, or an oxygen-protecting group; and salts, tautomers, stereoisomers, enantiomers, diastereomers, and derivates thereof. $R_3$, $R_4$, $R_5$, $R_6$, and P are as defined in any of the genera, classes, subclasses, or species described herein. In certain embodiments, P' is $C_1$-$C_6$alkyl. In certain embodiments, P' is methyl. In certain embodiments, P' is a silicon-containing protecting group. In other embodiments, P' is acyl. In yet other embodiments, P' is acetyl. In certain embodiments, P' is hydrogen. An examplary compound of the formula VII includes:

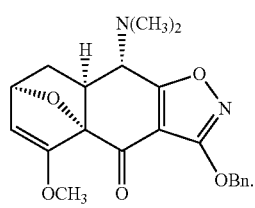

In certain embodiments, the compound is of formula (VI):

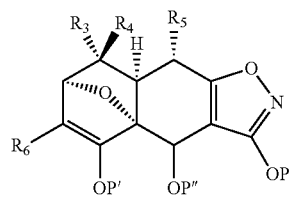

(VI)

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O (taken with $R_4$); —C(=O)$R_C$; —$CO_2R_C$; —CN; —SCN; —$SR_C$; —$SOR_C$; —$SO_2R_C$; —$NO_2$; —$N(R_C)_2$; —NHC(O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —OH, —CN, —SCN, —SH, alkylthio, arylthio, —$NO_2$, amino, alkyl amino, and dialkyl amino groups;

P is hydrogen or an oxygen-protecting group;

P' is hydrogen, $C_1$-$C_6$ alkyl group, acyl group, or an oxygen-protecting group;

P''' is hydrogen or an oxygen-protecting group; and salts, tautomers, stereoisomers, enantiomers, diastereomers, and derivates thereof. $R_3$, $R_4$, $R_5$, $R_6$, P, and P' are as defined in any of the genera, classes, subclasses, or species described herein. In certain embodiments, P' is $C_1$-$C_6$alkyl. In certain embodiments, P' is methyl. In certain embodiments, P' is a silicon-containing protecting group. In other embodiments, P' is acyl. In yet other embodiments, P' is acetyl. In certain embodiments, P' is hydrogen. In certain embodiments, P''' is hydrogen. In other embodiments, P''' is a silicon-containing protecting group. In other embodiments, P''' is $C_1$-$C_6$ alkyl. In yet other embodiments, P''' is acyl. In still other particular embodiments, P''' is acetyl. An exemplary compound of the formula VI includes:

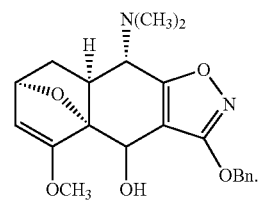

In certain embodiments, the invention provides a compound of formula (V):

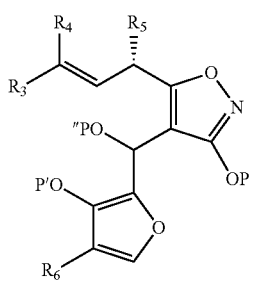

(V)

wherein
R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; =O (taken with R$_4$); —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; =O (taken with R$_3$); —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_E$; —CN; —SCN; —SR$_E$; or —N(R$_E$)$_2$; wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is selected from the group consisting of hydrogen, halogen, substituted or unsubstituted aliphatic, substituted or unsubstituted heteroaliphatic, substituted or unsubstituted alkoxy, —OR$_F$, —CN, —SCN, —SR$_F$, alkylthio, arylthio, —NO$_2$, amino, —N(R$_F$)$_2$, and —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is hydrogen or an oxygen-protecting group; and

P' is hydrogen, C$_1$-C$_6$ alkyl group, acyl group, or an oxygen-protecting group; and salts, tautomers, stereoisomers, enantiomers, diastereomers, and derivates thereof. R$_3$, R$_4$, R$_5$, R$_6$, P, P', and P'' are as defined in any of the genera, classes, subclasses, or species described herein. An exemplary compounds of formula IV includes:

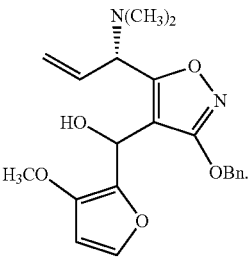

In other embodiments, the invention provides a compound of formula (IIIa):

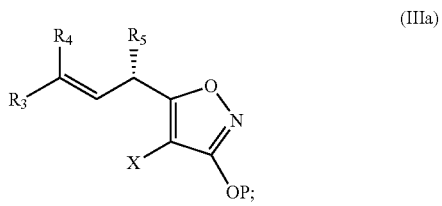

(IIIa)

wherein
X is hydrogen or a halogen;
R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; =O (taken with R$_4$); —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; =O (taken with R$_3$); —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P is hydrogen or an oxygen-protecting group; and salts, tautomers, stereoisomers, enantiomers, diastereomers, and derivates thereof. $R_3$, $R_4$, $R_5$, and P are as defined in any of the genera, classes, subclasses, or species described herein. In certain embodiments, X is hydrogen. In certain other embodiments, X is iodine. In yet other embodiments, X is bromine. Exemplary compound of formula IIIa include:

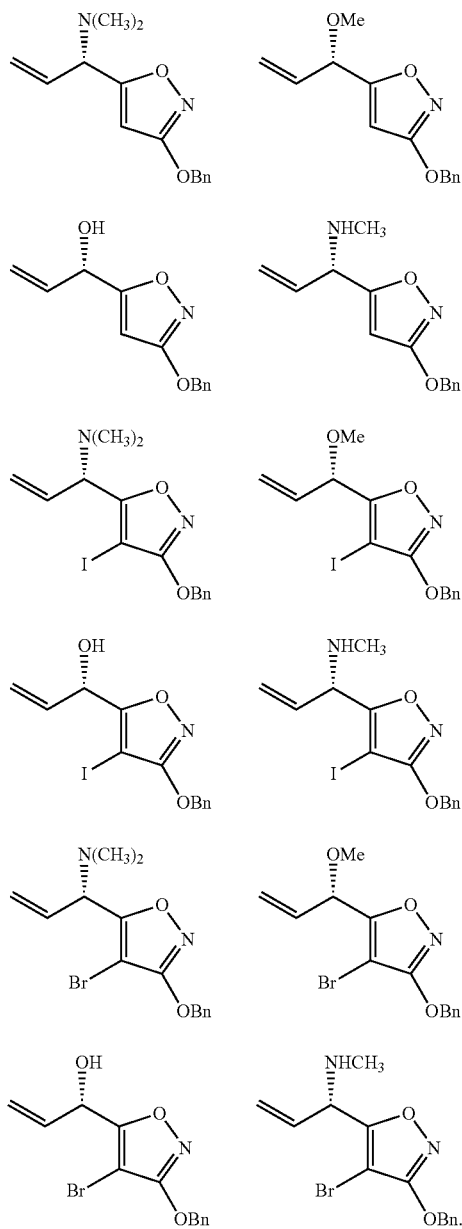

In other embodiments, the invention provides a compound of formula (IIIb):

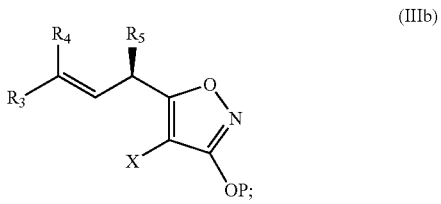

wherein

X is hydrogen or a halogen;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O (taken with $R_4$); —C(=O)$R_C$; —$CO_2R_C$; —CN; —SCN; —$SR_C$; —$SOR_C$; —$SO_2R_C$; —$NO_2$; —$N(R_C)_2$; —NHC(O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P is hydrogen or an oxygen-protecting group; and salts, tautomers, stereoisomers, enantiomers, diastereomers, and derivates thereof. $R_3$, $R_4$, $R_5$, and P are as defined in any of the genera, classes, subclasses, or species described herein. In certain embodiments, X is hydrogen. In certain other embodiments, X is iodine. In yet other embodiments, X is bromine. Exemplary compound of formula IIIb include:

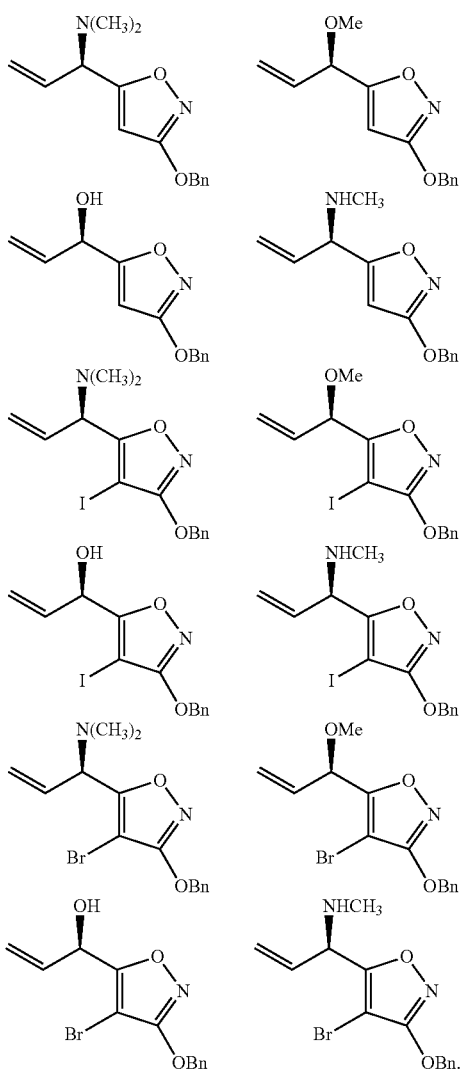

In still other embodiments, the compound is of formula (II):

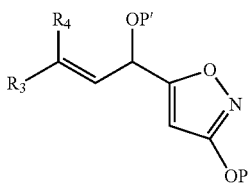

(II)

wherein

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; =O (taken with R$_4$); —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; =O (taken with R$_3$); —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P is hydrogen or an oxygen-protecting group;

P' is hydrogen or an oxygen-protecting group; and salts, tautomers, stereoisomers, enantiomers, diastereomers, and derivates thereof. R$_3$, R$_4$, R$_5$, and P are as defined in any of the genera, classes, subclasses, or species described herein. In certain embodiments, P' is acyl. In certain particular embodiments, P' is acetyl. In other embodiments, P' is a fatty acid. In other embodiments, P' is C$_1$-C$_6$ alkyl. In certain embodiments, P' is a silicon-containing protecting group. In certain particular embodiments, P' is hydrogen. In certain embodiments, the compound is of formula (IIb):

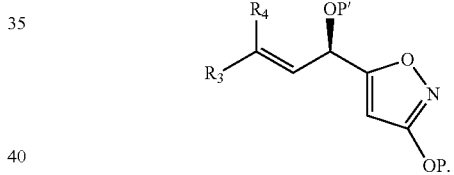

In other embodiments, the compound is of formula (IIa):

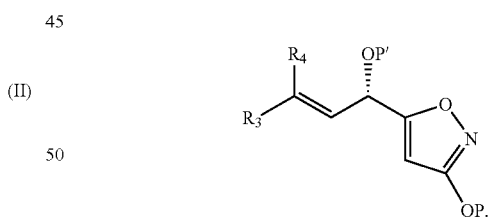

Exemplary compounds of formula II include:

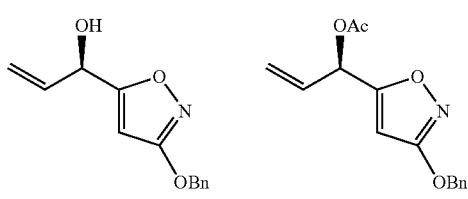

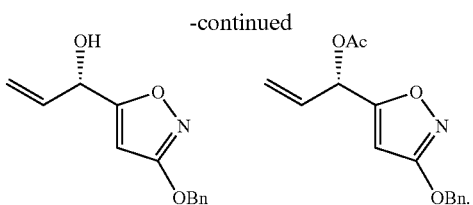

Tetracycline Analogs

Compounds that can be prepared using the intermediates, reagents, and synthetic methodologies described herein include any tetracycline analogs, including, but not limited to, tetracyclines, heterocyclic tetracycline analogs, dicyclines, tricyclines, pentacyclines, heterocylic pentacyclines, bridged pentacyclines, heterocyclic polycyclines, bridged polycyclines, and other polycyclines, as described in U.S. patent application US 2005/0282787, published on Dec. 22, 2005; PCT application WO 05/112945, published Dec. 1, 2005; and U.S. provisional patent application, U.S. Ser. No. 60/790,413, filed Apr. 7, 2006; each of which is incorporated herein by reference. Any of the genera, classes, subclasses, or species described in these application may be prepared using the inventive system. Particularly useful compounds of the present invention include those with biological activity. In certain embodiments, the compounds of the invention exhibit antimicrobial activity. For example, the compound may have a mean inhibitory concentration, with respect to a particular bacteria, of less than 100 μg/mL, of less than 50 μg/mL, preferably less than 25 μg/mL, more preferably less than 5 μg/mL, and most preferably less than 1 μg/mL or less than 0.1 μg/mL. For example, infection caused by the following organisms may be treated with antimicrobial compounds of the invention: Gram-positivives—*Staphylococcus aureus, Staphylococcus epidermidis, Streptococcus* Group A, *Streptococcus viridans, Streptococcus pneumoniae, Enterococcus faecalis*; Gram-negatives—*Neisseria meningitidis, Neisseria gonorrhoeae, Haemophilus influenzae, Escherichia coli, Klebsiella pneumoniae, Pseudomonas aeruginosa, Acinetobacter baumannii, Bacteroides fragilis*, other *Bacteroides*; and others—*Mycoplasma pneumoniae, Treponema pallidum, Rickettsia*, and *Chlamydia*. In certain embodiments, the compounds exhibit anti-fungal activity. In other embodiments, the compounds of the invention exhibit antiproliferative activity.

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis of Chiral Enone

General Procedures. All reactions were performed in flame-dried round bottomed or modified Schlenk (Kjeldahl shape) flasks fitted with rubber septa under a positive pressure of argon, unless otherwise noted. Air- and moisture-sensitive liquids and solutions were transferred via syringe or stainless steel cannula. Where necessary (so noted), solutions were deoxygenated by alternative freeze (liquid nitrogen)/evacuation/thaw cycles (≧three iterations). Organic solutions were concentrated by rotary evaporation at ~25 Torr (house vacuum). Flash column chromatography was performed on silica gel (60 Å, standard grade) as described by Still et al. (Still, W. C.; Kahn, M.; Mitra, A. *J. Org. Chem.* 1978, 43, 2923-2925; incorporated herein by reference). Analytical thin-layer chromatography was performed using glass plates pre-coated with 0.25 mm 230-400 mesh silica gel impregnated with a fluorescent indicator (254 nm). Thin layer chromatography plates were visualized by exposure to ultraviolet light and/or exposure to ceric ammonium molybdate or an acidic solution of p-anisaldehyde followed by heating on a hot plate.

Materials. Commercial reagents and solvents were used as received with the following exceptions. Chlorotrimethylsilane, triethylamine, diisopropylamine, 2,2,6,6-tetramethylpiperidine, N,N,N',N'-tetramethylethylenediamine, DMPU, HMPA, and N,N-diisopropylethylamine were distilled from calcium hydride under dinitrogen atmosphere. Benzene, dichloromethane, ethyl ether, methanol, pyridine, tetrahydrofuran, hexane, acetonitrile, N,N-dimethylformamide, and toluene were purified by the method of Pangborn et al. (Pangborn, A. B.; Giardello, M. A.; Grubbs, R. H.; Rosen, R. K.; Timmers, F. J. *Organometallics* 1996, 15, 1518-1520; incorporated herein by reference). The molarity of n-butyllithium, s-butyllithium, and t-butyllithium were determined by titration with a tetrahydrofuran solution of 2-butanol using triphenylmethane as an indicator (Duhamel, L.; Palquevent, J.-C. *J. Org. Chem.* 1979, 44, 3404-3405; incorporated herein by reference).

Instrumentation. Proton nuclear magnetic resonance ($^1$H NMR) spectra and carbon nuclear magnetic resonance ($^{13}$C NMR) were recorded with Varian Unity/Inova 600 (600 MHz), Varian Unity/Inova 500 (500 MHz/125 MHz), or Varian Mercury 400 (400 MHz/100 MHz) NMR spectrometers. Chemical shifts for protons are reported in parts per million scale (δ scale) downfield from tetramethylsilane and are referenced to residual protium in the NMR solvents (CHCl$_3$: δ 7.26, C$_6$D$_5$H: δ 7.15, D$_2$HCOD: δ 3.31, CDHCl$_2$: δ 5.32, (CD$_2$H)CD$_3$SO: δ 2.49). Chemical shifts for carbon are reported in parts per million (δ scale) downfield from tetramethylsilane and are referenced to the carbon resonances of the solvent (CDCl$_3$: δ 77.0, C$_6$D$_6$: δ 128.0, D$_3$COD: δ 44.9, CD$_2$Cl$_2$: δ 53.8, (CD$_3$)$_2$SO: δ 39.5). Data are represented as follows: chemical shift, multiplicity (s=singlet, d=doublet, t=triplet, q=quartet, m=multiplet, br=broad), integration, coupling constant in Hz, and assignment. Infrared (IR) spectra were obtained using a Perkin-Elmer 1600 FT-IR spectrophotometer referenced to a polystyrene standard. Data are represented as follows: frequency of the absorption (cm$^{-1}$), intensity of absorption (s=strong, sb=strong broad, m=medium, w=weak, br=broad), and assignment (where appropriate). Optical rotations were determined on a JASCO DIP-370 digital polarimeter equipped with a sodium lamp source using a 200-μL or 2-mL solution cell. High resolution mass spectra were obtained at the Harvard University Mass Spectrometry Facilities.

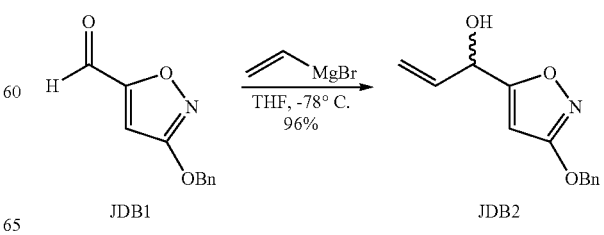

Allylic Alcohol JDB2:

A solution of vinylmagnesium bromide in tetrahydrofuran (1.0 M, 36.5 mL, 36.4 mmol, 2.0 equiv) was added via syringe to a solution of aldehyde JDB1 (3.70 g, 18.2 mmol, 1 equiv) in tetrahydrofuran (36 mL) at −78° C. (Riess, R.; Schon, M.; Laschat, S.; Jager, V. *Eur. J. Org. Chem.* 1998, 473-479; incorporated herein by reference). The reaction solution was stirred at −78° C. for 40 min and the cooling bath was removed. Saturated aqueous ammonium chloride (50 mL) was added and the product solution was extracted with ethyl acetate (50 mL). The organic layer was washed with saturated aqueous sodium chloride (40 mL) and the washed solution was dried over sodium sulfate. The dried solution was filtered and the filtrate was concentrated. The residue obtained was purified by flash-column chromatography on silica gel (30% ethyl acetate-hexanes) to furnish the allylic alcohol JDB2 (4.04 g, 96%) as a clear, colorless oil.

| TLC (30% ethyl acetate-hexanes) | $R_f$ = 0.25 (UV, CAM). |
|---|---|
| ¹HNMR (500 MHz, CDCl₃), δ: | 7.43-7.34 (m, 5H, ArH), 6.04 (ddd, 1H, J = 17.1, 10.3, 5.9 Hz, CH₂=CH), 5.87 (s, 1H, IsoxH), 5.46 (d, 1H, J = 17.1, trans-CHH=CH), 5.34 (d, 1H, J = 10.3 Hz, cis-CHH=CH), 5.24 (s, 2H, OCH₂Ar), 5.22 (t, 1H, J = 5.34 Hz, CHOH), 2.25 (br s, 1H, OH). |
| ¹³CNMR (100 MHz, CDCl₃), δ: | 173.3, 171.6, 135.7, 135.3, 128.6, 128.5, 128.2, 118.0, 92.9, 71.6, 68.3. |
| IR (neat), cm⁻¹: | 3361 (bs), 1615 (s), 1503 (s), 1451 (s), 1364 (s) 1216 (w), 1119 (w), 1036 (s), 986 (s), 932 (s). |
| HRMS (ESI): | Calcd for (C₁₃H₁₃NO₃ + H)⁺: 232.0973 Found: 232.0973. |

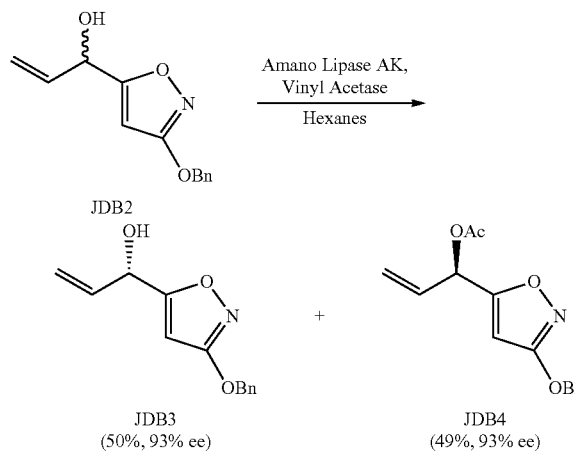

Kinetic Resolution of Allylic Alcohol JDB2:

Amano Lipase AK (125 mg) was added to a mixture of allylic alcohol 2 (1.00 g, 4.30 mmol, 1 equiv), 4 Å molecular sieves (65 mg), and vinyl acetate (3.40 mL, 36.9 mmol, 8.57 equiv) in hexanes (17 mL) at 23° C. After stiffing for 52.5 h, the reaction mixture was filtered and the filtrate was concentrated. The residue was purified by flash-column chromatography on silica gel (20% ethyl acetate-hexanes, grading to 35% ethyl acetate-hexanes) to furnish separately the R-allylic acetate JDB3 (583 mg, 49%, 93% ee by the Mosher method) as a clear, colorless oil and the S-allylic alcohol JDB4 (500 mg, 50%, 93% ee by the Mosher method on the corresponding alcohol) as a clear, colorless oil (Dale, J. A.; Mosher, H. S. *J. Am. Chem. Soc.* 1973, 95, 512-519; incorporated herein by reference).

Allylic Alcohol JDB3—See above for characterization.
Allylic Acetate JDB4—

| TLC (40% ethyl acetate-hexanes) | $R_f$ = 0.50 (UV, CAM). |
|---|---|
| ¹HNMR (500 MHz, CDCl₃), δ: | 7.45-7.35 (m, 5H, ArH), 6.28 (d, 1H, J = 6.8 Hz, CHOAc), 6.01 (ddd, 1H, J = 17.1, 10.3, 6.8 Hz, CH₂=CH), 5.91 (s, 1H, IsoxH), 5.46 (d, 1H, J = 17.1, trans-CHH=CH), 5.40 (d, 1H, J = 10.3 Hz, cis-CHH=CH), 5.26 (s, 2H, OCH₂Ar), 2.13 (s, 3H, C(O)CH₃). |
| ¹³CNMR (100 MHz, CDCl₃), δ: | 171.4, 169.6, 169.3, 135.6, 131.4, 128.6, 128.5, 128.2, 120.0, 94.5, 71.6, 68.2, 20.8. |
| IR (neat), cm⁻¹: | 1746 (s), 1619 (m), 1507 (s), 1451 (m), 1368 (s), 1027 (m), 980 (m), 904 (s). |
| HRMS (ESI): | Calcd for (C₁₅H₁₅NO₄ + H)⁺: 274.1079 Found: 274.1091. |

R-Allylic Alcohol JDB5:

Solid potassium carbonate (445 mg, 3.20 mmol, 1.50 equiv) was added in one portion to a solution of allylic acetate JDB4 (583 mg, 2.14 mmol, 1 equiv) in methanol (7.1 mL) at 23° C. After stirring for 17 min, the reaction mixture was partitioned between water (100 mL) and diethyl ether (100 mL). The layers were separated and the organic layer was washed with saturated aqueous sodium chloride (50 mL). The washed layer was dried over sodium sulfate and the solids were filtered. The filtrate was concentrated to furnish allylic alcohol JDB5 (490 mg, 99%) as a clear, colorless oil.

See above for characterization.

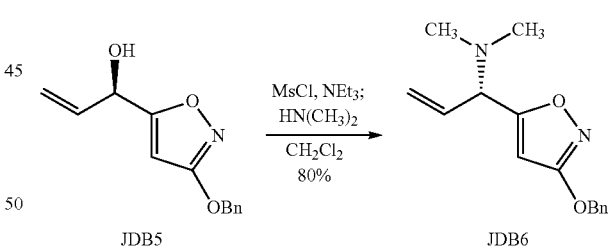

Amine JDB6:

Methanesulfonyl chloride (589 μL, 7.46 mmol, 1.15 equiv) was added dropwise via syringe to a solution of alcohol JDB5 (1.50 g, 6.49 mmol, 1 equiv) and triethylamine (1.18 mL, 8.44 mmol, 1.30 equiv) in dichloromethane (65 mL) at −10° C. After stiffing at −10° C. for 40 min, the reaction mixture was cooled to −30° C. and a solution of dimethylamine in tetrahydrofuran (5.30 M, 7.40 mL, 38.9 mmol, 6.00 equiv) was added via syringe. The reaction mixture was allowed to warm slowly to 5° C. over 4.5 h, then was partitioned between aqueous potassium phosphate buffer (pH 7.0, 0.05 M, 50 mL) and dichloromethane (100 mL). The aqueous layer was further extracted with dichloromethane (50 mL). The organic layers were combined and the combined layers were washed with saturated aqueous sodium chloride solution (50 mL). The washed solution was dried over sodium sulfate and the solids were filtered. The filtered solution was concentrated and the residue obtained was purified by flash-column chromatography on silica gel (0.5% methanol-dichloromethane, grading to 3% methanol-dichloromethane) to furnish the allylic amine JDB6 (1.34 g, 80%) as a clear, colorless oil.

| | |
|---|---|
| TLC (40% acetone-hexanes) | $R_f$ = 0.42 (UV, CAM). |
| $^1$HNMR (500 MHz, CDCl$_3$), δ: | 7.46-7.36 (m, 5H, ArH), 5.94 (m, 1H, CH$_2$=CH), 5.81 (s, 1H, IsoxH), 5.32-5.29 (m, 2H, CHH=CH), 5.26 (s, 2H, OCH$_2$Ar), 2.27 (s, 6H, N(CH$_3$)$_2$). |
| $^{13}$CNMR (100 MHz, CDCl$_3$), δ: | 172.5, 171.6, 135.8, 134.1, 128.6, 128.5, 128.3, 119.5, 93.9, 71.5, 66.3, 42.3. |
| IR (neat), cm$^{-1}$: | 2946 (w), 2869 (w), 2827 (w), 2782 (w), 1607 (s), 1501 (s), 1449 (s), 1366 (s), 1138 (w), 1036 (s), 992 (s), 926 (s). |
| HRMS (ESI): | Calcd for (C$_{15}$H$_{18}$N$_2$O$_2$ + H)$^+$: 259.1446<br>Found: 259.1436. |

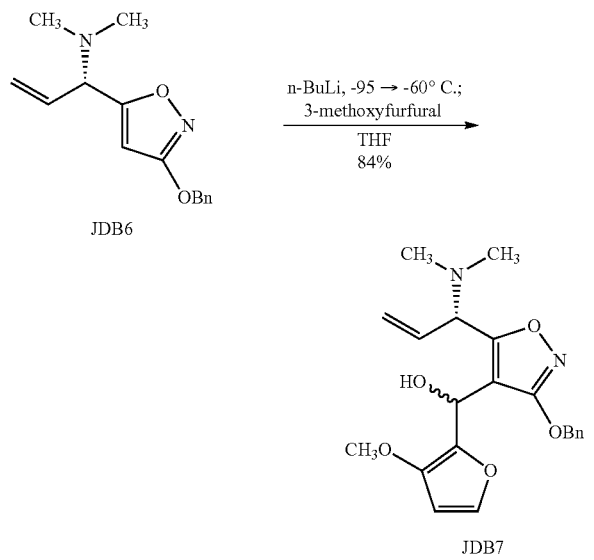

JDB6

JDB7

Furyl Alcohol JDB7:

A solution of n-butyllithium in hexanes (2.50 M, 815 µL, 2.13 mmol, 1.10 equiv) was added dropwise over 10 min to a solution of isoxazole JDB6 (500 mg, 1.94 mmol, 1 equiv) in tetrahydrofuran (19.4 mL) at −95° C. The resulting yellow solution was allowed to warm to −60° C. over 20 min, at which point the mixture had become reddish-brown. The mixture was stirred at −60° C. for 1 h and a solution of 3-methoxyfurfural (292 mg, 2.13 mmol, 1.2 equiv) in tetrahydrofuran (4.0 mL) was added dropwise via cannula. The reaction mixture was allowed to warm to −50° C. over 45 min. The product solution was partitioned between aqueous potassium phosphate buffer (pH 7.0, 0.05 M, 30 mL) and dichloromethane (75 mL). The aqueous layer was further extracted with dichloromethane (50 mL). The organic layers were combined and the combined solution was dried over sodium sulfate. The solids were filtered and the filtered solution was concentrated. The residue obtained was purified by flash-column chromatography on silica gel (50% diethyl ether-pentane, grading to 75% diethyl ether-pentane) to furnish the furyl alcohol JDB7 (626 mg, 84%) as a clear, colorless oil.

| | |
|---|---|
| TLC (60% diethyl ether-pentane) | $R_f$ = 0.16 (UV, CAM) |
| $^1$HNMR (500 MHz, CDCl$_3$, 1.4:1 mixture of epimers at the secondary carbinol, * denotes minor epimer), δ: | 7.33-7.25 (m, 5H, ArH), 7.33-7.25* (m, 5H, ArH), 7.14 (d, 1H, J = 1.95, FurH), 7.13* (d, 1H, J = 1.95, FurH), 6.25 (m, 1H, FurH), 6.25* (m, 1H, FurH), 6.23-6.10 (m, 1H, CH$_2$=CH), 6.23-6.10* (m, 1H, CHH=CH), 5.78 (s, 1H, CHOH), 5.72* (s, 1H, CHOH), 5.41-5.37 (m, 2H, CHH=CH), 5.41-5.37* (m, 2H, CHH=CH), 5.23-5.15 (m, 2H, OCH$_2$Ar), 5.23-5.15* (m, 2H, OCH$_2$Ar), 4.19* (d, 1H, J = 9.8 Hz, CHN(CH$_3$)$_2$), 4.01 (d, 1H, J = 9.3 Hz, CHN(CH$_3$)$_2$), 3.62* (s, 3H, OCH$_3$), 3.60 (s, 3H, OCH$_3$), 2.32 (s, 1H, CHN(CH$_3$)$_2$), 2.32* (s, 1H, CHN(CH$_3$)$_2$). |
| IR (neat), cm$^{-1}$: | |
| HRMS (ESI): | Calcd for (C$_{21}$H$_{24}$N$_2$O$_5$ + H)$^+$: 385.1763<br>Found: 385.1747. |

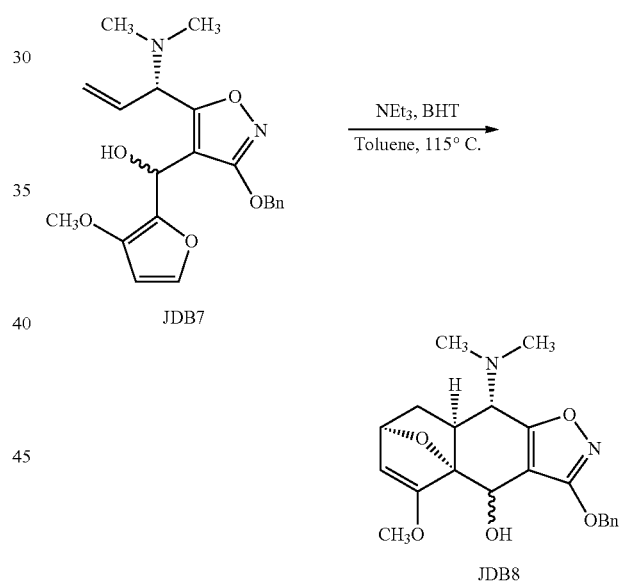

JDB7

JDB8

Diels-Alder Adduct JDB8:

A solution of furyl alcohol JDB7 (626 mg, 1.63 mmol, 1 equiv), triethylamine (457 µL, 3.26 mmol, 2.00 equiv) and 2,6-di-tert-butyl-4-methylphenol (10 mg) in toluene (23.3 mL) was heated to 115° C. in a sealed tube for 36 h. The product solution was concentrated and the residue obtained (a mixture of Diels-Alder adducts) was used in the subsequent step without further purification.

| | |
|---|---|
| TLC (50% acetone-hexanes) | $R_f$ = 0.23-0.35 (all isomers) (UV, CAM). |
| HRMS (ESI): | Calcd for (C$_{21}$H$_{24}$N$_2$O$_5$ + H)$^+$: 385.1763<br>Found: 385.1767. |

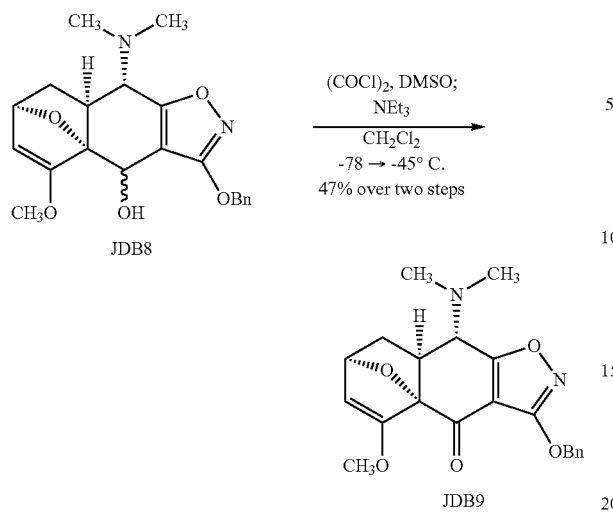

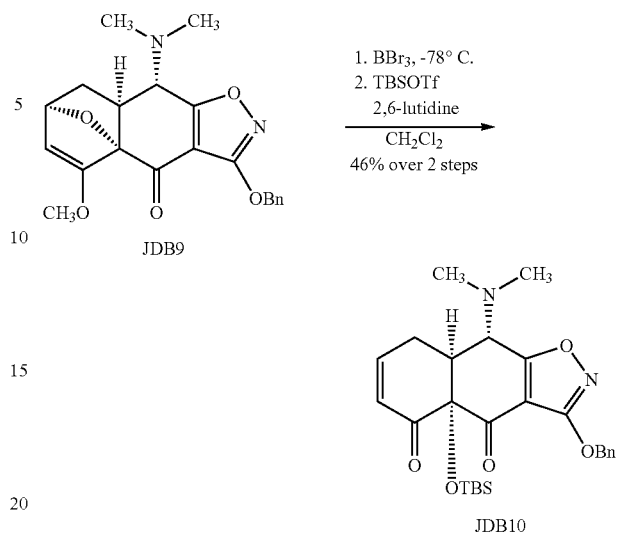

Ketone JDB9:

Dimethyl sulfoxide (290 μL, 4.08 mmol, 2.50 equiv) was added dropwise to a solution of oxalyl chloride (216 μL, 2.45 mmol, 1.50 equiv) in dichloromethane (10 mL) at −78° C. The reaction solution was stirred for 15 min and a solution of alcohol JDB8 (crude material from previous reaction, 0.177 mmol, 1 equiv) in dichloromethane (4 mL) was then added dropwise via cannula to the cold reaction solution. The flask containing the alcohol JDB8 was rinsed with dichloromethane (2 mL) and the rinse solution was transferred to the reaction flask, via cannula. The reaction solution was stirred at −78° C. for 25 min and then triethylamine (1.14 mL, 8.15 mmol, 5.00 equiv) was added. The reaction solution then was allowed to warm to −45° C. over 45 min and saturated aqueous sodium bicarbonate solution (5 mL) was added. The product solution was partitioned between aqueous potassium phosphate buffer (pH 7.0, 0.05 M, 20 mL) and dichloromethane (50 mL). The aqueous layer was further extracted with dichloromethane (25 mL). The organic layers were combined and the combined layers were dried over sodium sulfate. The solids were filtered and the filtered solution was concentrated. The residue obtained was purified by flash-column chromatography on silica gel (30% acetone-hexanes) to furnish the ketone JDB9 (294 mg, 47% over two steps, single diastereomer) as a white solid.

| TLC (50% acetone-hexanes) | $R_f$ = 0.33 (UV, CAM). |
|---|---|
| $^1$HNMR (500 MHz, CDCl$_3$), δ: | 7.51 (d, 2H, J = 6.8 Hz, ArH), 7.40-7.34 (m, 3H, ArH), 5.37 (AB quartet, 2H, J = 12.2 Hz, Δν = 9.0 Hz, —OCH$_2$Ar), 5.31 (d, 1H, J = 2.0 Hz, C═CH), 5.05 (dd, 1H, J = 4.4, 2.4 Hz, C═CHCH), 3.52 (s, 3H, OCH$_3$), 3.46 (d, 1H, J = 11.2 Hz, CH(NCH$_3$)$_2$), 2.81 (ddd, 1H, J = 11.2, 9.0, 4.9 Hz, CHCH(NCH$_3$)$_2$), 2.49 (s, 6H, NCH$_3$)$_2$), 2.37 (ddd, 1H, J = 11.2, 9.0, 4.4 Hz, CHHCHCHNCH$_3$)$_2$), 1.49 (dd, 1H, J = 11.2, 4.9 Hz, CHHCHCHNCH$_3$)$_2$). |
| IR (neat), cm$^{-1}$: | 2944 (w), 2875 (w), 2838 (w), 2796 (w), 1710 (s), 1632 (s), 1580 (s), 1505 (s), 1453 (s), 1370 (m), 1339 (m), 1308 (m), 1023 (m), 949 (s). |
| HRMS (ESI): | Calc'd for (C$_{21}$H$_{22}$N$_2$O$_3$ + H)$^+$: 383.1607 Found: 383.1593. |

Protected Enone 10:

A solution of boron tribromide in dichloromethane (1.0 M, 1.54 mL, 1.54 mmol, 2.00 equiv) was added to a solution of ketone JDB9 (294 mg, 0.770 mmol, 1 equiv) in dichloromethane (7.7 mL) at −78° C. The yellow reaction solution was stirred for 12 min, then was partitioned between aqueous potassium phosphate buffer (pH 7.0, 0.05 M, 30 mL) and dichloromethane (50 mL). The aqueous layer was separated and further extracted with dichloromethane (30 mL). The organic layers were combined and the combined layers were dried over sodium sulfate. The solids were filtered and the filtrate was concentrated. The residue obtained was dissolved in dichloromethane (15.4 mL) and the resulting solution was cooled to 0° C. 2,6-Lutidine (382 μL, 3.48 mmol, 4.5 equiv) and tert-butyldimethylsilyl trifluoromethanesulfonate (444 μL, 1.93 mmol, 2.5 equiv) were added sequentially to the cooled solution. The reaction solution was stirred at 0° C. for 5 min and then the cooling bath was removed. The reaction solution was stirred at 23° C. for 65 min, then was partitioned between aqueous potassium phosphate buffer (pH 7.0, 0.05 M, 20 mL) and dichloromethane (40 mL). The aqueous layer was separated and further extracted with dichloromethane (20 mL). The organic layers were combined and the combined layers were dried over sodium sulfate. The solids were filtered and the filtrate was concentrated. The residue obtained was purified by flash-column chromatography on silica gel (2.5% ethyl acetate-hexanes, grading to 7.5% ethyl acetate-hexanes) to furnish the enone JDB10 (170 mg, 46% over two steps) as a white solid.

| TLC (20% ethyl acetate-hexanes) | $R_f$ = 0.34 (UV, CAM). |
|---|---|
| $^1$HNMR (500 MHz, CDCl$_3$), δ | 7.51 (d, 2H, J = 1.5 Hz, ArH), 7.50-7.34 (m, 3H, ArH), 6.94 (m, 1H, ═CHCH$_2$), 6.10 (ddd, 1H, J = 10.3, 1.5, 1.5 Hz, ═CHC(O)), 5.36 (m, 2H, OCH$_2$Ph), 3.79 (d, 1H, J = 10.7 Hz, CHN(CH$_3$)$_2$), 2.83 (m, 2H, ═CHCH$_2$), 2.78 (m, 1H, CHCHN(CH$_3$)$_2$), 2.46 (s, 6H, N(CH$_3$)$_2$), 0.84 (s, 9H, SiC(CH$_3$)$_3$), 0.27 (s, 3H, SiCH$_3$), 0.06 (s, 3H, SiCH$_3$). |
| $^{13}$CNMR (100 MHz, CDCl$_3$), δ: | 193.4, 187.9, 181.6, 167.7, 149.5, 135.2, 128.8, 128.8, 128.8, 128.6, 108.6, 83.5, 72.8, 59.8, 48.1, |

|         |                                                                                                          |
|---------|----------------------------------------------------------------------------------------------------------|
|         | 42.2, 26.3, 25.8, 19.3, −2.2, −3.8.                                                                      |
| IR (neat), cm⁻¹: | 2942 (s), 1719 (s), 1678 (s), 1602 (m), 1510 (s), 1053 (s), 733 (s).                            |
| HRMS (ESI): | Calcd for ($C_{26}H_{34}N_2O_5$+ H)⁺: 483.2315 |
|         | Found: 483.2321. |

Example 2

Alternative Synthesis of Chiral Enone

General Experimental Procedures. All reactions were performed in flame-dried glassware fitted with rubber septa under a positive pressure of argon, unless otherwise noted. Air- and moisture-sensitive liquids were transferred via syringe or stainless steel cannula. Organic solutions were concentrated by rotary evaporation (house vacuum, ca. 25-40 Torr) at ambient temperature. Analytical thin-layer chromatography was performed using glass plates pre-coated with silica gel (0.25 mm, 60 Å pore size, 230-400 mesh, Merck KGA) impregnated with a fluorescent indicator (254 nm). TLC plates were visualized by exposure to ultraviolet light (UV), and then were stained by submersion in aqueous ceric ammonium molybdate solution (CAM), basic aqueous potassium permanganate ($KMnO_4$), or an acidic solution of p-anisaldehyde in ethanol, followed by brief heating on a hot plate (~170° C., 10-15 s). Flash-column chromatography was performed as described by Still et al. (J. Org. Chem. 1978, 43, 2923), employing silica gel (60-Å pore size, 32-63 μm, standard grade, Sorbent Technologies).

Materials. Commercial reagents and solvents were used with the following exceptions. Tetrahydrofuran and 1,4-dioxane were distilled under nitrogen from sodium-benzophenone ketyl. The molarity of commercial solutions of n-butyllithium was determined by titration against standard solutions of diphenylacetic acid (average of three determinations) (Kofron et al., J. Org. Chem. 1976, 41, 1879).

Instrumentation. Proton magnetic resonance (¹H NMR) spectra were recorded on Varian Mercury 400 (400 MHz), Varian INOVA 500 (500 MHz), or Varian INOVA 600 (600 MHz) NMR spectrometers at 25° C. Proton chemical shifts are expressed in parts per million (ppm, δ scale) and are referenced to residual protium in the NMR solvent ($CHCl_3$: δ 7.26, $C_6HD_5$: δ 7.15). Data are represented as follows: chemical shift, multiplicity (s=singlet, d=doublet, t=triplet, q=quartet, m=multiplet, br=broad), integration, and coupling constant (J) in Hertz (Hz). Carbon nuclear magnetic resonance (¹³C NMR) spectra were recorded on Varian Mercury 400 (100 MHz) or Varian INOVA 500 (125 MHz) NMR spectrometers at 25° C. Carbon chemical shifts are expressed in parts per million (ppm, δ scale) and are referenced to the carbon resonance of the NMR solvent ($CDCl_3$: δ 77.0, C6D_6: δ 128). Samples for infrared (IR) spectroscopy were prepared as neat films by evaporation of dichloromethane solutions; infrared spectra were recorded using a Perkin-Elmer 1600 FT-IR spectrophotometer and were referenced to an internal polystyrene standard. Data are represented as follows: frequency of absorption (cm⁻¹) and intensity of absorption (s=strong, m=medium, w=weak, br=broad). High-resolution mass spectra were obtained at Harvard University Mass Spectrometry Facility.

Morpholinylnorephedrine (3a):

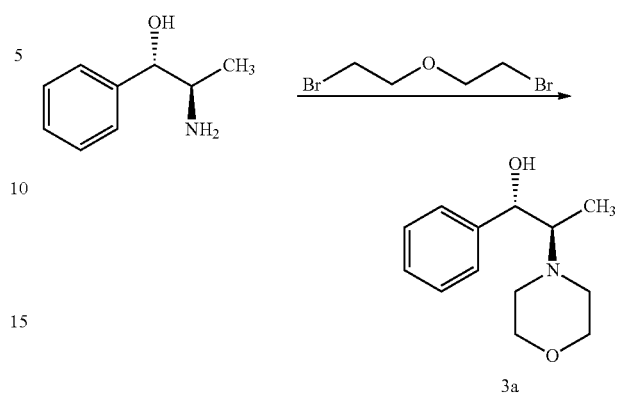

The published protocol (Pierce et al., J. Org. Chem. 1998, 63, 8536-8543) for the preparation of pyrrolidinylnorephedrine from norephedrine and 1,4-dibromobutane was used for guidance for this procedure. A 500-mL, one-necked, round-bottomed flask containing a Teflon-coated magnetic stirbar was charged with (1S,2R)-norephedrine (36.2 g, 239 mmol, 1 equiv), 2-bromoethyl ether (65.7 g, 263 mmol, 1.10 equiv), sodium bicarbonate (44.3 g, 527 mmol, 2.20 equiv) and toluene (191 mL), then was fitted with a reflux condenser. The system was flushed with argon and heated at 115° C. in an oil bath for 22.5 h. After cooling to 23° C. the reaction mixture was filtered, and the filtrate was washed with water (100 mL). The washed product solution was then extracted into aqueous citric acid solution (30% by weight, 2×200 mL). The citric acid layers were combined, cooled in an ice-water bath, and brought to pH 13 by slow addition of aqueous sodium hydroxide solution (6 N). The basic aqueous mixture was extracted with toluene (3×300 mL). The toluene layers were combined and washed sequentially with water (200 mL) and saturated aqueous sodium chloride solution (300 mL). The washed solution was dried over sodium sulfate and the solids were filtered. The filtrate was concentrated (30-40 torr, bath temp 45° C.) to furnish (1S,2R)-N-morpholinylnorephedrine (49.5 g, 93%) as a white, crystalline solid.

| ¹HNMR (500 MHz, CDCl₃), δ: | 7.32-7.20 (m, 5H, ArH), 4.88 (d, 1H, J = 3.9 Hz, CHOH), 3.69 (t, 4H, J = 4.88 Hz, CH₂OCH₂), 3.57 (br s, 1H, OH), 2.67-2.52 (5H, m, CH₃CHNR₂, CH₂NCH₂), 0.82 (3H, d, J = 6.8 Hz, CH₃). |
|---|---|
| ¹³CNMR (100 MHz, CDCl₃), δ: | 141.8, 128.0, 126.8, 125.8, 71.6, 67.3, 64.8, 50.8, 9.7. |
| IR (neat), cm⁻¹: | 3425 (bs), 2960 (m), 2908 (m), 2855 (m), 2816 (m), 1450 (s), 1116 (s). |
| HRMS (ESI): | Calcd for ($C_{13}H_{13}NO_3$ + H)⁺: 222.1494 |
|   | Found: 222.1487 |

Divinylzinc:

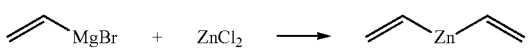

A 5-L, two-necked, round-bottomed flask with a coarse fritted funnel fused at a 45° angle was equipped with a mechanical stirrer. The system was flame-dried, flushed with argon, and charged with a solution of zinc chloride in diethyl ether (1.0 M, 1 L, 1 mol, 1 equiv). A solution of vinylmagnesium bromide in tetrahydrofuran (1.0 M, 2 L, 2 mol, 2 equiv) was added via cannula over 2.5 h. A gray solid precipitated throughout the addition. The reaction mixture was stirred at 23° C. for 2 h, and then dioxane (600 mL) was added via cannula. The reaction mixture was stirred at 23° C. for an additional 1 h. A 3-L, one-necked, flame-dried flask was attached to the joint at the end of the funnel and the mechanical stirrer was replaced by a glass stopper. The entire apparatus was then turned 135° to allow the reaction mixture to filter into the 3-L flask to furnish a yellow solution of divinylzinc (assumed to be 0.28M, 2.25 L). The divinylzinc solution could be used directly in the next reaction, or stored at −20° C. for 2 months with no loss in yield or enantioselectivity during the enantioselective addition described below.

A.

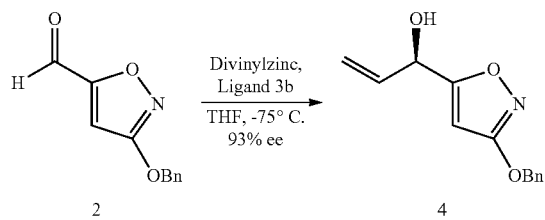

B.

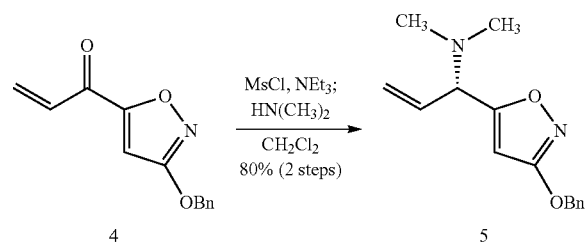

Tertiary Amine 5:

A. A 12-L, Morton-style, four-necked flask was equipped with a mechanical stirrer and a thermocouple. The system was flushed with argon and charged with a solution of (1S, 2R)-morpholinylnorephedrine (163.3 g, 738 mmol, 2.00 equiv) in toluene (2.0 L). The solution was cooled to 0° C. in a dry ice-acetone bath, and then a solution of n-butyllithium in hexanes (2.50 M, 295 mL, 738 mmol, 2.00 equiv) was added via cannula. The reaction solution was stirred for an additional 30 min at 0° C. after the addition, and then a solution of divinylzinc (0.28 M, prepared as described above, 2.64 L, 738 mmol, 2.0 equiv) was added via cannula over 70 min. The reaction mixture was stirred at 0° C. for 1 h, and then was cooled to −75° C. by addition of dry ice to the cooling bath. A solution of aldehyde 2 (Riess et al., Eur. J. Org. Chem. 1998, 473-47) (75 g, 369 mmol, 1 equiv) in toluene (300 mL) was added to the reaction mixture at −75° C. over 50 min. The reaction mixture was stirred at −75° C. for 40 min, and then the cooling bath was removed. After warming to −30° C., aqueous citric acid solution (30% by weight, 2 L) was added. The reaction mixture was allowed to warm to 23° C. and then was partitioned. The organic layer was washed sequentially with water (700 mL) and brine (700 mL), dried over sodium sulfate, and the dried solution was filtered. The filtrate was concentrated (30-40 torr, 45° C. bath temp) to furnish the allylic alcohol 4 (93% ee by Mosher ester analysis (Dale, J. A.; Mosher, H. S. J. Am. Chem. Soc. 1973, 95, 512-519)) as a pale yellow oil which was used directly in the subsequent reaction without further purification. An analytical sample was prepared by flash-column chromatography on silica gel (30% ethyl acetate-hexanes) to furnish the allylic alcohol 4 as a clear, colorless oil.

B. A 12-L, Morton-style, four-necked flask was equipped with a mechanical stirrer and a thermocouple. The system was flushed with argon and charged with a solution of unpurified allylic alcohol 4 (369 mmol, 1 equiv) and triethylamine (67.3 mL, 480 mmol, 1.30 equiv) in dichloromethane (3.7 L). The solution was cooled to −12° C. in a dry ice-acetone bath, and then methanesulfonyl chloride (33.5 mL, 424 mmol, 1.15 equiv) was added dropwise via syringe. After stirring at −12° C. for 30 min, the reaction mixture was cooled to −30° C. by addition of dry ice to the cooling bath and then a solution of dimethylamine in tetrahydrofuran (2.0 M, 1.1 L, 2.2 mol, 6.0 equiv) was added via cannula over 70 min. The reaction mixture was allowed to warm slowly to 15° C. over 7 h, and then was concentrated to a volume of 1.5 L. The reaction mixture was partitioned between aqueous potassium phosphate buffer (pH 7.0, 0.05 M, 2 L) and dichloromethane (1.5 L). The aqueous layer was further extracted with dichloromethane (1 L). The organic layers were combined and the combined layers were dried over sodium sulfate. The solids were filtered and the filtrate was concentrated. The residue obtained was partitioned between diethyl ether (700 mL) and aqueous hydrochloric acid solution (1.0 M, 1 L). The hydrochloric acid extraction was cooled in an ice-water bath and brought to pH 13 by slow addition of aqueous sodium hydroxide solution (6.0 M). The basic aqueous mixture was extracted with diethyl ether (2×700 mL) and the organic layers were combined. The combined organic layers were washed with saturated aqueous sodium chloride solution, dried over sodium sulfate, and the dried solution was filtered. The filtrate was concentrated, and the residue was purified by flash-column chromatography on silica gel (3% methanol-dichloromethane) to furnish the allylic amine 5 (76.3 g, 80% over two steps) as a pale yellow oil.

Recovery of morpholinylnorephedrine (3a). The aqueous citric acid layer from part A was cooled in an ice-water bath and brought to pH 13 by slow addition of aqueous sodium hydroxide solution (6 N). The basic aqueous mixture was extracted with toluene (2×1.5 L). The toluene layers were combined and washed sequentially with water (500 mL) and saturated aqueous sodium chloride solution (500 mL). The washed solution was dried over sodium sulfate and the solids were filtered. The filtrate was concentrated (30-40 ton, bath temp 45° C.) to furnish (1S,2R)-N-morpholinylnorephedrine (161.5 g, 99%) as a white, crystalline solid.

Allylic Alcohol 4:

| TLC (30% ethyl acetate-hexanes) | $R_f = 0.25$ (UV, CAM). |
|---|---|
| $^1$HNMR (500 MHz, CDCl$_3$), δ: | 7.43-7.34 (m, 5H, ArH), 6.04 (ddd, 1H, J = 17.1, 10.3, 5.9 Hz, CH$_2$=CH), 5.87 (s, 1H, IsoxH), 5.46 (d, 1H, J = 17.1, trans-CHH=CH), 5.34 (d, 1H, J = 10.3 Hz, cis-CHH=CH), 5.24 (s, 2H, OCH$_2$Ar), 5.22 (t, 1H, J = 5.34 Hz, CHOH), 2.25 (br s, 1H, OH). |
| $^{13}$CNMR (100 MHz, CDCl$_3$), δ: | 173.3, 171.6, 135.7, 135.3, 128.6, 128.5, 128.2, 118.0, 92.9, 71.6, 68.3. |
| IR (neat), cm$^{-1}$: | 3361 (bs), 1615 (s), 1503 (s), 1451 (s), 1364 (s) 1216 (w), 1119 (w), 1036 (s), 986 (s), 932 (s). |
| HRMS (ESI): | Calcd for (C$_{13}$H$_{13}$NO$_3$ + H)$^+$: 232.0973 Found: 232.0973. |

Tertiary Amine 5:

| | |
|---|---|
| TLC (40% acetone-hexanes) | $R_f$ = 0.42 (UV, CAM). |
| $^1$HNMR (500 MHz, CDCl$_3$), δ: | 7.46-7.36 (m, 5H, ArH), 5.94 (m, 1H, CH$_2$═CH), 5.81 (s, 1H, IsoxH), 5.32-5.29 (m, 2H, CHH═CH), 5.26 (s, 2H, OCH$_2$Ar), 4.00 (d, 1H, J = 7.8 Hz, CHN(CH$_3$)$_2$), 2.27 (s, 6H, N(CH$_3$)$_2$). |
| $^{13}$CNMR (100 MHz, CDCl$_3$), δ: | 172.5, 171.6, 135.8, 134.1, 128.6, 128.5, 128.3, 119.5, 93.9, 71.5, 66.3, 42.3. |
| IR (neat), cm$^{-1}$: | 2946 (w), 2869 (w), 2827 (w), 2782 (w), 1607 (s), 1501 (s), 1449 (s), 1366 (s), 1138 (w), 1036 (s), 992 (s), 926(s). |
| HRMS (ESI): | Calcd for (C$_{15}$H$_{18}$N$_2$O$_2$ + H)$^+$: 259.1446<br>Found: 259.1436. |

Diels Alder Precursors (7a and 7b):

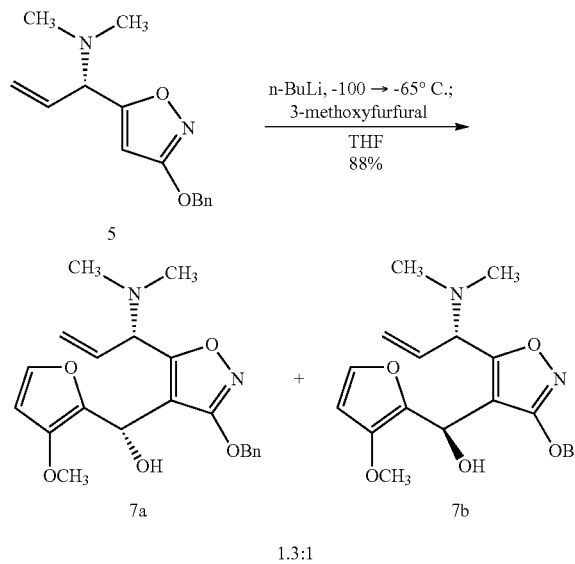

An oven-dried, 5-L, three-necked, round-bottomed flask was equipped with a mechanical stirrer and thermocouple, and then was charged with a solution of isoxazole 5 (74.5 g, 288 mmol, 1 equiv) in tetrahydrofuran (1.44 L). The solution was cooled to −100° C. in a liquid dinitrogen-ethanol bath, and then a solution of n-butyllithium in hexanes (2.41 M, 138 mL, 332 mmol, 1.15 equiv) was added dropwise over 50 min. The resulting dark-yellow solution was allowed to warm to −65° C. over 22 min, at which point the mixture had become reddish-brown. The mixture was stirred at −65° C. for 80 min and then a solution of 3-methoxyfurfural (40 g, 317 mmol, 1.1 equiv) in tetrahydrofuran (350 mL) was added dropwise via cannula. The reaction mixture was allowed to warm to −50° C. over 50 min and then aqueous potassium phosphate solution (pH 7.0, 0.05 M, 1.5 L) was added. The product solution was extracted with dichloromethane (1×2 L, 2×700 mL). The organic layers were combined and the combined solution was dried over sodium sulfate. The solids were filtered and the filtrate was concentrated. The residue obtained was purified by flash-column chromatography on silica gel (70% diethyl ether-pentane) to furnish the Diels-Alder precursors 7a and 7b (97.6 g, 88%, 1.3:1 mixture of epimers) as a pale red oil. In practice, the two epimers were not separated before use in the subsequent Diels-Alder reaction. Analytical samples of the separated epimers were prepared by radial chromatography (50% acetone-hexanes) for characterization purposes.

Diels-Alder Precursor 7a:

| | |
|---|---|
| TLC (60% diethyl ether-pentane) | $R_f$ = 0.16 (UV, CAM) |
| $^1$HNMR (500 MHz, CDCl$_3$), δ: | 8.15 (s, 1H, OH), 7.33-7.23 (m, 5H, ArH), 7.13 (d, 1H, J = 1.95, FurH), 6.23 (d, 1H, J = 1.95, FurH), 6.23-6.10 (ddd, 1H, J = 17.1, 9.8, 9.8 Hz, CH$_2$═CH), 5.76 (s, 1H, CHOH), 5.38-5.35 (m, 2H, CHH═CH), 5.16 (AB quartet, 2H, J = 12.2 Hz, Δv = 8.1 Hz, —OCH2Ar), 4.00 (d, 1H, J = 9.3 Hz, CHN(CH$_3$)$_2$), 3.59 (s, 3H, OCH$_3$), 2.32 (s, 1H, CHN(CH$_3$)$_2$). |
| $^{13}$CNMR (100 MHz, CDCl$_3$), δ: | 169.1, 167.8, 144.5, 140.4, 137.9, 135.9, 132.1, 128.3, 128.0, 127.5, 121.0, 107.0, 102.7, 71.1, 68.3, 58.9, 58.3, 42.1. |
| IR (neat), cm$^{-1}$: | 2875 (w), 2846 (w), 2792 (w), 1632 (m), 1511 (m), 1451 (m), 1368 (m), 1106 (m), 1040 (m), 905 (s). |
| HRMS (ESI): | Calcd for (C$_{21}$H$_{24}$N$_2$O$_5$ + H)$^+$: 385.1763<br>Found: 385.1747. |

Diels-Alder Precursor 7b:

| | |
|---|---|
| TLC (60% diethyl ether-pentane) | $R_f$ = 0.16 (UV, CAM) |
| $^1$HNMR (500 MHz, CDCl$_3$), δ: | 8.09 (s, 1H, OH), 7.33-7.23 (m, 5H, ArH), 7.12 (d, 1H, J = 1.95, FurH), 6.25 (d, 1H, J = 1.95, FurH), 6.19-6.10 (ddd, 1H, J = 16.9, 9.6, 9.6 Hz, CH$_2$αCH), 5.72 (s, 1H, CHOH), 5.41-5.37 (m, 2H, CHHαCH), 5.20 (AB quartet, 2H, J = 12.2 Hz, Δv = 8.1 Hz, —OCH$_2$Ar), 4.18 (d, 1H, J = 9.6 Hz, |

| | |
|---|---|
| | CHN(CH$_3$)$_2$), 3.61 (s, 3H, OCH$_3$), 2.32 (s, 1H, CHN(CH$_3$)$_2$). |
| $^{13}$CNMR (100 MHz, CDCl$_3$), δ: | 169.1, 168.6, 144.2, 140.2, 138.8, 135.9, 131.3, 128.3, 128.1, 127.6, 121.3, 107.3, 102.9, 71.1, 67.8, 59.1, 57.9, 41.9. |
| IR (neat), cm$^{-1}$: | 2875 (w), 2846 (w), 2792 (w), 1632 (m), 1511 (m), 1451 (m), 1368 (m), 1106 (m), 1040 (m), 905(s). |
| HRMS (ESI): | Calcd for (C$_{21}$H$_{24}$N$_2$O$_5$ + H)$^+$: 385.1763 <br> Found: 385.1747 |

Diels-Alder Adducts (9-12):

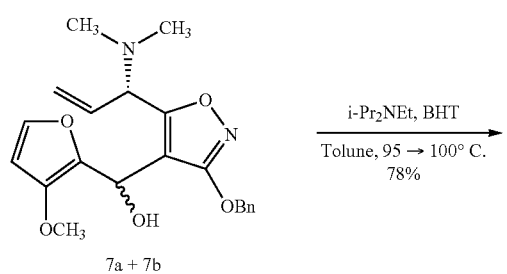

7a + 7b i-Pr$_2$NEt, BHT
Tolune, 95 → 100° C.
78%

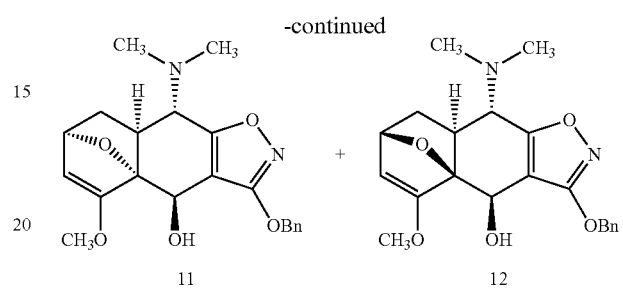

11      12

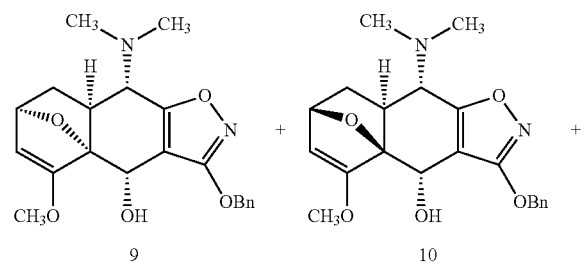

9      10

A 5-L, two-necked, round-bottomed flask was charged with a solution of Diels-Alder precursors 7a and 7b (97.6 g, 254 mmol, 1 equiv) and 2,6-di-tert-butyl-4-methylphenol (200 mg) in toluene (2.54 L). The solution was cooled to 0° C. in an ice bath and vacuum was applied (~1 torr). Gas evolution ceased after 60 min and the solution was back-filled with argon. N,N-diisopropylethylamine (88.5 mL, 508 mmol, 2.00 equiv) was added, the flask was equipped with a reflux condenser and thermometer, and the reaction mixture was warmed to 95° C. in a heating mantle. After stirring for 105 h, the reaction mixture was warmed to 110° C. for 23 h. The product solution was cooled to 23° C. and loaded directly onto a silica gel plug (14 cm diameter, 17 cm length). The toluene solvent was eluted with 15% acetone-hexanes and then the mixture of Diels-Alder products were eluted by grading to 65% acetone hexanes to give a mixture which was carried on directly to the Swern oxidation (76.6 g, 78%). Analytical samples of the four Diels-Alder products were prepared by radial chromatography (20% acetone-dichloromethane grading to 30% acetone-dichloromethane.

TLC (50% acetone-hexanes) R$_f$=0.23-0.35 (all isomers) (UV, CAM).

Endo Adduct 9:

| | |
|---|---|
| $^1$HNMR (500 MHz, CDCl$_3$), δ: | 7.48 (d, 2H, J = 7.7 Hz, ArH), 7.41-7.35 (m, 3H, ArH), 5.33 (s, 2H, OCH$_2$Ar), 5.23 (d, 1H, J = 2.4 Hz, CHαCOCH$_3$), 5.03 (d, 1H, J = 2.4 Hz, CHOH), 5.00 (dd, 1H, J = 4.4, 2.4 Hz, CHCH═COCH$_3$), 3.44 (s, 3H, OCH$_3$), 3.10 (d, 1H, J = 11.2 Hz, CHN(CH$_3$)$_2$), 2.82 (ddd, 1H, J = 11.2, 9.3, 4.4 Hz, CHCHN(CH$_3$)$_2$), 2.48 (s, 6H, CHN(CH$_3$)$_2$), 2.35 (ddd, 1H, J = 11.2, 9.3, 4.4 Hz, CHHCHCHN(CH$_3$)$_2$), 2.28 (d, 1H, J = 2.4 Hz, OH), 1.38 (dd, 1H, J = 11.2, 4.4 Hz, CHHCHCHN(CH$_3$)$_2$). |
| $^{13}$CNMR (100 MHz, CDCl$_3$), δ: | 173.5, 169.5, 162.8, 135.8, 128.5, 128.5, 128.4, 128.3, 108.5, 102.2, 87.4, 79.3, 71.6, 64.2, 58.9, 57.5, 41.9, 34.4, 33.0. |
| HRMS (ESI): | Calcd for (C$_{21}$H$_{24}$N$_2$O$_5$ + H)$^+$: 385.1763 <br> Found: 385.1752 |

Exo Adduct 10:

| | |
|---|---|
| $^1$HNMR (500 MHz, CDCl$_3$), δ: | 7.45 (d, 2H, J = 7.3 Hz, ArH), 7.39-7.33 (m, 3H, ArH), 5.30 (s, 2H, OCH$_2$Ar), 5.28 (d, 1H, J = 1.9 Hz, CH=COCH3), 5.17 (s, 1H, CHOH), 4.88 (dd, 1H, J = 4.4, 2.0 Hz, CHCH=COCH$_3$), 3.79-3.77 (m, 2H, OH, CHN(CH$_3$)$_2$), 3.68 (s, 3H, OCH$_3$), 2.43-2.38 (m, 7H, CHN(CH$_3$)$_2$, CHCHN(CH$_3$)$_2$), 2.24 (dd, 1H, J = 11.5, 8.1 Hz, CHHCHCHN(CH$_3$)$_2$), 1.96 (ddd, 1H, J = 11.2, 3.9, 3.9 Hz, CHHCHCHN(CH$_3$)$_2$). |
| $^{13}$CNMR (125 MHz, CDCl$_3$), δ: | 169.9, 169.1, 166.7, 135.8, 128.5, 128.3, 128.3, 106.9, 103.7, 86.7, 76.9, 71.5, 65.5, 61.4, 58.1, 43.4, 41.9, 35.5. |
| HRMS (ESI): | Calcd for (C$_{21}$H$_{24}$N$_2$O$_5$ + H)$^+$: 385.1763<br>Found: 385.1776 |

Endo Adduct 11:

| | |
|---|---|
| $^1$HNMR (500 MHz, CDCl$_3$), δ: | 7.49 (d, 2H, J = 7.0 Hz, ArH), 7.40-7.34 (m, 3H, ArH), 5.36-5.31 (m, 3H, OCH2Ar, CH=COCH3), 5.07 (dd, 1H, J = 9.0, 2.0 Hz, CHOH), 4.99 (dd, 1H, J = 4.1, 2.2 Hz, CHCH=COCH$_3$), 3.57 (s, 3H, OCH$_3$), 3.22 (dd, 1H, J = 11.2, 2.0 Hz, CHN(CH$_3$)$_2$), 2.48 (s, 1H, J = 9.0 Hz, OH), 2.43-2.33 (m, 7H, CHN(CH$_3$)$_2$, CHCHN(CH$_3$)$_2$), 2.31 (ddd, 1H, J = 11.5, 9.3, 4.1 Hz, CHHCHCHN(CH$_3$)$_2$), 1.40 (dd, 1H, J = 11.5, 3.9 Hz, CHHCHCHN(CH$_3$)$_2$). |
| $^{13}$CNMR (100 MHz, CDCl$_3$), δ: | 171.4, 169.3, 162.5, 135.8, 128.6, 128.5, 128.4, 128.2, 108.5, 103.4, 90.0, 79.1, 71.6, 65.1, 63.7, 57.9, 41.8, 41.8, 33.1. |
| HRMS (ESI): | Calcd for (C$_{21}$H$_{24}$N$_2$O$_5$ + H)$^+$: 385.1763<br>Found: 385.1755 |

Exo Adduct 12:

| | |
|---|---|
| $^1$HNMR (500 MHz, C$_6$D$_6$), δ: | 7.35 (d, 2H, J = 7.3 Hz, ArH), 7.08 (t, 2H, J = 7.8 Hz, ArH), 7.03 (t, 1H, J = 7 Hz, ArH), 5.57 (dd, 1H, J = 9.8, 2.0 Hz, CHOH), 5.31 (AB quartet, 2H, J = 12.2 Hz, Av = 15.1 Hz, —OCH$_2$Ar), 4.62 (dd, 1H, J = 4.1, 2.0 Hz, CHCH=COCH$_3$), 4.59 (d, 1H, J = 2.0 Hz, CH=COCH$_3$), 3.52 (dd, 1H, J = 9.8, 2.0 Hz, CHN(CH$_3$)$_2$), 3.02 (s, 3H, OCH$_3$), 2.58 (d, 1H, J = 9.8 Hz, OH), 2.23 (s, 6H, CHN(CH$_3$)$_2$), 2.02 (ddd, 1H, J = 9.8, 7.8, 2.4 Hz, CHCHN(CH$_3$)$_2$), 1.78 (ddd, 1H, J = 11.6, 4.1, 2.4 Hz, CHHCHCHN(CH$_3$)$_2$), 1.69 (dd, 1H, J = 11.6, 7.8 Hz, CHHCHCHN(CH$_3$)$_2$). |
| $^{13}$CNMR (100 MHz, C$_6$D$_6$), δ: | 170.5, 169.6, 164.5, 136.7, 128.6, 128.3, 128.3, 107.9, 101.3, 89.1, 77.9, 71.6, 64.7, 59.4, 57.1, 42.7, 41.7, 40.2. |
| HRMS (ESI): | Calcd for (C$_{21}$H$_{24}$N$_2$O$_5$ + H)$^+$: 385.1763<br>Found: 385.1751 |

Ketone (8):

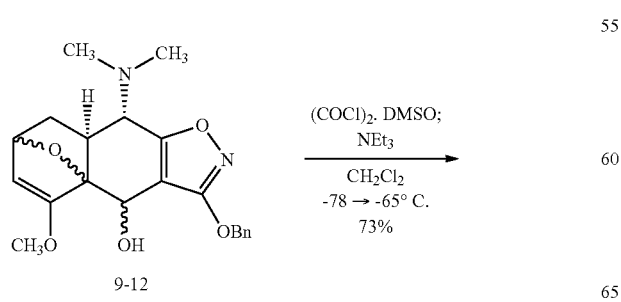

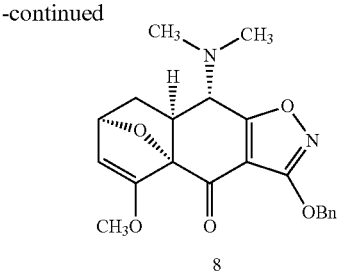

A 5-L, three-necked, round-bottomed flask was oven-dried and flushed with argon. The flask was equipped with a mechanical stirrer and thermocouple, and then was charged with a solution of oxalyl chloride (24.6 mL, 279 mmol, 1.40 equiv) in dichloromethane (1 L). The solution was cooled to −78° C. in a dry ice-acetone bath, and then a solution of dimethyl sulfoxide (35.3 mL, 498 mmol, 2.50 equiv) in dichloromethane (500 mL) was added dropwise over 90 min. The reaction solution was stirred for 10 min and then a solution of Diels-Alder precursors 9-12 (76.6 g, 199 mmol, 1 equiv) in dichloromethane (500 mL) was added dropwise via cannula to the cold reaction solution. The flask containing 9-12 was rinsed with dichloromethane (25 mL) and the rinse solution was transferred to the reaction flask, via cannula. The reaction solution was stirred at −78° C. for 25 min and then triethylamine (139 mL, 995 mmol, 5.00 equiv) was added. The reaction solution then was allowed to warm to −65° C. over 80 min and saturated aqueous sodium bicarbonate solution (700 mL) was added. The product solution was partitioned between aqueous potassium phosphate buffer (pH 7.0, 0.05 M, 500 mL) and dichloromethane (750 mL). The aqueous layer was further extracted with dichloromethane (500 mL). The organic layers were combined and the combined layers were dried over sodium sulfate. The solids were filtered and the filtrate was concentrated. The residue obtained was purified by flash-column chromatography on silica gel (30% acetone-hexanes, grading to 50% acetone-hexanes) to furnish the ketone 8 (55.4 g, 73%, single diastereomer) as a pale yellow solid. The exo product was also observed prior to chromatography, but fractions containing that product were discarded.

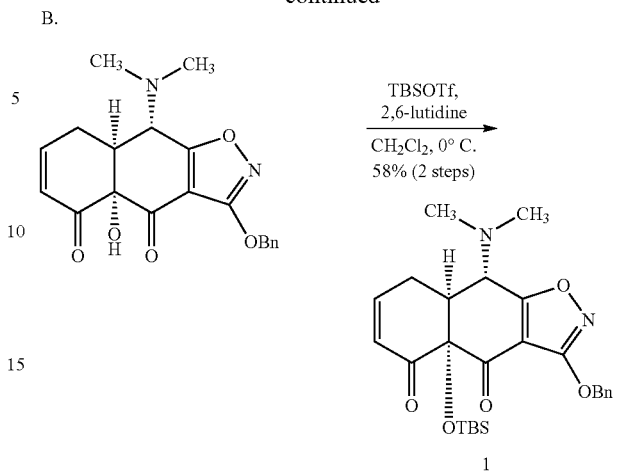

A. A 3-L, one-necked, round-bottomed flask was equipped with a Teflon-coated magnetic stirbar. The system was flame-dried and flushed with argon. The flask was charged with a solution of ketone 8 (55.4 g, 145 mmol, 1 equiv) in dichloromethane (1.45 L). The solution was cooled to −40° C. in a dry ice-acetone bath and a solution of boron trichloride in dichloromethane (1.0 M, 435 mL, 435 mmol, 3.00 equiv) was added. The yellow reaction mixture was stirred for 25 min, and then a solution of dipotassium hydrogenphosphate (120

| | |
|---|---|
| TLC (50% acetone-hexanes) | Rf = 0.33 (UV, CAM). |
| $^1$HNMR (500 MHz, CDCl$_3$), δ: | 7.51 (d, 2H, J = 6.8 Hz, ArH), 7.40-7.34 (m, 3H, ArH), 5.37 (AB quartet, 2H, J = 12.2 Hz, Δv = 9.0 Hz, —OCH$_2$Ar), 5.31 (d, 1H, J = 2.0 Hz, C+32CH), 5.05 (dd, 1H, J = 4.4, 2.4 Hz, C═CHCH), 3.52 (s, 3H, OCH$_3$), 3.46 (d, 1H, J = 11.2 Hz, CH(NCH$_3$)$_2$), 2.81 (ddd, 1H, J = 11.2, 9.0, 4.9 Hz, CHCH(NCH$_3$)$_2$), 2.49 (s, 6H, NCH$_3$)$_2$), 2.37 (ddd, 1H, J = 11.2, 9.0, 4.4 Hz, CHHCHCHNCH$_3$)$_2$), 1.49 (dd, 1H, J = 11.2, 4.9 Hz, CHHCHCHNCH$_3$)$_2$). |
| $^{13}$CNMR (100 MHz, C$_6$D$_6$), δ: | 184.5, 184.2, 167.5, 161.5, 135.1, 128.5, 128.5, 128.2, 110.5, 102.3, 89.5, 79.7, 72.3, 64.6, 57.8, 44.1, 41.8, 32.8. |
| IR (neat), cm$^{-1}$: | 2944 (w), 2875 (w), 2838 (w), 2796 (w), 1710 (s), 1632 (s), 1580 (s), 1505 (s), 1453 (s), 1370 (m), 1339 (m), 1308 (m), 1023 (m), 949 (s). |
| HRMS (ESI): | Calcd for (C$_{21}$H$_{22}$N$_2$O$_5$ + H)$^+$: 383.1607 Found: 383.1593 |

Enone 1:

A.

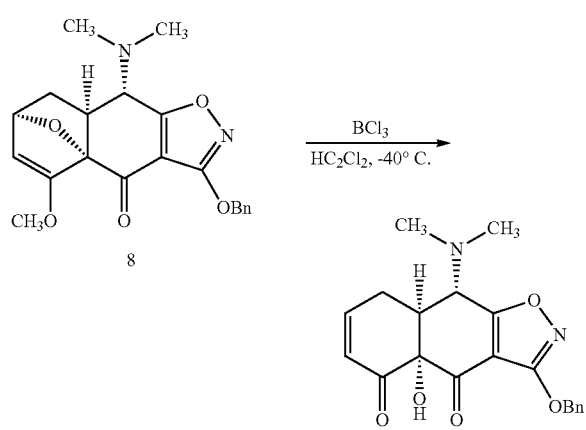

g) in water (1 L) was added and the cooling bath was removed. The pH of the reaction mixture was adjusted to 7 by addition of more dipotassium hydrogenphosphate in water. The mixture was partitioned and the aqueous layer was further extracted with dichloromethane (1 L). The organic layers were combined and the combined layers were dried over sodium sulfate. The solids were filtered and the filtrate was concentrated for use directly in the subsequent silylation step.

B. A 3-L, one-necked, round-bottomed flask was equipped with a Teflon-coated magnetic stirbar. The system was flame-dried and flushed with argon. The flask was charged with a solution of the residue obtained above (step A) in dichloromethane (1.45 L). The solution was cooled to 0° C. in an ice bath. 2,6-Lutidine (33.5 mL, 305 mmol, 2.10 equiv) and tert-butyldimethylsilyl trifluoromethanesulfonate (53.3 mL, 232 mmol, 1.6 equiv) were added sequentially to the cooled solution. The reaction solution was stirred at 0° C. for 15 min and then the cooling bath was removed. The reaction solution was stirred at 23° C. for 20 min, and then was partitioned between aqueous potassium phosphate buffer (pH 7.0, 0.05 M, 1 L) and dichloromethane (500 mL). The aqueous layer was separated and further extracted with dichloromethane (500 mL). The organic layers were combined and the combined layers were dried over sodium sulfate. The solids were filtered and the filtrate was concentrated. The residue obtained was purified by flash-column chromatography on silica gel (100% dichloromethane, grading to 2% ethyl acetate-dichloromethane) to furnish the enone 1 (40.2 g, 58% over two steps) as a light-yellow foam. The light-yellow foam was recrystallized from ethyl acetate-hexanes (1:4 by volume, 250 mL total volume) to give 27 g of an off-white solid (mp=150-151° C.). Further recrystallization of the mother liquor gave 7.2 g ($2^{nd}$ crop) and 1.9 g ($3^{rd}$ crop).

color formed during the addition. After stiffing for 20 min, the cooling bath was removed and saturated aqueous sodium bicarbonate solution (1.5 L) was added. The biphasic mixture was stirred vigorously for 6 hours, and then was partitioned. The aqueous layer was further extracted with dichloromethane (2×800 mL). The organic layers were combined and the combined layers were dried over sodium sulfate. The solids were filtered and the filtrate was concentrated. The residue obtained was purified by flash-column chromatography on silica gel (100% diethyl ether) to furnish 3-methoxyfurfural 6 (21.2 g, 55%) as a light-yellow solid.

| TLC (20% ethyl acetate-hexanes) | $R_f$ = 0.34 (UV, CAM). |
|---|---|
| $^1$HNMR (500 MHz, CDCl$_3$), δ: | 7.51 (d, 2H, J = 1.5 Hz, ArH), 7.50-7.34 (m, 3H, ArH), 6.94 (m, 1H, =CHCH$_2$), 6.10 (ddd, 1H, J = 10.3, 1.5, 1.5 Hz, =CHC(O)), 5.36 (m, 2H, OCH$_2$Ph), 3.79 (d, 1H, J = 10.7 Hz, CHN(CH$_3$)$_2$), 2.83 (m, 2H, =CHCH$_2$), 2.78 (m, 1H, CHCHN(CH$_3$)$_2$), 2.46 (s, 6H, N(CH$_3$)$_2$), 0.84 (s, 9H, SiC(CH$_3$)$_3$), 0.27 (s, 3H, SiCH$_3$), 0.06 (s, 3H, SiCH$_3$). |
| $^{13}$CNMR (100 MHz, CDCl$_3$), δ: | 193.4, 187.9, 181.6, 167.7, 149.5, 135.2, 128.8, 128.8, 128.8, 128.6, 108.6, 83.5, 72.8, 59.8, 48.1, 42.2, 26.3, 25.8, 19.3, −2.2, −3.8. |
| IR (neat), cm$^{-1}$: | 2942 (s), 1719 (s), 1678 (s), 1602 (m), 1510(s), 1053 (s), 733 (s). |
| HRMS (ESI): | Calcd for (C$_{26}$H$_{34}$N$_2$O$_5$ + H)$^+$: 483.2315 Found: 483.2310 |

3-Methoxyfurfural (6):

| TLC (30% ethyl acetate-hexanes) | $R_f$ = 0.14 (UV, CAM). |
|---|---|
| $^1$HNMR (500 MHz, CDCl$_3$), δ: | 9.5 (s, 1H, HC=O), 7.45 (d, 1H, J = 2.0 Hz, FurH), 6.35 (d, 1H, J = 2.0 Hz, FurH), 3.86 (s, 3H, OCH$_3$). |
| $^{13}$CNMR (100 MHz, CDCl$_3$), δ: | 173.9, 158.6, 148.2, 137.4, 102.3, 58.9. |
| IR (neat), cm$^{-1}$: | 3131 (w), 2945 (w), 2838 (w), 2808 (w), 1653 (s), 1586 (s), 1469 (s), 1426 (s), 1364 (s),1269 (s), 1109 (s), 988 (m). |
| HRMS (ESI): | Calcd for (C$_{26}$H$_{34}$N$_2$O$_5$ + H)$^+$: 127.0935 Found: 127.0936 |

Iodide (13):

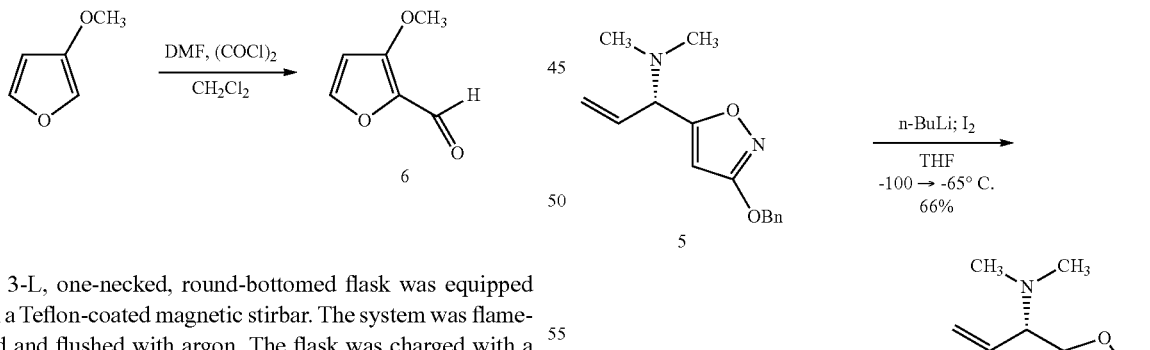

A 3-L, one-necked, round-bottomed flask was equipped with a Teflon-coated magnetic stirbar. The system was flame-dried and flushed with argon. The flask was charged with a solution of N,N-dimethylformamide (31.9 mL, 413 mmol, 1.35 equiv) in dichloromethane (1.2 L). The solution was cooled to 0° C. in a dry ice-acetone bath, and then oxalyl chloride (32.5 mL, 367 mmol, 1.2 equiv) was added over 16 min. Vigorous bubbling occurred and a white solid precipitated. After stiffing for 20 min, the reaction mixture was cooled to −40° C. by addition of dry ice to the cooling bath and a solution of 3-methoxyfuran (Meister, C.; Scharf, H.-D. Synthesis 1981, 737-739) (30 g, 306 mmol, 1 equiv) in dichloromethane (100 mL) was added via cannula. A dark-brown A 200-mL, one-necked, round-bottomed flask was equipped with a Teflon-coated magnetic stirbar and flame-dried. The flask was charged with a solution of isoxazole 5 (2.00 g, 7.75 mmol, 1 equiv) in tetrahydrofuran (52 mL). The solution was cooled to −100° C. in a liquid dinitrogen-ethanol bath, and then a solution of n-butyllithium in hexanes (2.50 M, 3.56 mL, 8.91 mmol, 1.15 equiv) was added dropwise over 9 min. The reaction solution was warmed to −65° C. over 15 min. The mixture was stirred at −65° C. for 60 min and then a solution of iodine (2.56 g, 10.1 mmol, 1.30 equiv) in tetrahydrofuran (25 mL) was added via cannula. The reaction solution was stirred at −65° C. for 15 min, and then the cooling bath was removed. The product solution was partitioned between aqueous potassium phosphate buffer (pH 7.0, 0.05 M, 25 mL), saturated aqueous sodium thiosulfate solution (25 mL), and ethyl acetate (150 mL). The organic layer was washed with saturated aqueous sodium chloride solution and the washed solution was dried over sodium sulfate. The solids were filtered and the filtrate was concentrated. The residue obtained was purified by flash-column chromatography on silica gel (40% ethyl acetate-hexanes) to furnish the iodide 13 (1.97 g, 66%) as a pale yellow solid.

A 5-mL, one-necked, round-bottomed flask was equipped with a Teflon-coated magnetic stirbar flame-dried. The flask was charged with a solution of iodide 13 (49 mg, 0.13 mmol, 1 equiv) in tetrahydrofuran (850 μL). The solution was cooled to −20° C. in a dry ice-acetone bath, and then a solution of isopropylmagnesium chloride in tetrahydrofuran (2.0 M, 96 μL, 0.19 mmol, 1.5 equiv) was added dropwise. The resulting pale-yellow solution was stirred for 40 min, and then a solution of 3-methoxyfurfural (27 mg, 0.22 mmol, 1.7 equiv) in tetrahydrofuran (450 μL) was added dropwise via cannula. The reaction mixture was stirred for 5 min, and then aqueous potassium phosphate solution (pH 7.0, 0.05 M, 4 mL) was added. The product solution was extracted with dichloromethane (2×10 mL). The organic layers were combined and the combined solution was dried over sodium sulfate. The solids were filtered and the filtrate was concentrated. The residue obtained was purified by flash-column chromatogra-

| | |
|---|---|
| TLC (40% ethyl acetate-hexanes) | $R_f$ = 0.32 (UV, CAM). |
| $^1$HNMR (500 MHz, CDCl$_3$), δ: | 7.47 (d, 2H, J = 7.3 Hz, ArH), 7.42-7.36 (m, 3H, ArH), 6.03 (ddd, 1H, J = 17.6, 10.3, 7.8 Hz, CH$_2$=CH), 5.34-5.27 (m, 4H, CHH=CH, OCH$_2$Ar), 4.06 (d, 1H, J = 7.8 Hz, CHN(CH$_3$)$_2$), 2.29 (s, 6H, N(CH$_3$)$_2$). |
| $^{13}$CNMR (125 MHz, C$_6$D$_6$), δ: | 171.7, 170.9, 135.7, 134.4, 128.8, 128.7, 128.3, 119.7, 72.2, 66.8, 43.2. |
| IR (neat), cm$^{-1}$: | 3033 (w), 2981 (m), 2949 (m), 2866 (m), 2824 (m), 2779 (m), 1596 (s), 1508 (s), 1455 (s), 1437 (s), 1361 (s), 1254 (m), 1088 (s). |

Diels Alder Precursors (7a and 7b):

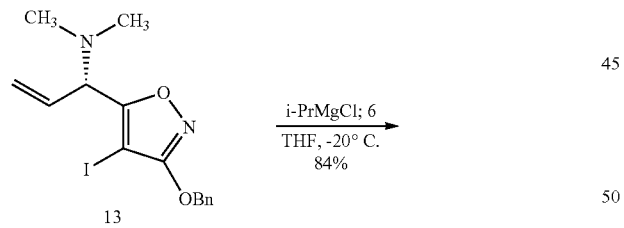

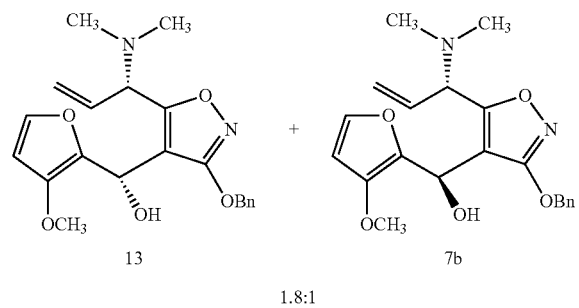

phy on silica gel (70% diethyl ether-pentane) to furnish the Diels-Alder precursors 7a and 7b (41 mg, 84%, 1.8:1 mixture of epimers) as a pale yellow oil. See above for characterization.

Example 3

Synthesis of Bromo-Isoxazole and its Use in Fragment Coupling Reaction Using Magnesium-Halogen Exchange The synthetic route to the furan Diels-Alder precursor was further developed in order to avoid the low-temperature metalation coupling reaction. Preliminary studies indicated that an aryl iodide could undergo a magnesium-halogen exchange reaction at −20° C., which is quite reasonable for a large scale production of the Diels-Alder precursor. We found that a bromine atom could be introduced onto the isoxazole ring by electrophilic bromination at an early stage as shown in the scheme below:

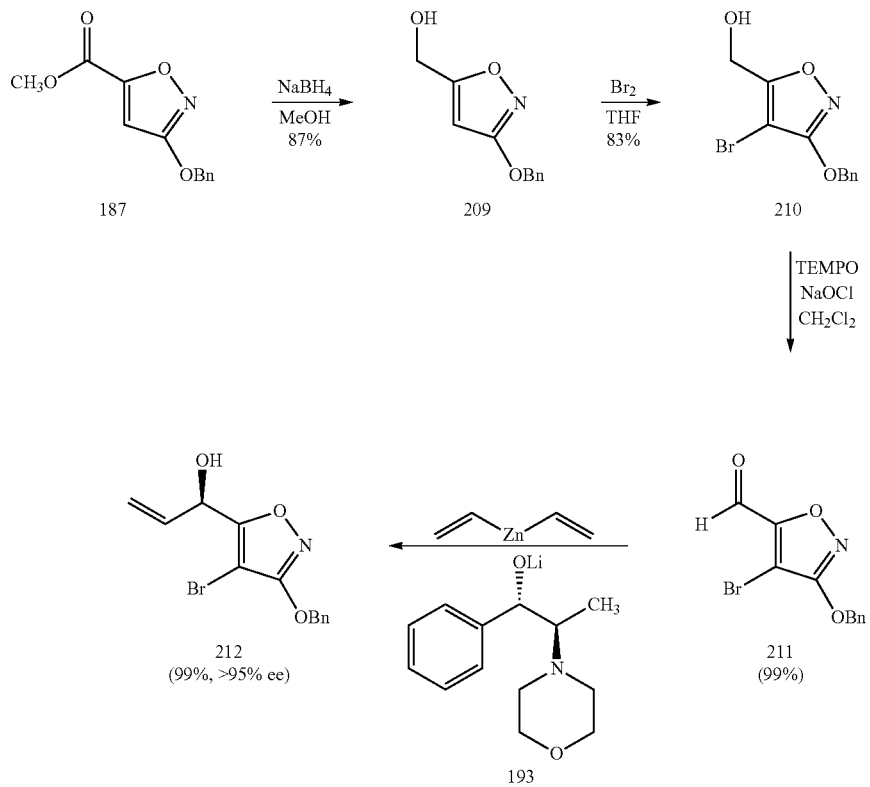

As shown in the scheme, the brominated aldehyde was subjected to enantioselective addition of the vinyl moiety using divinyl zinc and a chiral aminoalkoxide. This reaction gave the allylic alcohol in quantitative yield and >95% ee. The mesylation/displacement sequence that had worked well with the desbromo allylic alcohol worked well using additives such as methanol or trifluoroethanol. These additives are thought to attenuate the basicity of dimethylamine while still allowing it to act as a nucleophile. For example, two equivalents of trifluoroethanol completely suppressed the formation of the undesired vinyl mesylate, but this suppression was accompanied by an increase in the formation of the linear amine. The transformation as shown in the scheme below was eventually accomplished in 65% yield by treating the mesylate of bromo allylic alcohol with dimethylamine and a 1.1-fold excess of trifluoroethanol at −30° C. for 3 days to furnish the desired allylic amine.

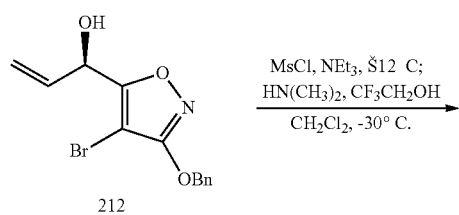

-continued

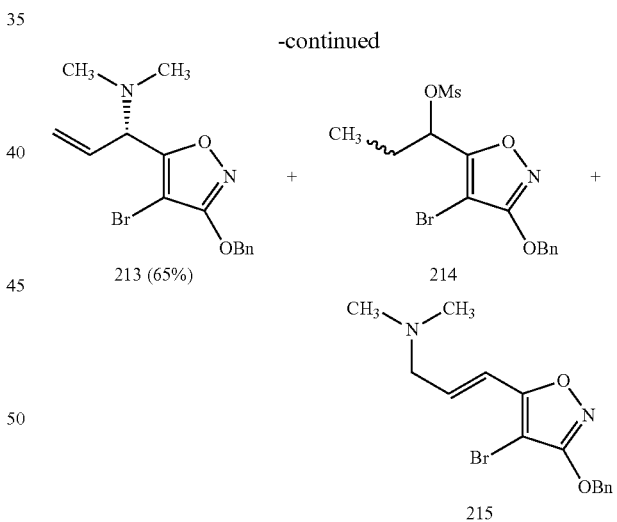

Fragment coupling of the bromo allylic amine and 3-methoxyfurfural was performed by treatment of the bromo allylic amine with iso-PrMgCl (Wakefield, B. J. Preparation of Organomagnesium Compounds. In *Organomagnesium Compounds in Organic Synthesis*; Academic Press, Inc.: San Diego, 1995 pp 51-59; Boudier, A.; Bromm, L. O.; Lotz, M.; Knochel, P. *Angew. Chem., Int. Ed. Engl.* 2000, 39, 4414-4435) at 0° C. followed by addition of 3-methoxyfurfural, giving a mixture of Diels-Alder precursors (1.4:1 mixture, epimeric at the secondary carbinol) in 99% yield as shown in the scheme below.

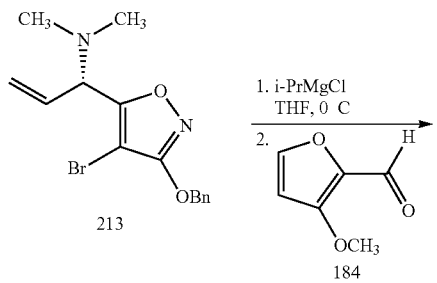

for 5 h, then an additional portion of bromine (200 µL, 3.89 mmol, 0.400 equiv) was added dropwise. The reaction mixture was stirred for 60 min, then saturated aqueous sodium thiosulfate (15 mL) was added. The product solution was partitioned between ethyl acetate (75 mL) and aqueous potassium phosphate buffer solution (pH 7.0, 0.05 M, 20 mL). The aqueous layer was extracted with ethyl acetate (50 mL). The organic layers were combined and the combined solution was washed with saturated aqueous sodium chloride solution (50 mL). The washed solution was dried over sodium sulfate, the solids were filtered, and the filtrate was concentrated. The residue obtained was purified by flash-column chromatography on silica gel (30% ethyl acetate-hexanes) to furnish the bromide 210 (2.30 g, 83%) as a white, crystalline solid.

| | |
|---|---|
| TLC (40% ethyl acetate-hexanes): | $R_f$ = 0.33 (UV, CAM). |
| $^1$H NMR (500 MHz, CDCl$_3$), δ: | 7.47 (d, 2H, J = 7.8 Hz, ArH), 7.41-7.36 (m, 3H, ArH), 5.33 (s, 2H, OCH$_2$Ph), 4.68 (d, 2H, J = 6.9 Hz, ArCH$_2$OH), 2.13 (t, 1H, J = 6.7 Hz, OH). |
| $^{13}$C NMR (125 MHz, C$_6$D$_6$), δ: | 168.6, 167.9, 135.1, 128.6, 128.6, 128.2, 83.9, 72.1, 55.3. |
| IR (neat), cm$^{-1}$: | 3377 (bs), 3034 (w), 2935 (w), 1620 (m), 1520 (s), 1453 (s), 1360 (s), 1273 (w), 1211 (w), 1106 (s), 1019 (s). |
| HRMS (ESI): | Calcd for (C$_{11}$H$_{10}$BrNO$_3$ + H)$^+$: 283.9922 |
| | Found: 283.9933 |

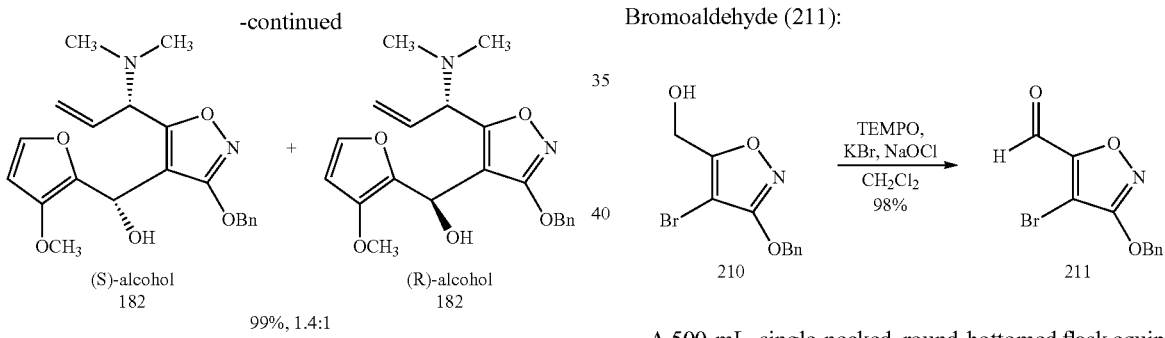

-continued (S)-alcohol 182 + (R)-alcohol 182

99%, 1.4:1

Experimentals
Bromoalcohol (210)

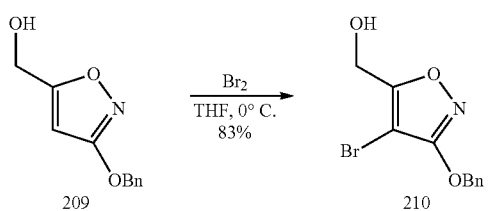

A 100-mL, single-necked, round-bottomed flask equipped with a Teflon-coated magnetic stirring bar was flame-dried, then flushed with argon. The flask was charged with a solution of alcohol 209 (2.00 g, 9.75 mmol, 1 equiv) in tetrahydrofuran (19.5 mL). The solution was cooled to 0° C. in an ice-water bath, then bromine (1.00 mL, 19.5 mmol, 2.00 equiv) was added dropwise. The resulting pale-red solution was stirred Bromoaldehyde (211):

A 500-mL, single-necked, round-bottomed flask equipped with a Teflon-coated magnetic stirring bar was flame-dried, then flushed with argon. The flask was charged with a solution of alcohol 210 (4.30 g, 15.1 mmol, 1 equiv) in dichloromethane (151 mL). Saturated aqueous sodium bicarbonate solution (75 mL), potassium bromide (1.74 g, 14.7 mmol, 0.97 equiv), the stable free radical 2,2,6,6-tetramethyl-1-piperidinyloxy (212 mg, 1.36 mmol, 0.090 equiv) were added sequentially to the reaction mixture at 23° C. Aqueous sodium hypochlorite solution (21.8 mL, 0.83 M, 18.1 mmol, 1.2 equiv) was then added to the biphasic mixture. The red biphasic mixture was stirred for 15 min, then saturated aqueous sodium thiosulfate solution (75 mL) was added. The product solution was partitioned and the aqueous layer was further extracted with dichloromethane (150 mL). The organic layers were combined and the combined solution was dried over sodium sulfate. The solids were filtered, and the filtrate was concentrated. The residue obtained was purified by flash-column chromatography on silica gel (25% ethyl acetate-hexanes) to furnish the aldehyde 211 (4.19 g, 98%) as a white, crystalline solid.

| | |
|---|---|
| TLC (40% ethyl acetate-hexanes): | $R_f$ = 0.44 (UV, CAM). |
| $^1$H NMR (500 MHz, CDCl$_3$), δ: | 9.85 (s, 1H, ArCHO), 7.48 (d, 2H, J = 7.1 Hz, ArH), 7.42-7.40 (m, 3H, ArH), 5.40 (s, 2H, ArOCH$_2$Ph). |
| $^{13}$C NMR (125 MHz, C$_6$D$_6$), δ: | 177.1, 169.0, 160.6, 134.5, 128.9, 128.7, 128.4, 92.7, 72.9. |
| IR (neat), cm$^{-1}$: | 1703 (s), 1590 (w), 1514 (s), 1453 (m), 1361 (m), 1275 (m), 1213 (w), 1109 (s), 936 (w). |
| HRMS (ESI): | Calcd for (C$_{11}$H$_8$BrNO$_3$ + H)$^+$: |
| Found: | |

Bromoallylic Alcohol (212):

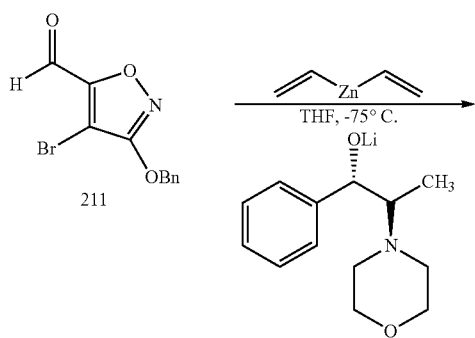

A 100-mL, single-necked, round-bottomed flask equipped with a Teflon-coated magnetic stirring bar was flame-dried, then flushed with argon. The flask was charged with a solution of (1S,2R)-2-morpholin-4-yl-1-phenylpropanol (1.18 g, 5.31 mmol, 2.00 equiv) in toluene (17.7 mL). The solution was cooled to 0° C. in an acetone bath, and a solution of n-butyllithium in hexanes (2.50 M, 2.10 mL, 5.31 mmol, 2.00 equiv) was added to the cooled solution via syringe. The reaction solution was stirred for an additional 30 min at 0° C. after the addition, and then a solution of divinylzinc (0.28 M, prepared as described above, 19.0 mL, 5.31 mmol, 2.0 equiv) was added via syringe over 5 min. The reaction mixture was stirred at 0° C. for 1 h, then was cooled to an internal temperature of –75° C. by addition of dry ice to the cooling bath.

A solution of aldehyde 211 (750 mg, 2.65 mmol, 1 equiv) in toluene (3.5 mL) was added to the reaction mixture at –75° C. over 5 min via cannula. The reaction mixture was stirred at –75° C. for 50 min, and the cooling bath was removed. When the reaction mixture had warmed to –30° C., aqueous citric acid solution (30% by weight, 40 mL) was added. The biphasic mixture was allowed to warm to 23° C. and diluted with ethyl acetate (50 mL). The layers were separated, and the organic layer was washed sequentially with water (700 mL) and brine (700 mL). The washed solution was dried over sodium sulfate, and the dried solution was filtered. The filtrate was concentrated and the residue obtained was purified by flash-column chromatography on silica gel (20% ethyl acetate-hexanes) to furnish the allylic alcohol 212 (804 mg, 98%, 95% ee by Mosher ester analysis) as a clear, colorless oil.

| | |
|---|---|
| TLC (20% ethyl acetate-hexanes): | $R_f$ = 0.28 (UV, CAM). |
| $^1$H NMR (500 MHz, CDCl$_3$), δ: | 7.46 (d, 2H, J = 7.3 Hz, ArH), 7.42-7.36 (m, 3H, ArH), 6.09 (ddd, 1H, J = 16.6, 10.3, 5.9 Hz, CH$_2$=CH), 5.46 (d, 1H, J = 17.1, trans-CHH=CH), 5.35 (d, 1H, J = 10.7 Hz, cis-CHH=CH), 5.32-5.30 (m, 3H, OCH$_2$Ar, CHOH), 2.58 (d, 1H, OH). |
| $^{13}$C NMR (125 MHz, C$_6$D$_6$), δ: | 168.6, 168.2, 135.1, 134.1, 128.6, 128.6, 128.2, 118.4, 82.8, 72.1, 67.6. |
| HRMS (ESI): | Calcd for (C$_{13}$H$_{12}$BrNO$_3$ + H)$^+$: 310.0073<br>Found: 310.0076 |

Allylic Amine (213):

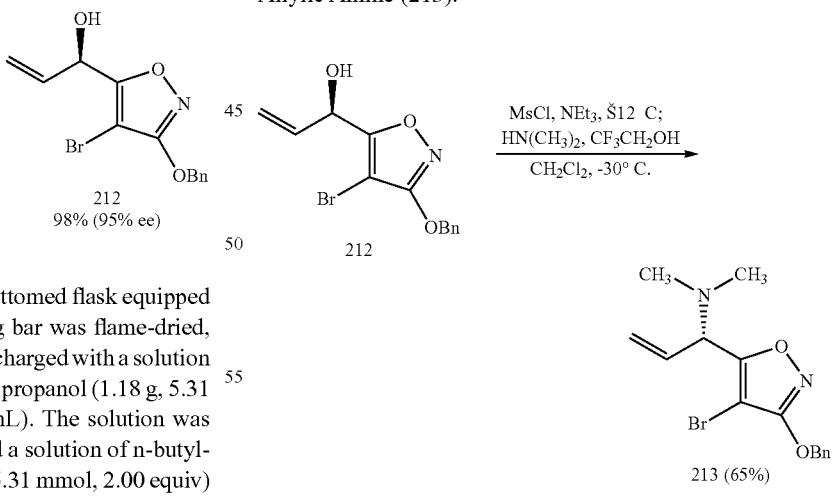

A 10-mL, single-necked, round-bottomed flask equipped with a Teflon-coated magnetic stirring bar was flame-dried, then flushed with argon. The flask was charged with a solution of alcohol 212 (128 mg, 0.413 mmol, 1 equiv) in dichloromethane (1.37 mL). The solution was cooled to –15° C. and triethylamine (81 µL, 0.58 mmol, 1.4 equiv) and methanesulfonyl chloride (39 µL, 0.50 mmol, 1.2 equiv) were added sequentially. The reaction mixture was stirred at −15° C. for 15 min, then was cooled to −45° C. 2,2,2-Trifluoroethanol (281 μL, 3.72 mmol, 9.00 equiv) and a solution of dimethylamine (3.6 M in CH$_2$Cl$_2$, 800 μL, 2.9 mmol, 7.0 equiv) were added sequentially and the reaction mixture was stirred at −30° C. for 92 h. The product solution was warmed to 23° C. and partitioned between dichloromethane (15 mL) and aqueous potassium phosphate solution (pH 7.0, 0.05 M, 5 mL). The aqueous layer was further extracted with dichloromethane (10 mL) and the organic layers were combined. The combined layers were dried over sodium sulfate, and the dried solution was filtered. The filtrate was concentrated and the residue obtained was purified by flash-column chromatography on silica gel (1.5% methanol-dichloromethane) to furnish the allylic amine 213 (90 mg, 65%) as a clear, colorless oil.

| | |
|---|---|
| TLC (40% ethyl acetate-hexanes): | $R_f$ = 0.44 (UV, CAM). |
| $^1$H NMR (500 MHz, CDCl$_3$), δ: | 7.47 (d, 2H, J = 7.0 Hz, ArH), 7.42-7.36 (m, 3H, ArH), 6.04 (ddd, 1H, J = 18.0, 10.3, 7.8 Hz, CH$_2$=CH), 5.34-5.28 (m, 4H, CHH=CH, OCH$_2$Ar), 4.08 (d, 1H, J = 7.8 Hz, CHN(CH$_3$)$_2$), 2.29 (s, 6H, N(CH$_3$)$_2$). |
| IR (neat), cm$^{-1}$: | 3089 (w), 3067 (w), 2981 (m), 2949 (m), 2868 (m), 2824 (m), 2779 (m), 1610 (m), 1517 (s), 1517 (s), 1446 (s), 1363 (s), 1258 (m), 1102 (s), 1028 (m), 940 (s). |
| HRMS (ESI): | Calcd for (C$_{15}$H$_{17}$BrN$_2$O$_2$ + H)$^+$: 337.0546<br>Found: 337.0543 |

Diels Alder Precursors 182

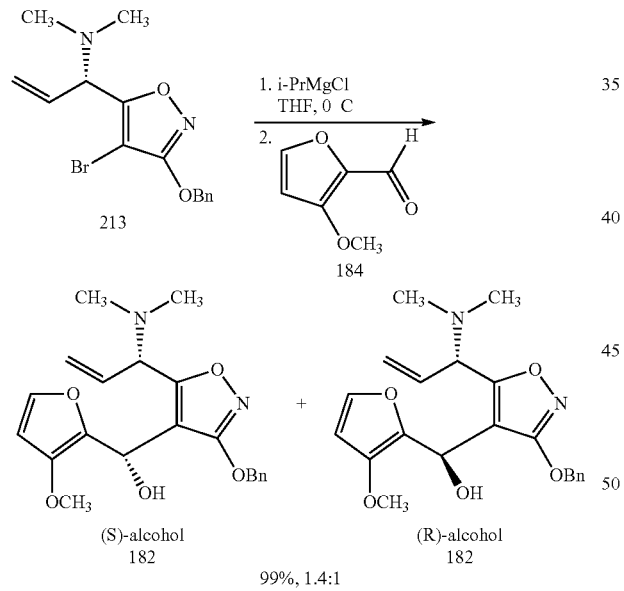

(S)-alcohol 182       (R)-alcohol 182
99%, 1.4:1

A 5-mL, single-necked, round-bottomed flask equipped with a Teflon-coated magnetic stirring bar was flame-dried, then flushed with argon. The flask was charged with a solution of bromide 213 (61 mg, 0.18 mmol, 1 equiv) in tetrahydrofuran (904 μL). The solution was cooled to 0° C. in an ice-water bath, then a solution of isopropylmagnesium chloride in tetrahydrofuran (2.0 M, 180 μL, 0.36 mmol, 2.0 equiv) was added dropwise. The resulting pale-yellow solution was stirred for 32 min, then a solution of 3-methoxyfurfural (45.5 mg, 0.361 mmol, 2.0 equiv) in tetrahydrofuran (600 μL) was added dropwise via cannula. The reaction mixture was stirred for 5 min, then aqueous potassium phosphate solution (pH 7.0, 0.05 M, 3 mL) was added. The product solution was extracted with dichloromethane (2×10 mL). The organic layers were combined and the combined solution was dried over sodium sulfate. The solids were filtered and the filtrate was concentrated. The residue obtained was purified by flash-column chromatography on silica gel (70% ethyl ether-pentane) to furnish the Diels-Alder precursors 182 (69 mg, 99%, 1.4:1 mixture of epimers) as a pale yellow oil. The product provided spectroscopic data identical to those presented above save for differences attributable to the varying ratio of product diastereomers.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of formula (VII):

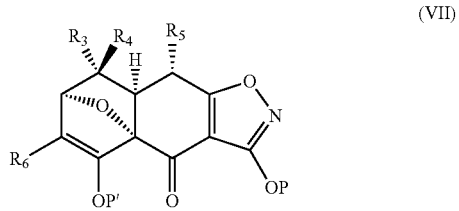

(VII)

wherein
R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; =O (taken with R$_4$); —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —$C(=O)R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —$OR_F$, —CN, —SCN, —$SR_F$, alkylthio, arylthio, —$NO_2$, amino, —$N(R_F)_2$, and —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is hydrogen or an oxygen-protecting group; and

P' is $C_1$-$C_6$ alkyl;

and salts, tautomers, stereoisomers, enantiomers, diastereomers, and derivatives thereof.

2. A compound of formula (VI):

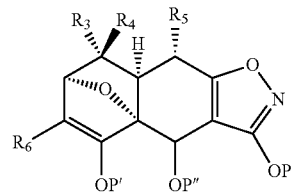

(VI)

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O (taken with $R_4$); —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; =O (taken with $R_3$); —$C(=O)R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstituted aliphatic, substituted or unsubstituted heteroaliphatic, substituted or unsubstituted alkoxy, —$OR_F$, —CN, —SCN, alkylthio, arylthio, —$NO_2$, amino, —$N(R_F)_2$, and —$C(R_F)_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P is hydrogen or an oxygen-protecting group;

P' is hydrogen, $C_1$-$C_6$ alkyl, acyl, or an oxygen-protecting group; and

P'' is hydrogen or an oxygen-protecting group;

and salts, tautomers, stereoisomers, enantiomers, diastereomers, and derivatives thereof.

3. The compound of claim 2, wherein P is benzyl.

4. The compound of claim 2, wherein P'' is hydrogen.

5. The compound of claim 2, wherein P' is methyl.

6. The compound of claim 2, wherein the compound is of the formula:

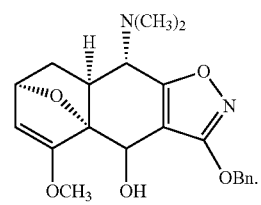

7. The compound of claim 2, wherein the compound is of the formula:

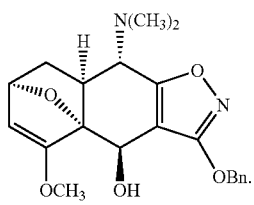
8. The compound of claim 2, wherein the compound is of the formula:
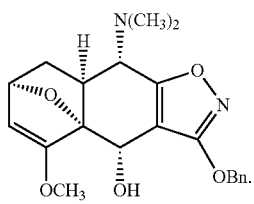
9. The compound of claim 1, wherein P' is methyl.
10. The compound of claim 1, wherein P is benzyl.
11. The compound of claim 1, wherein the compound is of the formula:
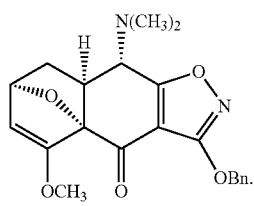
* * * * *

UNITED STATES PATENT AND TRADEMARK OFFICE
CERTIFICATE OF CORRECTION

PATENT NO. : 7,960,559 B2  Page 1 of 1
APPLICATION NO. : 12/833628
DATED : June 14, 2011
INVENTOR(S) : Andrew G. Myers et al.

It is certified that error appears in the above-identified patent and that said Letters Patent is hereby corrected as shown below:

In claim 2, at column 90, line 37, please amend the claim as follows:

. . . alkoxy, -OR$_F$, -CN, -SCN, -SR$_F$, alkylthio, . . .

Signed and Sealed this
Thirteenth Day of September, 2011

David J. Kappos
*Director of the United States Patent and Trademark Office*